United States Patent
Koffas et al.

(10) Patent No.: US 7,338,791 B2
(45) Date of Patent: Mar. 4, 2008

(54) PRODUCTION OF FLAVONOIDS BY RECOMBINANT MICROORGANISMS

(75) Inventors: Mattheos Koffas, Williamsville, NY (US); Effendi Leonard, Buffalo, NY (US); Yajun Yan, Amherst, NY (US); Joseph Chemler, Brookfield, IL (US)

(73) Assignee: The Research Foundation of State University of New York, Buffalo, NY (US)

( * ) Notice: Subject to any disclaimer, the term of this patent is extended or adjusted under 35 U.S.C. 154(b) by 0 days.

(21) Appl. No.: 11/178,912

(22) Filed: Jul. 11, 2005

(65) Prior Publication Data

US 2006/0019334 A1  Jan. 26, 2006

Related U.S. Application Data

(60) Provisional application No. 60/586,903, filed on Jul. 10, 2004.

(51) Int. Cl.
*C12P 17/06* (2006.01)
*C12P 21/06* (2006.01)
*C02N 1/20* (2006.01)
*C07H 21/04* (2006.01)

(52) U.S. Cl. .................. 435/125; 435/41; 435/69.1; 435/252.8; 536/23.3

(58) Field of Classification Search ............ None
See application file for complete search history.

(56) References Cited

U.S. PATENT DOCUMENTS

2005/0208643 A1* 9/2005 Schmidt-Dannert et al. ..... 435/252.31

OTHER PUBLICATIONS

Hwang, et al. Applied and Environ Microbiol, May 2003, pp. 2699-2706.*

Honda et al. ( Plant Phys Biochem. ( 2002, 40, 955-962).*

Hwang, et. al, Production of Plant-Specific Flavanones by *Escherichia coli* Containing an Artificial Gene Cluster, Applied and Environmental Microbiology, May 2003, pp. 2699-2706.

Ralston, et. al., Partial Reconstruction of Flavonoid and Isoflavonoid Biosynthesis in Yeast Using Soybean Type I and Type II Chalcone Isomerases, Plant Physiology, Preview Section, Jan. 2005, pp. 1-14.

Schijlen, et. al., Modification of flavonoid biosynthesis in crop plants, Phytochemistry, Sep. 2004, vol. 65, pp. 2631-2648.

* cited by examiner

*Primary Examiner*—Rebecca E. Prouty
*Assistant Examiner*—Md Younus Meah
(74) *Attorney, Agent, or Firm*—Hodgson Russ LLP

(57) ABSTRACT

Methods and compositions are provided for production of flavonoids in microbial hosts. The compositions comprises a set of genes which encode for enzymes involved in one or more steps in the biosymthetic pathway for the conversion of phenylpropanoids to various flavonoids. The method comprises the steps of introducing the set of genes into a heterologous host cell, allowing growth of the cells in a suitable medium such that the expression of the genes results in production of enzymes. When specific substrate(s) is/are provided to the transformed cell, the enzymes act on the substrate(s) to produce the desired flavonoids.

3 Claims, 27 Drawing Sheets

PRODUCTION OF FLAVONOIDS BY RECOMBINANT MICROORGANISMS

This application claims priority to U.S. provisional application No. 60/586,903, filed on Jul. 10, 2004, the disclosure of which is incorporated herein by reference.

This work was supported by Government funding under grant no. BES-0331404 from the National Science Foundation. The Government has certain rights in the invention.

BACKGROUND

Flavonoids are a diverse family of plant polyphenolic substances. The basic structure of a flavonoid molecule, consists of three phenolic rings referred to as A, B and C rings (FIG. 1). They are derived from a combination of metabolites synthesized from phenylalanine and acetic acid. These compounds include several major subgroups that are found in most higher plants, such as chalcones, flavanones, flavones, flavonols, flavan-3-ols, flavan-4-ols, dihydroflavonols, anthocyanins, proanthocyanidins and condensed tannins. Flavonoids have key roles in signaling between plants and microbes, in male fertility of some species, in defense as antimicrobial agents and in UV protection (Winkel-Shirley, 2001, *Plant Physiol.*, 126(2): 485-493). A general biosynthetic pathway for the flavonoids is shown in FIG. 1.

Flavanones are the common precursors of a wide variety of flavonoids. Their demonstrated anti-oxidant properties and health benefits for a wide array of human pathological conditions have generated a significant research interest in this general area.

Flavones are comprised of two benzene rings linked through a heterocyclic pyrone (Middleton et al., Pharmacol. Rev. 52:673-751, 2000). Flavones, such as chrysin, apigenin and luteolin, exhibit an array of pharmacological properties, including anti-anxiety effects (Viola et al., 1995, *Planta Med.*, 61:213-216; Wolfman et al., *Pharmacol. Biochem.* 47:1-4, 1994; Wolfman et al., 1995, *J. Neurochem.* 65:S167), improvement of cardiac function after ischemia (Lebeau, 2001. *Bioorg. Med. Chem. Lett.* 11:23-27; Rump et al, 1994, *Gen. Pharmacol.* 25:1137-1142; Schussler et al., 1995, *Gen. Pharmacol.* 26:1565-1570) and anti-estrogenic effects in breast cancer cell cultures (Miksicek, 1995. *P. Soc. Exp. Biol. Med.* 208:44-50). Flavones occur only in a relatively small food group that includes parsley, thyme, celery and sweet red pepper (Ross et al, 2002, Annu. Rev. Nutr. 22:19-34).

Flavone and flavanone biosynthesis starts with the conversion of cinnamic acid to p-coumaric acid by a P450 monooxygenase, cinnamate 4-hydroxylase (C4H). p-Coumaric acid is then converted to 4-coumaroyl-CoA by 4-coumaroyl:CoA ligase (4CL). Next, chalcone synthase (CHS) catalyzes a condensation reaction of 4-coumaroyl-CoA with three molecules of malonyl-CoA to form tetrahydroxychalcone. Following this reaction, chalcone isomerase (CHI) performs the stereospecific isomerization reaction of tetrahydroxychalcone to (2S)-flavanone, which is the branch point precursor of many important downstream flavonoids, including flavones. In most cases, a membrane bound cytochromic P450-monooxygenase, flavone synthase II (FSII), catalyzes the biosynthesis of flavones from (2S)-flavanones. However, in certain species of Apiceae, this reaction is performed by the soluble flavone synthase I (FSI) (FIG. 1) (Lukacin et al., 2001, *Arch. Biochem. Biophys.* 393:177-83; Martens et al., 2001, *Phytochemistry* 58:43-46).

Among all flavonoid molecules, flavonols are regarded as the most ancient and wide spread (Stafford, 1991). In recent years, their antioxidant activity has attracted much attention due to their potential in the prevention of oxidative stress-related chronic diseases. In that respect, numerous studies have revealed the diverse biological effects of flavonols in such areas as apoptosis induction, antimutagenesis, histamine-release inhibition and angiogenesis inhibition (Formica, et al., 1995; Lambert, et al., 2005; Lamson, et al., 2000).

In the biosynthesis of flavonols, (2S)-flavanones are formed as described above. Natural (2R, 3R)-trans-dihydroflavonols are subsequently formed from (2S)-flavanones by the action of flavanone 3 β-hydroxylase (FHT). Finally flavonol synthase (FLS), a 2-oxoglutarate-dependent dioxygenase, catalyzes the desaturation of dihydroflavonols to flavonols.

Among the natural pigments in plants, anthocyanins are the largest water-soluble group, found in most fruits, flower petals and leaves. The colors range from salmon pink, scarlet and magenta, to violet, purple and blue. These ubiquitous compounds are fascinating in that they can exist in many structural forms, both simple and complex, governed by physiological regulations and chemical modifications which have profound effects on their stabilities and colors. Anthocyanins play important roles such as recruitment of pollinators and seed dispersers, and UV protection. Initial interest in the practical application of these brightly colored anthocyanins has stemmed from their potential as replacements for banned dyes because they have no apparent adverse effects to human health (Brouillard, 1982, Anthocyanins as Food Colors, Academic Press, Inc, New Yor, N.Y.). Recently, however, much attention has been drawn to flavonoid-derived, plant products (including anthocyanins) due to their general antioxidant properties (Kahkonen et al., 2003, J. Agric. Food Chem., 51:628-633; Noda et al., 2000, Toxicology, 148:119-123; Satue-Gracia et al., 1997, J. Agric. Food Chem., 145: 3362-3367) and a consistent association between the consumption of diets rich in fruits and vegetables and a lower risk for chronic diseases, including cancer and cardiovascular disease (Hannum, 2004, Crit. Rev. Food Sci. Nutr., 44:1-17; Middleton et al., 2000, Pharmocolo. Rev., 52:673-751). As a result, anthocyanins are becoming attractive targets for fermentation production from well-characterized microbial hosts, such as *Escherichia coli*.

Six major classes of anthocyanidins (the aglycon forms of anthocyanins) exist: pelargonidin, cyanidin, delphinidin, peonidin, malvidin and petunidin. The basic structure of an anthocyanin is a glycosylated form of polyhydroxy and polymethoxy derivatives of 2-phenylbenzopyrylium or flavylium salts. Biosynthesis of anthocyanins proceeds via the pathway chalcone→flavanone→dihydroflavonol→anthocyanidin→anthocyanin (FIG. 1). Flavanone is synthesized as described above. Dihydroflavonols are subsequently formed from flavanone by the action of flavanone 3-hydroxylase (FHT). In the next step, dihydroflavonol 4-reductase (DFR) reduces the colorless dihydroflavonols, either dihydrokaempferol (DHK), dihydroquercetin (DHQ) or dihydromyricetin (DHM), to their respective 3,4-cis-leucoanthocyanidins in an NADPH-dependent reaction. The three substrates of DFR are very similar in structure, differing only in the number of additional hydroxyl groups on the β phenyl ring, which are not subject to this enzymatic reaction. DFRs from many plant species (but not all) investigated so far can utilize all three substrates. The colorless, unstable leucoanthocyanidins are the immediate precursors of the first colored metabolite in the biosynthetic pathway, anthocyanidins. This 2-oxoglutarate-dependent reaction is catalyzed by anthocyanidin synthase (ANS). Anthocyanidins are hardly detected in plant tissues, due to their instability. Instead, anthocyanidin 3-glucosides are the first stable colored metabolites from this pathway that are detectable in plants and are derived from anthocyanidins through the action of the enzyme UDP-glucose:flavonoid 3-O-glucosyltransferase (3-GT). The cDNA sequences of a large number of enzymes involved in the anthocyanin biosynthesis pathway from various plant species are now available.

Although attempts have been made to synthesize flavonoids in non-plant systems, a satisfactory system has not been developed. Recently, Hwang et. al. demonstrated the synthesis of plant-specific flavanones for the first time in *E. coli*, by expressing three genes from heterologous sources that convert phenylalanine to tetrahydroxychalcone. However, the end product (a flavanone) was produced by raising the pH to 9 which spontaneously converted tetrahydroxy-chalcone to the natural flavanone (2S)-naringenin and its unnatural epimer (2R)-naringenin (hwang et al., 2003, *Appl. Environ. Microbiol.* 69:2699-2706). Further, so far, no microbial or yeast production has been demonstrated for anthocyanins.

Thus, despite the realization of a need for systems to produce flavonoids in heterologous systems, and the elucidation of cDNA sequences of a large number of enzymes involved in the biosynthetic pathway for flavonoids from various plants, a suitable system and method for the synthesis of variety of flavonoids in microbial systems has not been developed. Therefore, there continues to be a need for the development of methods and systems which can produce usable quantities of flavonoids that can meet the increasing need for those compounds without the need for chemical conversion.

SUMMARY OF THE INVENTION

In the present invention are provided methods and compositions for production of flavonoids in microbial hosts. The method comprises the steps of introducing a set of genes into a heterologous host cell, allowing growth of the cells in a suitable medium such that the expression of the genes results in production of enzymes. When specific substrate(s) is/are provided to the transformed cell, the enzymes act on the substrate(s) to produce the desired flavonoids.

In one embodiment is presented a set of genes which encodes for enzymes which can convert substrates belonging to the general category of phenylpropanoids and result in the production of flavanones.

In another embodiment is presented a set of genes which encodes for enzymes which can convert flavanones to a variety of other flavonoids. These flavonoids include flavones, flavan-3-ols, flavan-4-ols, flavonols and anthocyanins, and intermediates in the synthesis of the above compounds. Such intermediates include dihydroflavonols, leucoanthocyanidins and anthocyanidins.

In another embodiment is presented a set of genes which encode for enzymes which can convert the phenylpropanoids to a flavonoid selected from the group consisting of flavanones, flavones, flavonols, dihydroflavonols, flavan-3-ols, flavan-4-ols, anthocyanins and anthocyanidins.

In another embodiment is provided a method for production of flavonoids in microbial host which have been transfected with a set of genes comprising genes which encode for enzymes for the biosynthetic pathway of various flavonoids. The method comprises the steps of transfecting microbial host cells with a set of genes, culturing the host cells in a suitable growth medium allowing the expression of the genes, providing a suitable substrate to the host cells such that the enzymes produced by the expression of the genes can act upon the substrate effecting the production of the desired flavonoid. The flavonoid produced can then be purified by routine methods.

In another embodiment are provided host cells into which have been introduced a set of genes as described herein. The set of genes encode for enzymes for the synthesis of various flavonoids from specific substrates. When these substrates are provided to the host cells expressing the introduced genes, the synthesis of the desired flavonoids occurs. The flavonoids can then be isolated by routine methods.

DESCRIPTION OF THE INVENTION

This invention provides compositions and methods for the production of flavonoids in a non-plant host cell by introducing a set of heterologous genes into the host cells such that when a substrate is provided to the host cell the synthesis of the desired flavonoid is carried out in the host cell. The set of genes comprises genes encoding for the enzymes required for conversion of the particular substrate to the desired flavonoid.

Figure 1:
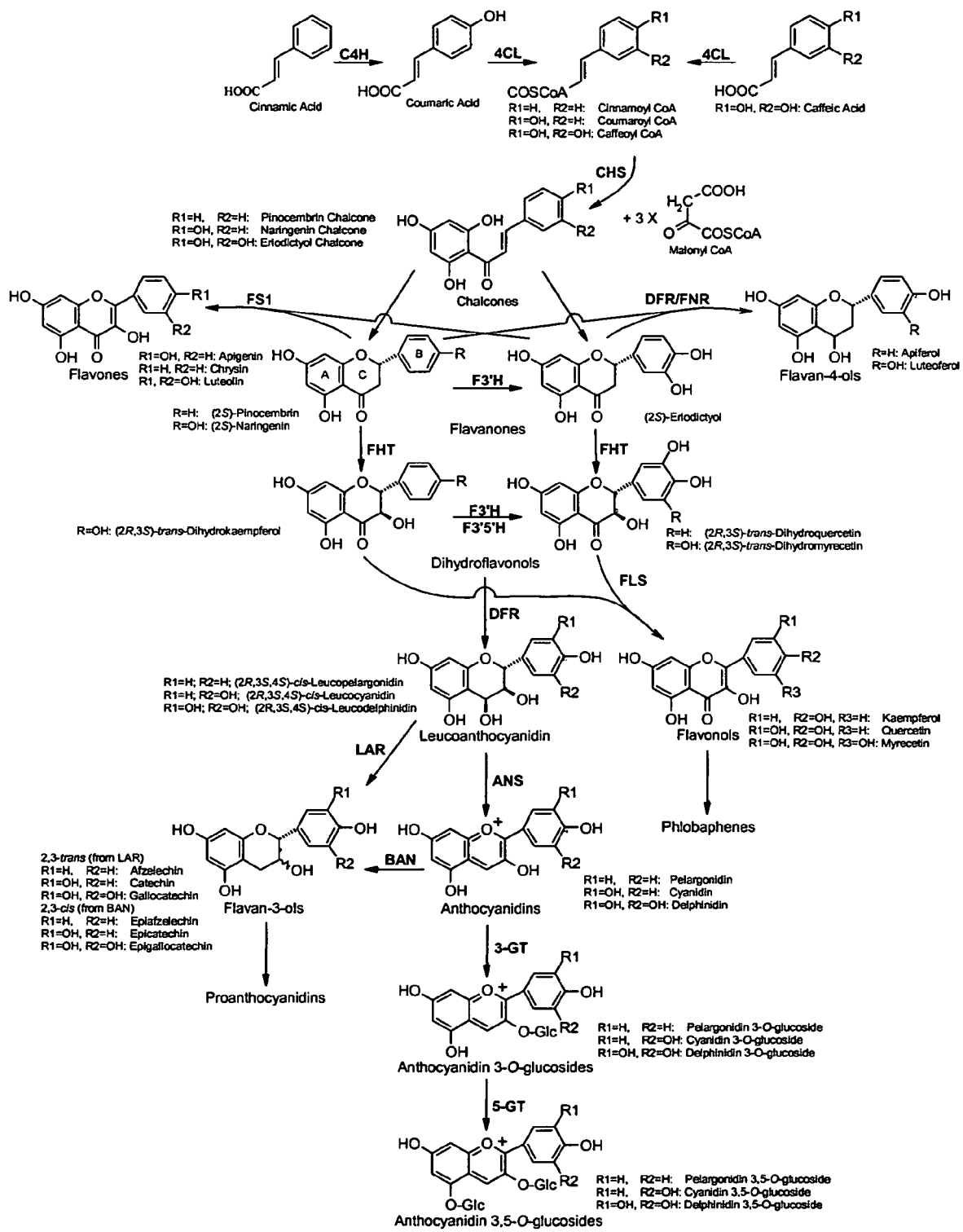
FIG. 1: Flavonoid biosynthetic pathway in plants. The following abbreviations are used: C4H, coumarate 4-hydroxylase; 4CL, 4-coumaroyl-CoA ligase, CHS, chalcone synthase; FSI, Flavone Synthase; CHI, chalcone isomerase; F3'H and FHT, flavanone 3-hydroxylase; F3'5'H, Flavonoid 3'5' hydroxylase; DFR, dihydroflavonol 4-reductase; FNR, flavanone reductase; FLS, flavonol synthase; LAR, Leucoanthocyanidin reductase; ANS, anthocyanidin synthase; 3-GT, UDP-glucose:flavonoid 3-O-glucosyltransferase;.

FIG. 1 shows the pathway for the biosynthesis of various flavonoids. The set of genes can be selected based upon the substrate to be provided to the host cell and upon the desired end product flavonoid.

The host cells most convenient for the production of flavonoids include bacteria and yeast. An example of bacterial cells suitable for this purpose is *Escherichia coli*. An example of yeast cells suitable for this invention is *Saccharomyces cerevisiae*.

Introducing a set of genes into a cell can be achieved using a variety of techniques known to those skilled in the art, such as by transformation of the cell with a vector which comprises more than one inserted gene or by transformation with multiple vectors that each comprise one or more inserted gene. In this regard, vectors which are capable of propagation in microorganisms and which are adapted for expressing more than one inserted gene can be prepared using standard molecular biological techniques or purchased commercially. Further, such vectors can be prepared for use in introducing a group of genes into a variety of microorganisms, such as bacteria or yeasts. The vectors may be a plasmid, phagemid, a phage, or a cosmid.

In one embodiment, a commercially available vector suitable for expressing more than one inserted gene can be prepared and used for transformation of bacteria. An example of a vector suitable for expressing more than one gene is the pRSFDuet™ vector, which is part of the Duet series of gene expression vectors (available from Novagen®). The pRSFDuet™ vector is designed to co-express two target proteins via the insertion of their respective coding sequences into two multiple cloning sites (MCS), each of which is driven by a T7 promoter. The pRSFDuet™ vector also carries kanamycin resistance marker, and can be transformed into the same cell with pETDuet™-1, pACYCDuet™-1, and/or pCDFDuet™-1, each of which carries an antibiotic resistance marker other than kanamycin resistance.

Thus, in one embodiment, a composition comprising one or more nucleic acids which encode a set of genes sufficient to direct the biosynthesis of plant specific flavonoids can be introduced into a cell using any one or a combination of the vectors, such as the Duet series of vectors, into which the genes have been inserted. It will also be recognized by those skilled in the art that preparations of vectors suitable for similar applications in eukaryotic microorganisms, such as in yeast cells, can be carried out using standard molecular biological techniques with appropriate adaptation of eukaryotic specific vector components, such as promoters, origins of replication and selectable markers.

Introducing a group of genes into a cell by transformation with an appropriate vector(s) can be achieved using well known techniques. For example, yeast can be transformed using the lithium acetate procedure or by electroporation, while transformation of bacteria can be achieved using techniques such as electroporation or by incubation of transformation competent cells with the vector(s) or by heat shock.

The set of genes for introduction into a host cell are selected depending upon the flavonoid to be synthesized and upon the substrate to be provided to the host cell. The substrate should be such that it is transported into the host cell. As an illustration, for the synthesis of anthocyanins from the phenylpropanoid malonyl CoA, the genes encoding the following enzymes would be introduced into the host cell: coumarate 4-hydroxylase (C4H), 4-coumaroyl-CoA ligase (4CL), Chalcone synthase (CHS), Chalcone isomerase (CHI), Flavonoid 3'5' hydroxylase (F3'5'H), Flavanone 3-hydroxylase (FHT), Dihydroflavonol 4-reductase (DFR), Anthocyanidin synthase (ANS) and UDP-glucose: flavonoid 3-O-glucosyltransferase (3-GT). If synthesis of flavonoids upstream of anthocyanin is desired, the enzyme that uses the desired flavonoid as a substrate can be eliminated from the cassette. For example, if the synthesis of only flavanones is required, only genes encoding for C4H, 4CL, CHS and CHI need be included in the cassette. If a flavan-3-ol is desired, a set of genes encoding for C4H, 4CL, CHS, CHI, F3H, FHT, DFR and Leucoanthocyanidin reductase (LAR) can be used. If a flavanol is desired, a set of genes encoding for C4H, 4CL, CHS, CHI, F3H, FHT and flavonol synthase (FLS) can be used. If a anthocyanadin is desired, the set of genes encoding for: C4H, 4CL, CHS, CHI, F3H, FHT, DFR and ANS can be used. From the general biosynthetic pathway shown in FIG. 1, the set of genes required for the synthesis of desired flavonoids can be identified and used as described herein. If the substrate provided to the host cells is different than a phenylpropanoid, the genes for enzymes upstream of the substrate need not be used. If a flavone is desired, a set of genes will include C4H, 4CL, CHS, CHI and Flavone Synthase I (FSI) or Flavone Synthase II (FSII). For example, if naringenin (flananone) will be used as a substrate, and the desired flavonoid to be synthesized is an anthocyanin, the set of genes required are FHT, F3'5'H, DFR, ANS and 3-GT.

If the substrate to be provided is cinnamic acid or p-coumaric acid, the set of enzymes can also include Coumarate 4-hydroxylase (C4H) and/or 4 coumaroyl-CoA ligase (4CL).

The genes for the particular enzymes can be obtained from different plan sources. Such plant sources include, but are not limited to, *Petroselinum crispum*, *Arabidopsis thaliana*, *Medicago sativa*, soybean, *Petunia*, *Petunia hybrida*, *Catharanthus roseus*, snapdragon, *Malus domestica*, *Lilium hybrida*, Carot, *Ipomoea purpurea*, *Ipomoea nil*, *Anthurium andraeanum*, strawberry, *Rosa hybrida*, *Dianthus gratianopolitanus* and *Desmodium uncinatum*.

In embodiment, the present invention provides compositions and methods for the production of dihydroflavanols, anthocyanidins and anthocyanins from a flavanone substrate in a microbial species through the heterologous expression of genes which encode for the enzymes involved in the conversion. In this embodiment, a method is provided for production of pelargonidin 3-O-glucoside from a microbial species through the heterologous expression of the genes encoding FHT (MdF3H) from *Malus domestica*, DFR (dfr) from *Dianthus gratianopolitanus* or *Anthurium andraeanum*, ANS (MdANS) from *Malus* domestica and 3-GT (PGT8) from *Petunia×hybrida*. We believe this is the first instance of an anthocyanin molecule being synthesized through microbial fermentation. The same set of enzymes can be used to provide another anthocyanin, cyanidin 3-O-glucoside, from the precursor flavanone eriodictyol and to provide another anthocyanin, myricetin 3-O-glucoside from the precursor flavanone pentahydroxyflavanone. Alternatively, the insertion of a fifth enzyme in the previous gene cluster, flavonoid 3'5'-hydroxylase, allows the conversion of the precursor flavanone naringenin to both cyanidin 3-O-glucoside and myricetin 3-O-glucoside.

In another embodiment the method further comprises introducing genes for the conversion of phenylproponoids to flavanones. The genes required for this portion of the pathway encode for the enzymes CH4, 4CL, CHS and CHI In another embodiment, the gene cluster includes genes encoding for the enzymes for the entire pathway from phenylpropanoids to various flavonoids including flavones, flavanones, flavan-4-ols, dihydroflavonols, flavonols, leucoanthocyanidins, flavan-3-ols, anthocyanidins and anthocyanins.

The present invention also provides compositions for production of dihydroflavanols, anthocyanidins and anthocyanins in microbial species. For example, in one embodiment is provided a set of genes that expresses the four genes of the lower anthocyanin biosynthesis pathway which converts the flavanone naringenin to one of the first stable, colored anthocyanins, namely pelargonidin 3-O-glucoside. In a one embodiment, a different promoter and ribosome binding site is used for each gene.

One criterion for gene selection and combination is the substrate specificity of the proteins produced. For instance, the structural gene for DFR from *Dianthus gratianopolitanus* results in the expression of an enzyme which is highly efficient with respect to the substrate dihydrokaempferol. However, other DFR genes which code for enzymes which have similar substrate specificity can be used as well, provided that the gene is expressed in the host. For example, the DFR gene from *Dianthus caryophyllus* may also be used based on the high degree of amino acid similarity in the substrate specificity region with the DFR from *Dianthus gratianopolitanus*. Similarly, different genes can be used from other sources in the biosynthetic pathway of the flavonoids.

In general, the gene for one member of each enzyme class (flavanone 3-hydroxylase, flavonoid 3'5'-hydroxylase, dihydroflavanol 4-reductase, anthocyanidin synthase and 3-O-glucosyltransferase may be from a variety of plant sources.

However, the genes should be expressible in the host cells and their products should have a substrate specificity which includes the product which is one step upstream in the conversion of flavanone to anthocyanin. The advantages of the present invention include the following: E. Coli/S. cerevisiae does not produce flavonoids in its natural (wild-type) form. As a result, a desired flavonoid can be produced by developing the right gene clusters (metabolic pathways) in E. Coli/S. cerevisiae in a very pure form-meaning with no other anthocyanin contamination. That advantage dramatically reduces the cost associated with flavonoid purification from plants. Another advantage is that E. coli/S. cerevisiae replicates fast and grows much better than plants. In that respect, a recombinant E. Coli/S. cerevisiae strain carrying the particular flavonoid biosynthesis pathway can produce more product than a plant. A yet another advantage is that microbial fermentation is the established way of producing chemicals in the biotech industry. There are several reasons for that, the main ones being that bacteria and yeast can grow very well in a control (fermentation) environment and their genetic toolbox in very well established. Therefore, this technology of producing flavonoids from recombinant microorganisms will be much more attractive to biotech industries than current technologies.

The invention is described further through the following examples which are intended to be illustrative and not limiting in any way.

EXAMPLE 1

This example describes the synthesis of anthocyanins by the expression of four plant derived genes in E. coli. The genes are involved in the lower anthocyanin biosynthetic pathway. An artificial gene cluster was constructed that contains the four genes of the lower anthocyanin biosynthesis pathway which converts the flavanone naringenin to one of the first colored and stable anthocyanins in this pathway, namely pelargonidin 3-O-glucoside. A set of genes encoding FHT (MdF3H) from *Malus domestica*, DFR (dfr) from *Dianthus gratianopolitanus* or *Anthurium andraeanum*, ANS (MdANS) from *Malus domestica* and 3-GT (PGT8) from *Petunia×hybrida* was used. We also demonstrate that naringenin, utilized as the starting substrate for the production of pelargonidin 3-O-glucoside, was efficiently transported into E. coli without significant toxic effects to the cell.

Material and Methods

Bacterial strains, plasmids and culture conditions. E. coli TOP10F, purchased from Invitrogen, was used for DNA manipulations while E. coli JM109 was used for shake-flask experiments. Plasmids pTrcHis2-TOPO (Invitrogen) and pK184 were used for cloning purposes. Callistephin chloride (pelargonidin 3-O-glucoside chloride) standard was purchased from ExtraSynthase (France).

DNA manipulations. All DNA manipulations were performed according to standard procedures. Restriction enzymes, Calf Intestine Alkaline Phosphatase, and T4 DNA ligase were purchased from New England Biolabs and Promega. All PCR and RT-PCR reactions were performed using Roche's Expand High Fidelity PCR system. MdF3H and MdANS cDNA from *Malus domestica* was a kind gift from Dr Chikako Honda (National Institute of Fruit and Tree Science, Japan), while *Diathus gratianopolitanus* cDNA was a kind gift from Dr Nobuhiro Kita (Kanagawa Institute of Agricultural Science, Japan). PGT8 cDNA from *Petunia× hybrida* was isolated in our lab based on DNA sequence already published (GenBank accession number AB027454). More specifically, the Qiagen RNeasy MiniKit was used for total RNA isolation from *Petunia×hybrida* corolla, while reverse transcription for the cDNA generation was performed using SuperScript II (Invitrogen). In all cases, after PCR or RT-PCR amplifications, the absence of undesired mutations introduced during PCR was verified by direct nucleotide sequencing.

Figure 2:
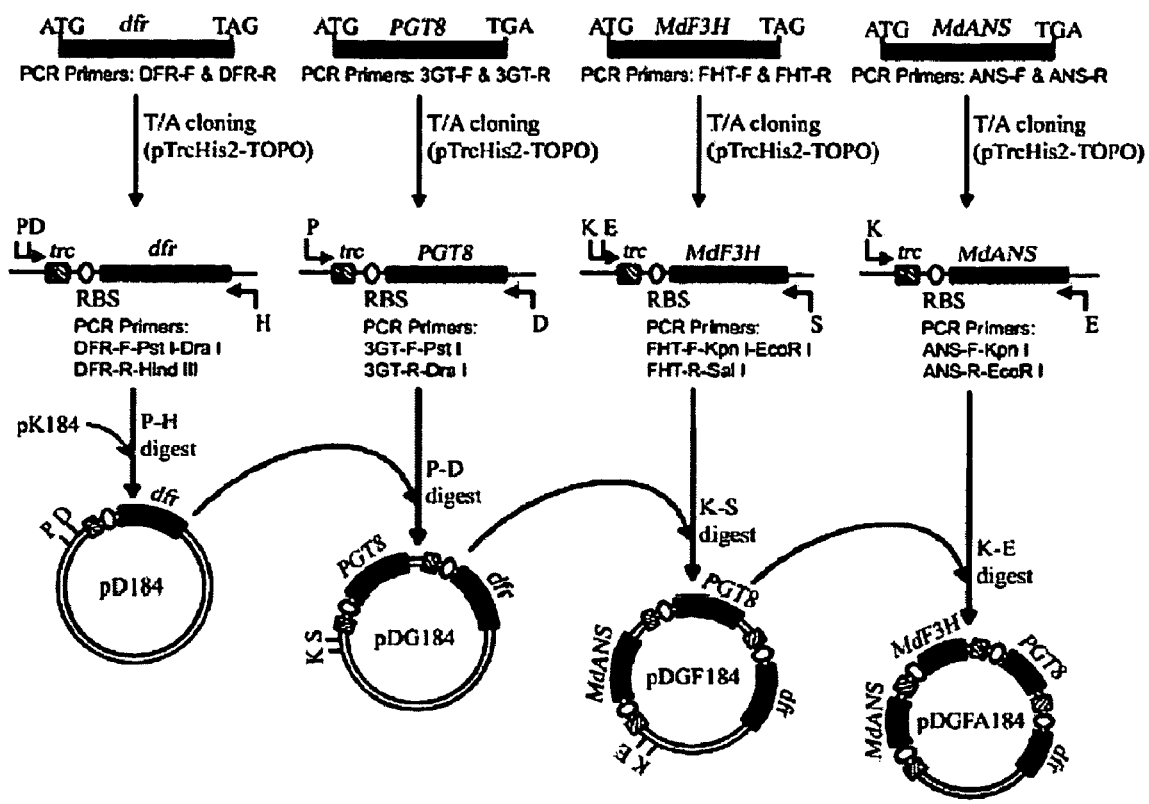
FIG. 2: Schematic representation of the strategy used for constructing vector pDGFA184. The following abbreviations are used for restriction enzymes: P, Pst I; H, Hind III; D, Dra I; S, Sal I; K, Kpn I; E, EcoR V. The trc promoter and the ribosome binding site (RBS) sequences are derived from vector pTrcHis2-TOPO.

Construction of plasmid pDGFA184. Plasmid pDGFA184 was constructed through two rounds of PCR for each one of the four genes cloned, as depicted in FIG. 2. In the first round of PCR, each of the four structural genes (from the start codon ATG to the stop codon) was isolated either from a plasmid provided or from total RNA, as previously described. After adding an A-overhang to the PCR products using Taq polymerase (Fisher Scientific), each structural gene was individually cloned under the strong trc promoter, by T/A cloning using pTrcHis2-TOPO as cloning vector. The trc promoter is a hybrid E. coli promoter, which is induced by isopropyl β-thiogalactosidase (IPTG).

In the second round of cloning, the dfr cDNA together with the trc promoter and the ribosome binding site (RBS) was first isolated by PCR, using a beginning primer hybridizing to a vector DNA region that lies upstream the trc promoter and an end primer hybridizing to the vector DNA region immediately after the stop codon. Two restriction sites, Pst I and Dra I were introduced in the beginning primer and a Hind III restriction site in the end primer. The resulting PCR fragment was digested with Pst I and Hind III and inserted into the low-copy number vector pK184 digested with the same enzymes, yielding plasmid pD184. Similarly, the PGT8 cDNA was isolated together with the trc promoter and ribosome-binding site using a beginning primer hybridizing upstream the trc promoter and carrying the restriction site Pst I while the end primer, designed immediately downstream from the stop codon, contained the restriction site Dra I. The amplified PCR fragment was digested with Pst I and Dra I and inserted into vector pD184 digested with the same enzymes. This resulted in the construction of vector pDG184. Next the MdF3H cDNA was isolated together with the trc promoter and the ribosome binding site with a beginning primer carrying restriction sites Kpn I and EcoR V and an end primer carrying restriction site Sal L The resulting PCR fragment was digested with Kpn I and Sal I and inserted into vector pDG184 digested with the same enzymes, resulting in vector pDGF184. Finally, the MdANS cDNA was isolated together with the trc promoter and ribosome binding site using a beginning primer carrying the restriction site Kpn I and an end primer carrying restriction site EcoR V. The resulting PCR fragment was digested with Kpn I and EcoR V and inserted into vector pDGF184 digested with the same enzymes. This resulted in the final vector pDGFA184. Table 1 contains all the PCR primer sequences used for the first and second rounds of PCR.

TABLE 1

| primer | Sequence (5'-3') | | Start codon | Stop codon |
|---|---|---|---|---|
| DFR-F | GATGGTTTCTAGTACAATTAACGAG - | (SEQ ID NO:1) | DFR | |
| DFR-R | *CTAA*GCAGATCCATTTTCATGATG - | (SEQ ID NO:2) | | DFR |
| 3GT-F | CATGACTACTTCTCAACTTCACATTGC - | (SEQ ID NO:3) | 3GT | |
| 3GT-R | *TCA*AGTAAGCTTGTGACATTTAACTAGCTC - | (SEQ ID NO:4) | | 3GT |
| F3H-F | ATGGCTCCTCCTGCTACTACGC - | (SEQ ID NO:5) | F3H | |
| F3H-R | *CTA*AGCAAATATGTCGTCCG - | (SEQ ID NO:6) | | F3H |
| ANS-F | ATGGTGAGCTCTGATTCAGTGA - | (SEQ ID NO:7) | ANS | |
| ANS-R | *TCA*CTTGGGGAGCAAAGCCTCT - | (SEQ ID NO:8) | | ANS |
| DFR-F-Pst I-Dra I | GGGG<u>CTGCAG</u>GGG<u>TTTAAA</u>CCGACATCATAACGGTTCTG - | (SEQ ID NO:9) | | |
| DFR-R-Hind III | CCCC<u>AAGCTT</u>CCC*CTAA*GCAGATCCATTTTCATGATGTTCTAGGG - | (SEQ ID NO:10) | | DFR |
| 3GT-F-Pst I | GGGG<u>CTGCAG</u>CCGACATCATAACGGTTCTG | (SEQ ID NO:11) | | |
| 3GT-R-Dra I | CCCC<u>TTTAAA</u>CCC*TCA*AGTAAGCTTGTGACATTTAACTAGCTG - | (SEQ ID NO: 12) | | 3GT |
| F3H-F-Kpn I-EcoRI | GGGG<u>GGTACC</u>GGG<u>GATATC</u>CCGACATCATAACGGTTCTG - | (SEQ ID NO:13) | | |
| F3H-R-Sal I | CCCC<u>GTCGAC</u>CCC*CTA*AGCAAATATGTCGTCCGCTGGC - | (SEQ ID NO:14) | | F3H |
| ANS-F-Kpn I | GGGG<u>GGTACC</u>CCGACATCATAACGGTTCTG - | (SEQ ID NO:15) | | |
| ANS-R-EcoR I | CCCC<u>GATATC</u>CCC*TCA*CTTGGGGAGCAAAGCCTCTT - | (SEQ ID NO:16) | | ANS |

[a]Underlining indicates restriction enzyme cleavage sites. Boldface indicates start codon and italics indicate stop codon.

Assay of ANS enzymatic activity. Recombinant *E. coli* TOP10F carrying MdANS cDNA cloned into the pTrcHis2-TOPO vector was grown, induced, and lysed as described in the previous section, except that ampicillin (100 µg/ml) was used for antibiotic selection. The standard mixture for the ANS reaction (200 µl) was prepared by mixing 10 µl of 15 mM cis- or trans-leucoanthocyanidin, 4 µl of 500 mM sodium ascorbate, 2 µl of 500 mM ferrous sulfate, and 2 µl of 500 mM 2-oxoglutaric acid with 100 to 500 µg of total protein preparation. The reaction mixture was incubated at 30° C. for 30 min, and the reaction was terminated by extraction with 400 µl ethyl acetate. The extract was dried by speed vacuum and then dissolved in 3 µl dimethyl sulfoxide-27 µl water-1 µl concentrated HCl. The products were analyzed by HPLC using an Agilent 1100 series instrument and a reverse-phase ZORBAX SB C18 column (4.6 by 150 mm) maintained at 25° C. The compounds produced were separated by elution with an acetonitrile water gradient, both containing 0.1% formic acid, at a flow rate of 1.0 ml/min. The HPLC conditions were as follows: 10 to 40% acetonitrile for 10 min and 40 to 10% acetonitrile for an additional 5 min. The A515 of pelargonidin and cyanidin was monitored. The retention times under these HPLC conditions for the standard authentic samples are as follows: Naringenin: 11.7; Eriodictyol: 10.7; cis-Dihydrokaempferol: 9.7; trans-Dihydrokaempferol: 10.1; cis-Dihydroquecertin: 8.3; trans-Dihydroquecertin: 8.4; Kaempferol: 11.9; Quecertin: 10.8; cis-leucocyanidin: 3.9; trans-leucocyanidin: 4.8; Pelargonidin: 7.8; Cyanidin: 6.7; Pelargonidin 3-O-glucoside (callistephin chloride): 5.1; Cyanidin 3-O-glucoside (kuromanin chloride): 4.4. Retention times were estimated according to the reverse-phase HPLC conditions described in this example Recombinant Protein Expression. *E. coli* JM109 harboring plasmid pDGFA184 or plasmid pK184 (control) was pre-inoculated in Luria-Bertani (LB) liquid medium (3 ml) containing 50 µg/ml kanamycin at 37° C. overnight with shaking. The following day, 1 ml of preinoculum was added to 200 ml LB liquid medium (also containing kanamycin 50 µg/ml) and the culture was left to grow at 37° C. with shaking until $OD_{600}$ reached approximately 0.6. At that point IPTG was added to the culture to a final concentration of 1 mM and the culture was incubated at room temperature (with shaking) for 5 hours. The cells were harvested by centrifugation, washed twice with Washing Buffer (0.9% NaCl) and resuspended in Sonication Buffer (phosphate 20 mM, NaCl 50 mM, dithiothreitol 1 mM, pH 7.0). Cell disruption was done by sonication and soluble protein was obtained by centrifugation. Total protein was estimated using the BCA assay (Pierce Chemicals) and analyzed by sodium dodecyl sulfate polyacrylamide gel electrophoresis (SDS-PAGE) according to standard procedures.

E. coli shake-flask experiments. The identification of compounds produced from recombinant E. coli strain JM109 carrying plasmid pDGFA184 was done in a similar way to what has already been described in the literature Hwang et al., 2003, Appl. Environ Microbiol., 69:2699-2706). More specifically, 3 ml of Luria-Broth rich medium containing 50 ug/ml kanamycin was inoculated with the recombinant strain and was incubated at 37° C. with vigorous shaking. The next day, 200 ml of LB containing 50 µg/ml kanamycin was inoculated with 1 ml of overnight culture and the culture was incubated at 37° C. with vigorous shaking at 300 rpm to an $OD_{600}$ of approximately 0.6. Next, the inducer IPTG was added to the culture to a final concentration of 1 mM. In order to avoid the formation of inclusion bodies, after the addition of the inducer the culture was incubated at room temperature with vigorous shaking overnight. Next day the cells were harvested by centrifugation and washed twice with M9 minimal medium. The pellets were then resuspended in 200 ml M9 minimal medium containing 50 µg/ml kanamycin, 1 mM IPTG and various concentrations of naringenin. In order to measure growth curves, the cultures were left to grow at room temperature with vigorous shaking until late stationary phase was reached. For flavonoid extraction experiments, the cultures were left to grow at room temperature for 65 h, again with horizontal vigorous shaking.

Flavonoid extraction. After the shake flask experiments had been completed the supernatant was separated from the cells by centrifugation. Flavonoids were extracted from the supernatant with an equal volume (approximately 200 ml) of either isoamyl alcohol or ethyl acetate for 2 h at room temperature. The organic layer was evaporated to dryness by lyophilization and the resulting orange powder was dissolved in 2 ml methanol. The compounds produced were separated by HPLC using a reverse phase YMC-ODS-A312 column (diameter, 6 mm 3×150 mm) with $CH_3OH$—$CH_3COOH$—$H_2O$ (20:15:65) as eluent at a flow rate of 1.0 ml/min at 40° C. Anthocyanins were detected and quantified by monitoring absorbance at 520 nm. The quantitative calibration curves were obtained with standard anthocyanin (callistephin chloride).

LC-MS. The LC-MS analysis was performed using a Thermo Finnigan LCQ Advantage and the same YMC-ODS-A312 column previously used for HPLC analysis. Dried fermentation extract or standard powder was first dissolved in methanol and then diluted with water containing 0.1% formic acid and 80% acetonitrile before injection to the LC/MS. Separation was performed using an acetonitrile-water gradient, both containing 0.1% formic acid, and a flow rate of 0.2 ml/min. The gradient program on the system was as following: 0-20 min, 11.75%-18.5% B; 20-25 min, 18.5%-20.75% B; 25-35 min, 20.75%-23% B; 35-42 min, 23% B; 42-43 min, 23%-50% B; 43-48 min, 50% B; 48-52 min, 50%-95% B; 52-109 min, 95% B; 109-110 min, 95%-11.75% B; 110-120 min, 11.75% B. MS/MS was run for m/z 433 at 35% relative energy. The samples were quantified using the fragment at m/z Results The Presence of Naringenin in the Medium Results in E. coli Growth Reduction.

Figure 3:
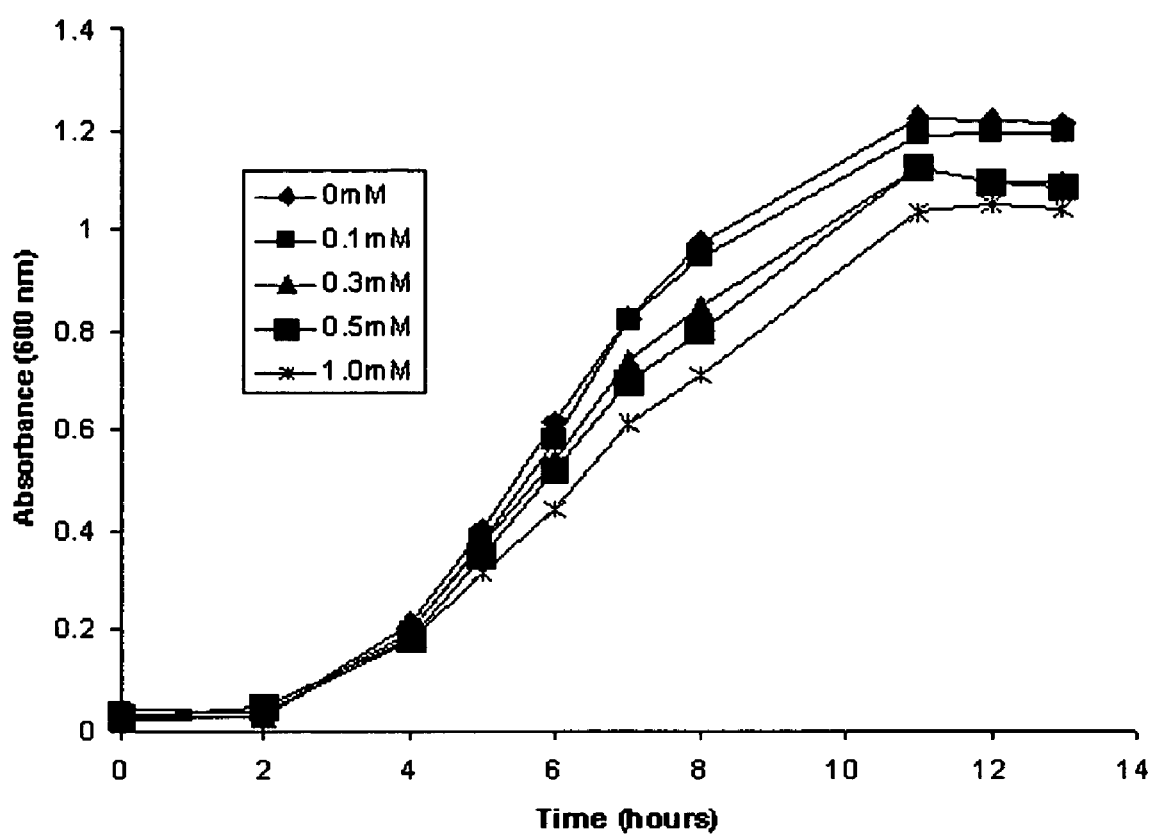
FIG. 3: Effect of different concentrations of naringenin on the growth profile of *E. coli* strain JM109 carrying empty vector pK184.

We tested the effect of naringenin on E. coli growth by incubating cultures of JM109 carrying plasmid pK184 in M9 minimal medium (50 µg/ml kanamycin) in the presence of different concentrations of naringenin (0.1 mM, 0.3 mM, 0.5 mM and 1 mM). As shown in FIG. 3, naringenin has an inhibitory effect on E. coli specific growth rates: the maximum specific growth rate dropped from 0.20 $h^{-1}$ for E. coli JM109 grown in M9 minimal medium with no naringenin, to 0.14 $h^{-1}$ for JM109 grown in the presence of 1 mM naringenin. A similar reduction was observed for the final cell mass: after 13 h of growth, $OD_{600}$ reached 1.2 for the control experiment (no naringenin), while $OD_{600}$ dropped to 1.0 for E. coli grown in the presence of 1 mM naringenin. This reduction in absorbance was also translated in decrease of the final dry cell weight concentration, which dropped from 0.586 mg/ml in the control (no naringenin) to 0.492 mg/ml in the presence of 1 mM naringenin in the minimal medium, both after 13 h cell growth. This 16% reduction in the final dry cell weight (also observed in the final absorbance) suggests that naringenin can enter E. coli probably by diffusion and it appears to have an inhibitory effect on cell growth.

Biochemical Characterization of M. domestica ANS.

ANS is a member of the nonheme ferrous and 2-oxoglutarate-dependent oxygenase family with wide substrate specificity. We performed the in vitro ANS assay using (2R,3S,4S)-cisleucocyanidin, (2R,3S,4R)-trans-leucocyanidin, (2R,3S,4S)-cis leucopelargonidin, and (2R,3S,4R)-trans-leucopelargonidin. All compounds were accepted as substrates, with the unnatural trans-leucoanthocyanidins catalyzed more efficiently than the natural cis epimers. HPLC analysis of the in vitro ANS reaction indicated that dihydroquercetin and quercetin (in the case of leucocyanidin as the substrate) or dihydrokaempferol and kaemferol (in the case of leucopelargonidin) were the major products; only 1% of the final ANS products corresponded to cyanidin or pelargonidin. The majority of the product, 82%, corresponded to dihydroflavonols (dihydrokaempferol or dihydroquercetin), while the rest corresponded to flavonols (kaempferol or quercetin). This result was consistent, regardless of the leucopelargonidin epimer used as a substrate. The observed product distributions from M. domestica ANS incubations are presented in Table 2. The reaction products were quantified by integrating peak area in the HPLC profiles and comparing them with standard curves of authentic samples. Cyanidin was monitored at 515 nm and querceptin at 360 nm, and dihydroquerceptin (DHQ) at 290 nm. Results shown are the averages of two independent experiments.

TABLE 2

| Substrate | % cis DHQ | % trans DHQ | % Cyanidin | % Querceptin |
|---|---|---|---|---|
| (2R,3S,4S)-cis LCD | 56 | 26 | 1 | 17 |
| (2R,3S,4S)-trans LCD | 40 | 42 | 1 | 17 |

Expression of the Anthocyanin Biosynthesis Pathway in E. coli.

All four genes were placed individually under the control of the strong trc promoter in the low copy number E. coli vector pK184. We chose a low copy number vector in order to avoid the likely high transcription and translation levels from higher copy number plasmids that might have deleterious effects to the cell. A ribosome binding site, AGAGG and a reinitiation ribosome binding site AAGGAG located after a minicistron sequence, both derived from cloning vector pTrcHis2-TOPO, were present 46 bp and 16 bp respectively from the start codon of each gene. Even though the same untranslated region was present in front of each one of the four genes, no recombination events were observed and the vectors proved stable in *E. coli* JM109 even in the absence of antibiotic in the medium and after 13 hours of growth.

For the purpose of assessing the expression levels of the recombinant proteins, we grew the recombinant *E. coli* cultures at sub-optimal (room) temperature in order to avoid inclusion body formation. When the total protein was analyzed on SDS-PAGE, an apparently increased level of protein production was evident in the region of 40 kDa (where ANS with a molecular weight of 40,470, DFR with a molecular weight of 39,417 and FHT with a molecular weight of 41,137 migrate) while protein expression was less evident in the region of 50 kDa (where 3-GT with a molecular weight of 49,706 migrates). No proteins of similar sizes on SDS-PAGE were observed for a control strain carrying the empty vector pK184. The recombinant proteins were also detected in the insoluble fraction (data not shown), providing evidence for the formation of inclusion bodies. This result is different from what has been reported previously for the flavanone biosynthetic pathway heterologously expressed in *E. coli* (Hwang et al., 2003, (Hwang et al., 2003, *Appl. Environ. Microbiol.* 69: 2699-1706), where recombinant protein expression was not evident for all the heterologous enzymes.

Analysis of fermentation products. After the shake flask cultures were harvested, the culture broth and the cells were separated by centrifugation and various polyphenolic compounds were extracted from the fermentation broth using isoamyl alcohol or ethyl acetate.

Figure 4:
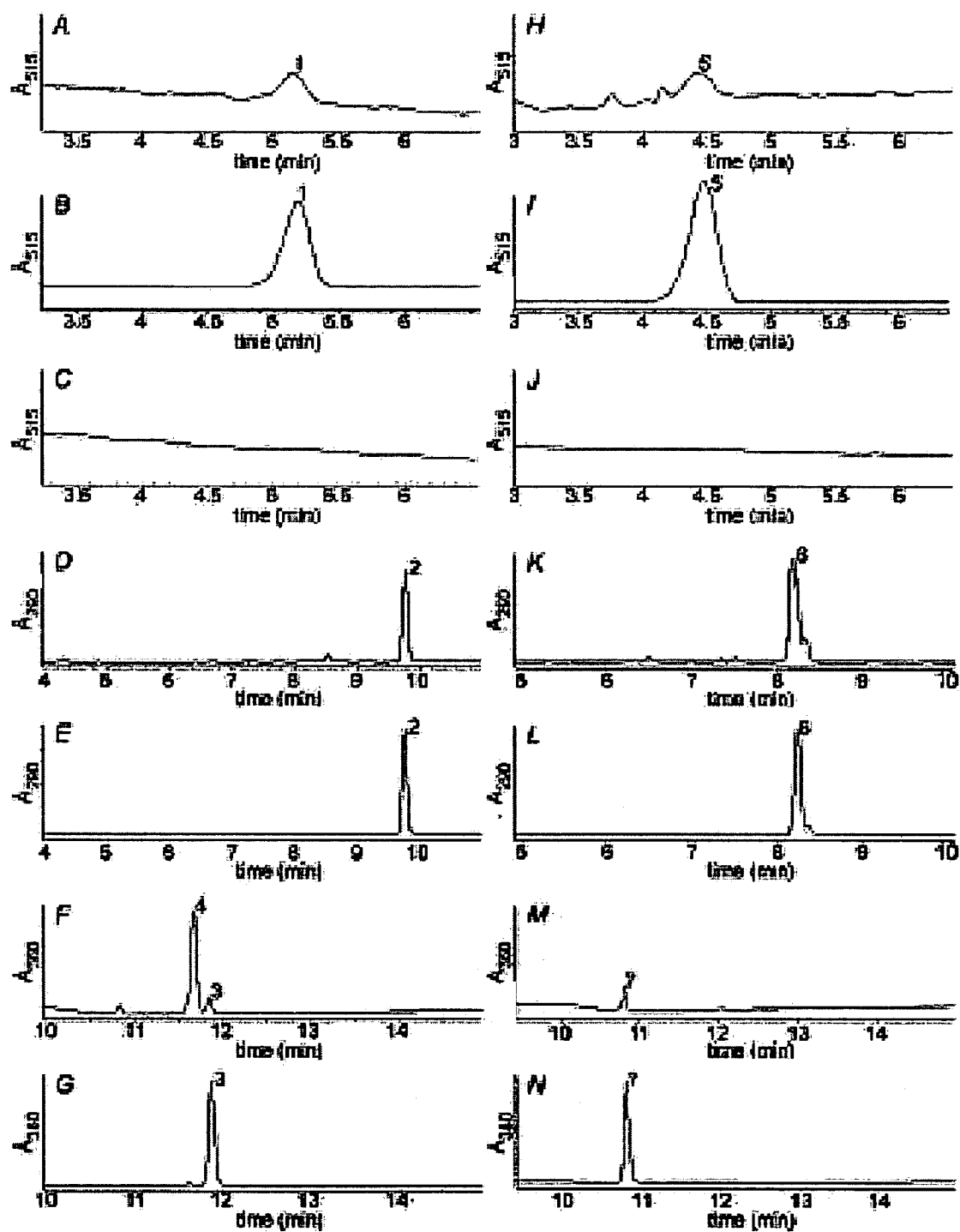
FIG. 4: HPLC analysis of shake flask supernatants of recombinant JM109 carrying plasmid pDGFA184 performed as described in Materials and Methods. A, pelargonidin 3-O-glucoside (peak 1) produced from the recombinant strain when fed with naringenin; B, standard callistephin chloride (peak 1); C, shake flask supernatant of JM109 carrying empty vector pK184 fed with naringenin (control); D, dihydrokaempferol (peak 2) produced from the recombinant strain when fed with naringenin; E, standard dihydrokaempferol (peak 2); F, side product kaempferol (peak 3) produced from the recombinant strain fed with naringenin; remaining starting material naringenin (peak 4) is shown; G, standard kaempferol (peak 3); H, cyanidin 3-O-glucoside (peak 5) produced from the recombinant strain fed with eriodictyol; I, standard kuromanin chloride (peak 5); J, shake flask supernatant of JM109 carrying empty vector pK184 fed with eriodictyol (control); K, dihydroquercetin (peak 6) produced from the recombinant strain fed with eriodictyol; L, standard dihydroquercetin (peak 6); M, side product quercetin (peak 7) produced by the recombinant strain fed with eriodictyol; N, standard quercetin (peak 7)

We first performed HPLC analysis of the fermentation broth, obtained both from the recombinant and control cultures. For detection, we monitored absorbance at 520 nm (FIG. 4). Only one compound appeared to be present, with the same retention time as the standard sample of callistephin chloride. The compounds were further analyzed using LC-MS.

Figure 5:
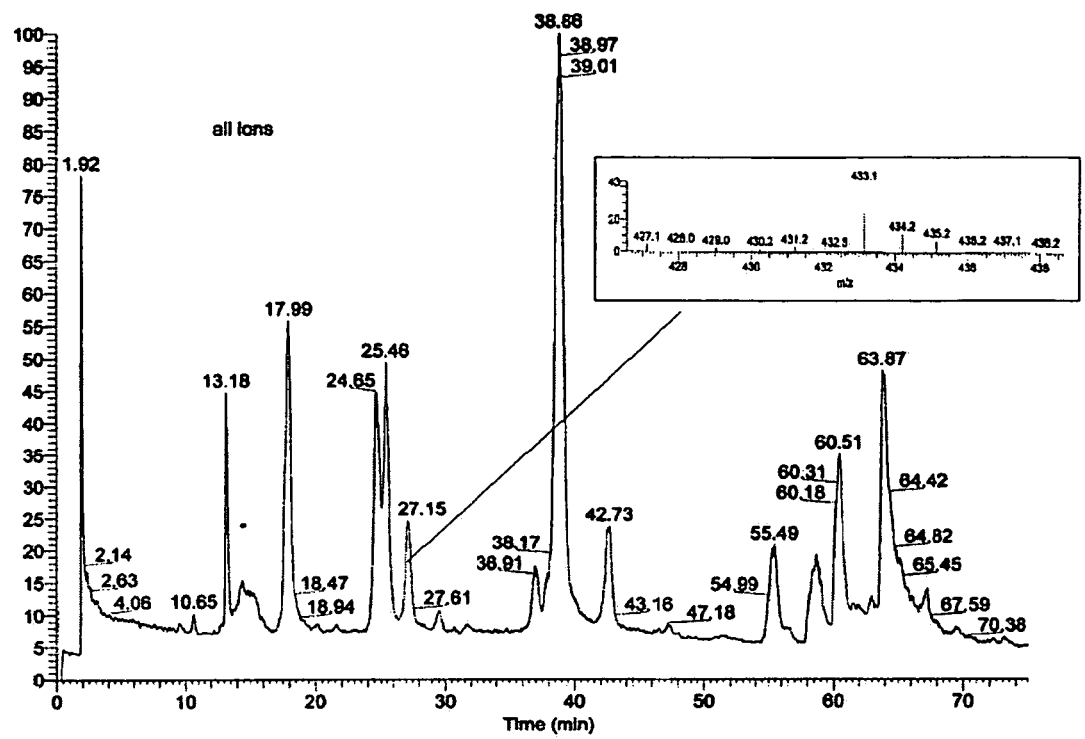
FIG. 5: Ion chromatographs of the compounds produced by *E. coli* JM109 harboring pDGFA184 (top) and standard callistephin chloride (bottom).
Figure 5:
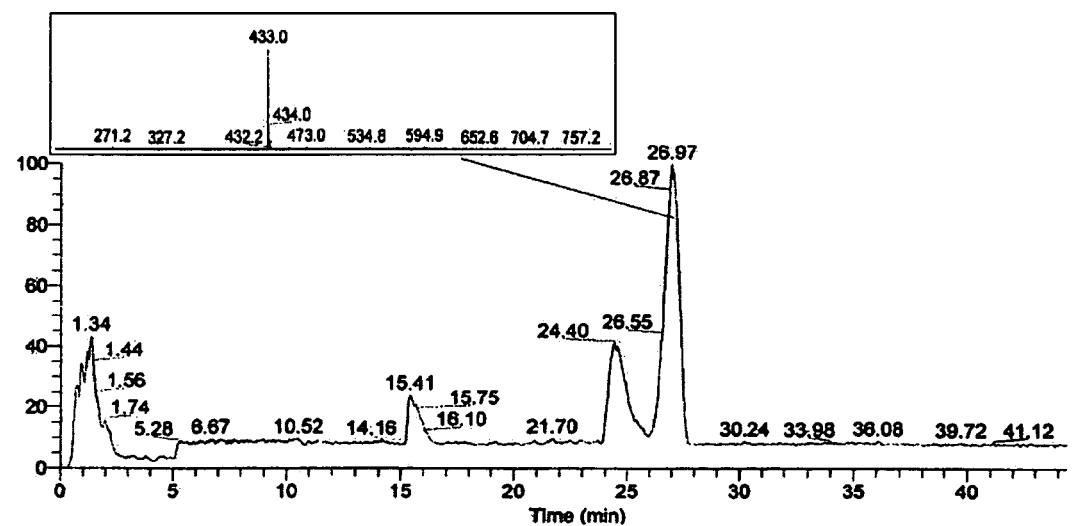

A total ion chromatograph was obtained for a sample of the standard callistephin chloride dissolved in methanol (FIG. 5). A major peak with m/z ratio of 433, the molecular weight of pelargonidin 3-O-glucoside, was obtained with a retention time of 26.97 min. A peak with the same retention time and m/z ratio was obtained in the total ion chromatograph of the fermentation extract, also dissolved in methanol. Spiking of callistephin standards of various concentrations in the fermentation extract and MS/MS analysis of the 433 ions at 35% relative energy gave us a pelargonidin-3-O-glucoside concentration of 9.8 µg/l, (extraction using isoamyl alcohol) and a concentration of 3.1 µg/l (extraction using ethyl acetate).

The HPLC and LC-MS results indicate that pelargonidin 3-O-glucoside was successfully produced through the heterologous expression of plant enzymes in *E. coli*.

EXAMPLE 2

In this example, we demonstrate the biosynthesis of plant specific flavonols from a bacterial species for the first time. This was achieved through the expression of gene clusters from heterologous plant sources in *E. coli* that allow the biosynthesis of flavanone precursor metabolites without the need of a chemical conversion. Using these gene clusters, the biosynthesis of the flavanone eriodictyol from *E. coli*. was also achieved.

Materials and Methods

Plant material, bacterial strains, plasmids and culture conditions. Parsley seeds were purchased from Stokes Seeds (Buffalo, N.Y.) while petunia plants were purchased from local nurseries. *E. coli* TOP10 (Invitrogen, Carlsbad, Calif.) was used for DNA manipulations while *E. coli* BL21Star (Promega) was used for shake-flask experiments. Plasmids pETDuet-1, pCDFDuet-1 and pRSFDuet-1 (Novagen) were used for cloning purposes.

Chemicals. Cinnamic acid, p-coumaric acid and caffeic acid were purchased from MP Biomedicals Inc. (Irvine, Calif.). Naringenin was purchased from Sigma-Aldrich (St. Louis, Mo.). Eriodictyol, dihydroquercetin, kaempferol and quercetin were purchased from Indofine (Hillsborough, N.J.).

DNA manipulation. All DNA manipulations were performed according to standard procedures (Sambrook et al. 1989, *Molecular cloning: a laboratory manual*, 2nd ed. Cold Spring Harbor Laboratory Press, New York, N.Y.). Restriction enzymes, Calf Intestine Alkaline Phosphatase, and T4 DNA ligase were purchased from New England Biolabs and Promega. Reverse Transcription Polymerase Chain Reactions (RT-PCR) were performed by using the Superscript One-Step kit from Invitrogen. PCR reactions were performed using Roche's Expand High Fidelity PCR system. MdF3H cDNA from *Malus domestica* was a kind gift from Dr Chikako Honda (National Institute of Fruit and Tree Science, Japan). FLS1 cDNA from *Arabidopsis thaliana* was isolated by high-fidelity PCR from EST clone RAFL09-32-C09, identified through homology search performed at The Institute for Genomic Research *A. thaliana* database (www.tigr.org/tdb/e2k1/ath1) and purchased from RIKEN BioResource Center (Tsukuba, Japan). CHI-A and chs cDNA from *Petunia×hybrida* and Pc4cL-2 from *Petroselinum crispum* were amplified based on DNA sequences available in GenBank (accession numbers AF233638 for chs, X14589 for CHI-A and X13325 for Pc4cL-2). More specifically, the Qiagen RNeasy MiniKit was used for total RNA isolation from *P.×hybrida* corolla or *P. crispum* young leaves. All primer sequences used are presented in Table 3. In all cases, the absence of undesired mutations introduced during PCR was verified by direct nucleotide sequencing.

TABLE 3

| Primer | Sequence (5'-3')[a] | |
|---|---|---|
| Pc4cL2-F | GGGGGGG<u>GATATC</u>GGATGGGAGACTGTG TAGCACCCAAAG | (SEQ ID NO:17) |
| Pc4cL2-R | CCCCCC<u>GGTACC</u>CCTTATTTGGGAAGA TCACCGGATGCT | (SEQ ID NO:18) |
| CHS-F | GGGG<u>GGATCC</u>GGATGGTGACAGTCGAG GAGTATCGTA | (SEQ ID NO:19) |
| CHS-R | CCCCC<u>TGCAG</u>CCTTAAGTAGCAACACT GTGGAGGACA | (SEQ ID NO:20) |
| CHI-A-F | GGGG<u>GATATC</u>GGATGTCTCCTCCAGTG TCCGTTACTA | (SEQ ID NO:21) |
| CHI-B-R | CCCC<u>GGTACC</u>CCCTAGACTCCAATCAC TGGAATAGTAG | (SEQ ID NO:22) |
| F3H-F | GGGGGG<u>GGATCC</u>GGATGGCTCCTCCTG CTACTACGCTGA | (SEQ ID NO:23) |
| F3H-R | CCCCCC<u>GTCGAC</u>CCCTAAGCAAATATG TCGTCCGCTGGC | (SEQ ID NO:24) |

TABLE 3-continued

| Primer | Sequence (5'-3')[a] |
|---|---|
| FLS-F | GGGGGG<u>GATATC</u>ATGGAGGTCGAAAGA (SEQ ID NO:25) GTCCAAGAC |
| FLS-R | CCCCCC<u>GGTACC</u>T*CAATCCAGAGGAAG* (SEQ ID NO:26) TTTATTGAGCTTGCGG |

[a]Underlining indicates restriction enzyme cleavage sites. Boldface indicates start codon and italics indicate stop codon Construction of plasmids. Plasmid pCDF-PC4CL2 containing Pc4cL-2 cDNA under the T7 promoter was constructed by subcloning Pc4cL2 between EcoR V and Kpn I in vector pCDFDuet-1. Plasmid pET-CHS-CHI harboring CHI-A and chs, each under the T7 promoter, was constructed by subcloning chs between EcoR V and Kpn I and CHI-A between BamH I and Pst I sequentially in vector pETDuet-1. Plasmid pRSF-FLS1-F3H carrying FLS1 and MdF3H, each under the T7 promoter was constructed by subcloning FLS1 between EcoR V and Kpn I and MdF3H between BamH I and Sal I sequentially in vector pRSFDuet-1. The overall cloning strategy is outlined in FIG. 6.

Growth Curves. In order to investigate the effect of Phenylpropanoid acids on *E. coli* growth, *E. coli* BL21Star was inoculated in 3 ml M9 liquid minimum medium and was left to grow at 37° C. overnight (preinoculum). The following day, 1 ml from the preinoculum was transferred to either 50 ml M9 minimal or Luria-Bertani (LB) rich liquid medium and p-coumaric acid, caffeic acid or cinnamic acid were added in the culture at different final concentrations (0 mM, 0.2 mM, 0.5 mM, 1 mM and 2 mM). Cell growth was monitored by measuring the absorbance at 600 nm ($A_{600}$).

Shake flask cultures. Recombinant *E. coli* BL21Star harboring plasmids pCDF-PC4CL2, pET-CHS-CHI and pRSF-FLS1-F3H or the control strain carrying empty vectors pCDFDuet-1, pETDuet-1 and pRSFDuet-1, were pre-inoculated in LB liquid medium (3 ml) containing 30 μg/ml kanamycin, 50 μg/ml ampicillin and 50 μg/ml streptomycin and were grown at 37° C. overnight with shaking. The following day, 1 ml of preinoculum was added to 50 ml LB or M9 liquid medium (also containing the same concentration of the three antibiotics) and the culture was left to grow at 37° C. with shaking until $A_{600}$ reached approximately 0.6. At that point the inducer isopropyl β-thiogalactoside (IPTG) was added to the culture to a final concentration of 1 mM and the culture was incubated at 30° C. for another 3 hours. The precursor substrate was then added to the culture to a final concentration of 0.20 mM (cinnamic acid, p-coumaric acid, caffeic acid) or 0.25 mM (pinocembrin, naringenin, eriodictyol) and the culture was left to grow at 30° C. for 65 hours with vigorous shaking.

Flavonoid extraction. After completion of the shake flask experiments, flavonoids were extracted directly from the culture broth with an equal volume (approximately 50 ml) of ethyl acetate for 30 seconds at room temperature with vigorous shaking. After centrifugation at 1,800×g for 20 mins, the organic layer was collected and evaporated to dryness by rotary evaporation and the resulting powder was dissolved in 0.1 ml of dimethyl sulfoxide (DMSO). Finally, water was added to a final volume of 1 ml.

HPLC analysis. Flavonoids and Phenylpropanoid acids were analyzed by High Performance Liquid Chromatography (HPLC), using an Agilent 1100 series instrument and a reverse phase ZORBAX SB-C18 column (4.6×150 mm) maintained at 25° C. The compounds were separated by elution with an acetonitrile/water gradient, at a flow rate of 1.0 ml/min. The HPLC conditions were as follows: 10 to 40% for 10 min, 40 to 60% for 5 min and 60 to 10% for 2 min. The retention times under these conditions for the standard authentic samples are as follows: Pinocembrin—16.36; Naringenin—12.819; Eriodictyol—11.084; Dihydrokaempferol—0.702; Dihydroquecertin—8.172; Kaempferol—13.061; and Quecertin—11.278. Flavanones and dihydroflavonols were detected and quantified by monitoring absorbance at 290 nm. Kaempferol and quercetin were detected and quantified at 360 nm. Calibration curves were obtained with authentic flavanone, dihydroflavonol and flavonol solutions of various concentrations.

Results

Figure 7:
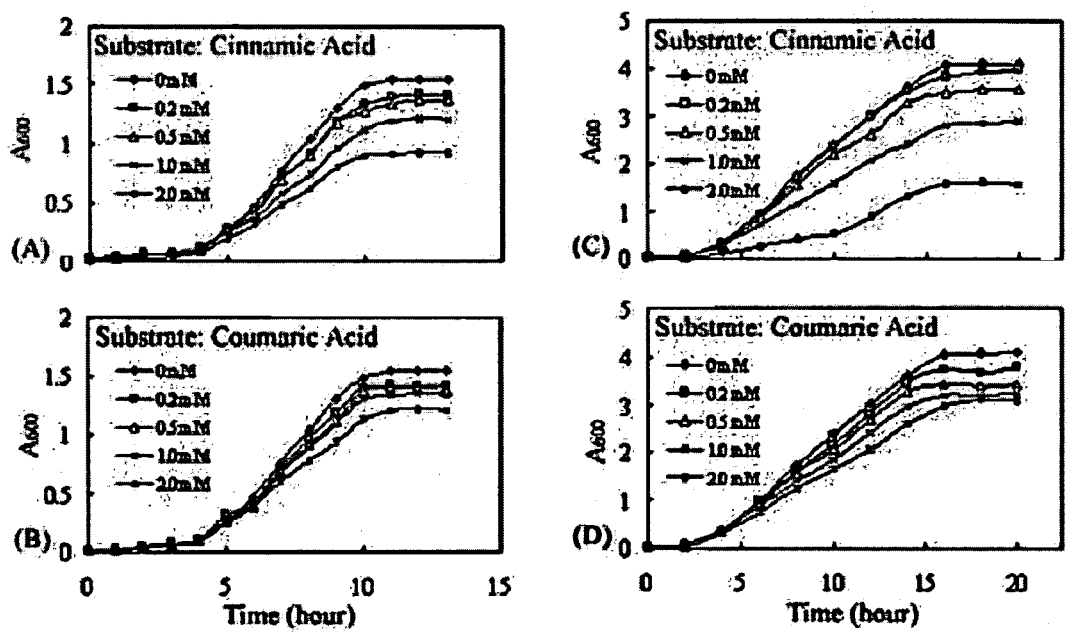
FIG. 7: Effect of different concentrations of cinnamic acid and p-coumaric acid on the growth profile of E. coli. (A) BL21* grown in M9 minimal medium and in the presence of various cinnamic acid concentrations. (B) BL21* grown in M9 minimal medium and in the presence of various p-coumaric acid concentrations. (C) BL21* grown in LB minimal medium and in the presence of various cinnamic acid concentrations. (D) BL21* grown in LB rich medium and in the presence of various p-coumaric acid concentrations.
Figure 8:
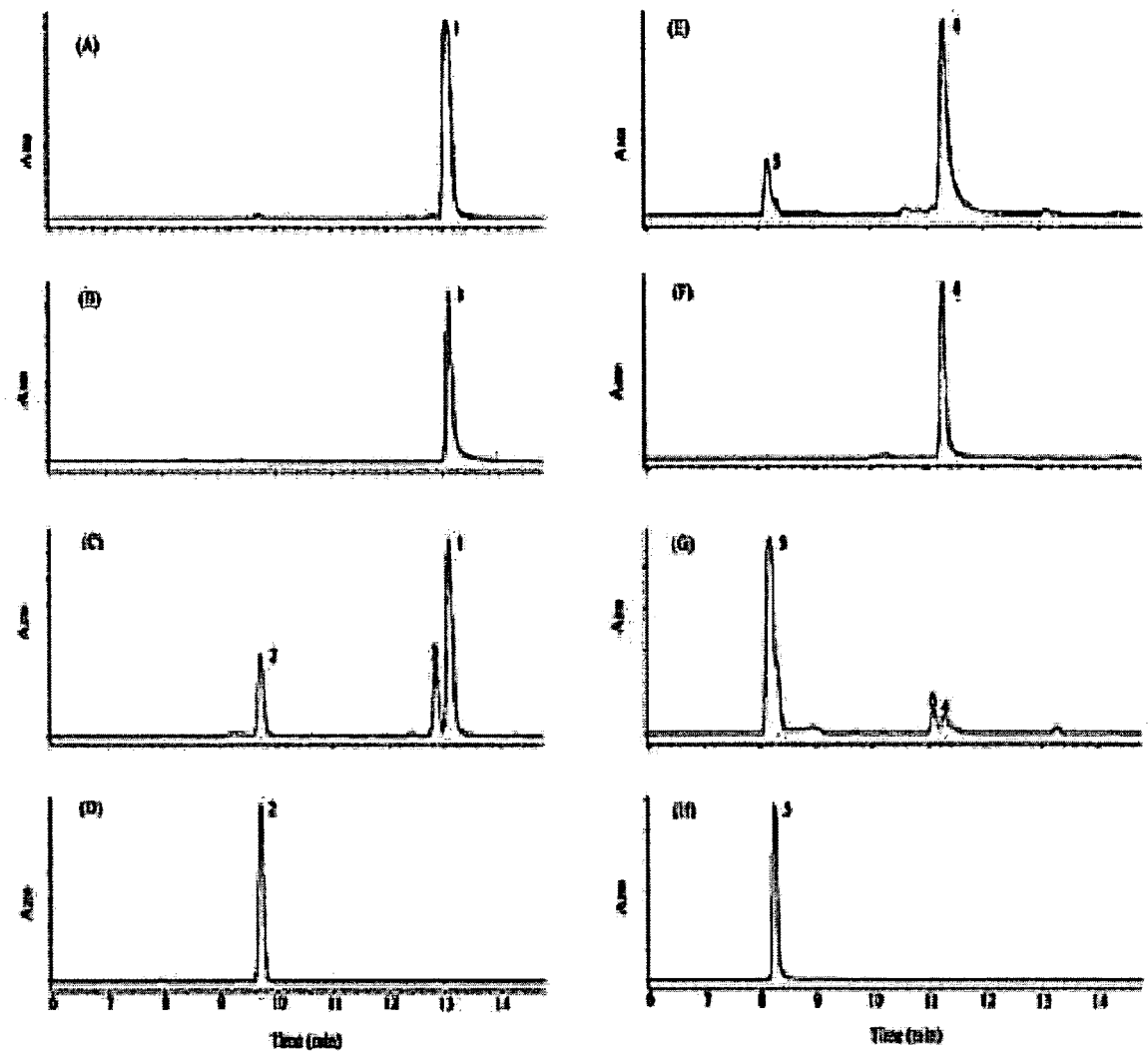
FIG. 8: HPLC analysis of shake flask supernatants of recombinant BL21* carrying plasmid pRSF-FLS1-F3H. (A), kaempferol (1), produced from the recombinant strain when fed with naringenin; (B), standard kaempferol (1); (C), dihydrokaempferol (3), produced from the recombinant strain when fed with naringenin (3); (1), standard dihydrokaempferol (2); (E), quercetin (4>, and dihydroquercetin (5) produced from the recombinant strain when fed with eriodictyol; (F), standard quercetin (4); (G), dihydroquercetin (5), produced from the recombinant strain when fed with eriodictyol (6); (H), standard dihydroquercetin (5).

Phenylpropanoid acids reduce *E. coli* growth. We tested the effect of both p-coumaric acid and cinnamic acid on *E. coli* growth by incubating BL21Star in M9 minimum medium and LB rich medium in the presence of different concentration of these compounds (0 mM, 0.05 mM, 0.1 mM, 0.15 mM, 0.2 mM, 1 mM, and 2 mM). As shown in FIG. 7, increased concentrations of phenylpropanoid acids resulted in *E. coli* growth inhibition. For example, in the case of p-coumaric acid in M9 rich medium, the growth rate dropped from 0.28 $h^{-1}$ (control, 0 mM) to 0.18 $h^{-1}$ (2 mM). Similarly, for cinnamic acid the growth rate dropped from 0.27 $h^{-1}$ (control, 0 mM) to 0.17 $h^{-1}$ (2 mM) in M9 minimal medium. These results indicate that *E. coli* growth is inhibited in the presence of flavanones.

Figure 6:
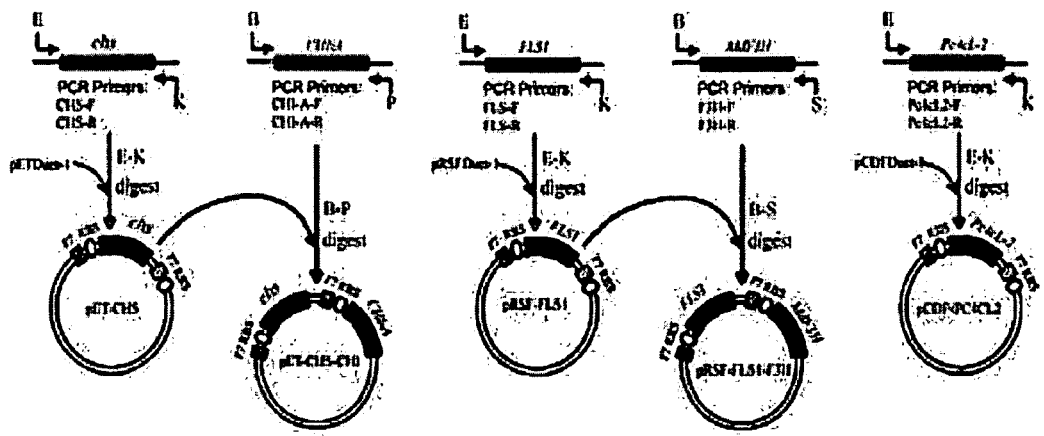
FIG. 6: Schematic representation of the strategy used for constructing vectors pCDF-PC4CL2, pET-CHS-CHI and pRSF-FLS1-F3H. The following abbreviations are used for restriction enzymes: E, EcoR V; K, Kpn I; B, BamH I; P, Pst I, S, Sal I. PCR and RT-PCR primer sequences used are presented in Table 4.

Exploring flavonol biosynthesis in *E. coli*. We accomplished the biosynthesis of flavonols in *E. coli* by first designing a gene cluster in vector pRSFDuet-1 that would allow flavanones, such as the monohydroxylated naringenin, dihydroxylated eriodictyol, and unhydroxylated pinocembrin to be converted to their respective flavonols, kaempferol, quercetin and galangin. The pRSFDuet-1 vector is a high copy number *E. coli* vector (above 100) that is based on the RSF1030 replicon and it encodes two separate multiple cloning sites (MCS) each of which is preceded by a T7 promoter. The cDNA for MdF3H encoding for FHT from *Malus domestica* (Honda et al., 2002, *Plant Physiol Biochem* 40 (11), 955-962) was inserted in the first MCS and the cDNA for FLS1, encoding for FLS from *Arabidopsis thaliana* (Pelletier et al., 1997, Plant Physiol 113 (4), 1437-1445) was inserted in the second (FIG. 6).

Shake flask cultures were first carried out in M9 minimal medium supplemented with the flavanones pinocembrin, naringenin or eriodictyol at a final concentration of 0.25 mM. The various polyphenolic compounds produced after 65 h cultivation period were extracted from the fermentation broth using ethyl acetate and were identified by retention time and UV absorption spectra. Approximately 90% of naringenin was consumed and was converted to the corresponding flavonol kaempferol (45 mg/lt) and dihydroflavonol dihydrokaempferol (15 mg/lt) (FIG. 8A, 8B, 8C, 8D). When eriodictyol was used as a substrate, the flavonol quercetin was produced at a concentration of 20.1 mg/lt while the intermediate dihydroflavonol dihydroquercetin accumulated at a concentration of 44 mg/lt (FIGS. 8E, 8F, 8G, 8H). Finally, the unhydroxylated flavanone pinocembrin was not converted to its corresponding dihydrohyflavonol (pinobanksin) or flavonol (galangin), providing direct evidence that the presence of at least one hydroxyl group on the B aromatic ring is necessary in order for bioconversion to occur.

We also tested flavonol production in LB rich medium. Contrary to our expectations, a significant reduction in the amounts of flavonols and dihydroflavonols produced was observed. In the case of naringenin, the concentration of kaempferol in the medium dropped to 4.83 mg/lt and the concentration of the intermediate dihydrokaempferol dropped to 10.85 mg/lt. In the case of eriodictyol, the concentration of quercetin produced dropped to 2.31 mg/lt while the concentration of accumulated dihydroquercetin dropped to 18.77 mg/lt. It is therefore very likely that LB contains molecules that inhibit FHT, FLS or both.

For the shake flask experiments, cultures were grown in either M9 minimal medium with glucose as carbon source or LB rich medium, and were fed with flavanone precursors (naringenin or eriodictyol). Dihydrokaempferol and kaempferol are the dihydroflavonol and flavonol compounds formed when naringenin is used as the starting flavanone. Dihydroquercetin and quercetin are the dihydroflavonol and flavonol compounds formed when eriodictyol is used as the starting flavanone. Values presented are the averages obtained from two independent experiments. The results of production of plant-specific dihydroflavonols and flavonols by recombinant *E. coli* BL21Star harboring plasmid pRSF-FLS1-F3H are summarized in Table 4.

TABLE 4

| Flavanone | Production (mg/liter) in M9 | | Production mg/liter in LB | |
|---|---|---|---|---|
| | Dihydroflavonol | Flavonol | Dihydroflavonol | Flavonol |
| Naringenin | 15 | 45.1 | 10.85 | 4.83 |
| Eriodictyol | 44 | 20.1 | 18.77 | 2.31 |

Engineering the Flavonol Biosynthesis from Precursor Phenylpropanoid Acids

In an effort to engineer the biosynthesis of flavonols directly from their precursor phenylpropanoid acids without the need for a step of chemical conversion, we used the following strategy.

Three genes of heterologous plant origins, namely Pc4cL-2 encoding for 4-coumarate:coenzyme A ligase (4CL) from *Petroselinum crispum* (parsley) (Lozoya et al., 1988. *Eur J Biochem* 176 (3), 661-667), CHI-A encoding for CHI from *Petunia* Vantunen et al., 1989, *Plant Mol Biol* 12 (5), 539-551; Vantunen et al., 1988, *EMBO J.*, 7 (5), 1257-1263) and chs encoding for CHS also from *Petunia* were isolated and cloned into the *E. coli* vectors pCDF-Duet-1 (Pc4cL-2) and pETDuet-1 (CHI-A and chs) (FIG. 6). Vector pCDFDuet-1 is based on the CloDF13 *E. coli* replicon, has a copy number of 20-40 and uses the aadA gene encoding for streptomycin resistance as a selection marker. Vector pETDuet-1 is a medium copy number vector (~40) based on the ColE1 replicon that uses the bla gene encoding for ampicillin resistance as a selection marker. Both vectors can co-replicate with each other and together with the pRSFDuet-1 vector (kanamycin resistance) previously used for the MdF3H and FLS1 cloning. Each gene was placed individually under a strong T7 promoter and ribosome binding site, generating vectors pCDF-PC4CL2 and pET-CHS-CHI that were cotransformed with plasmid pRSF-FLS1-F3H into *E. coli* strain BL21Star. Due to different antibiotic resistances and compatible replicons, all three recombinant plasmids could be selected and co-exist in *E. coli* cells.

Figure 9:
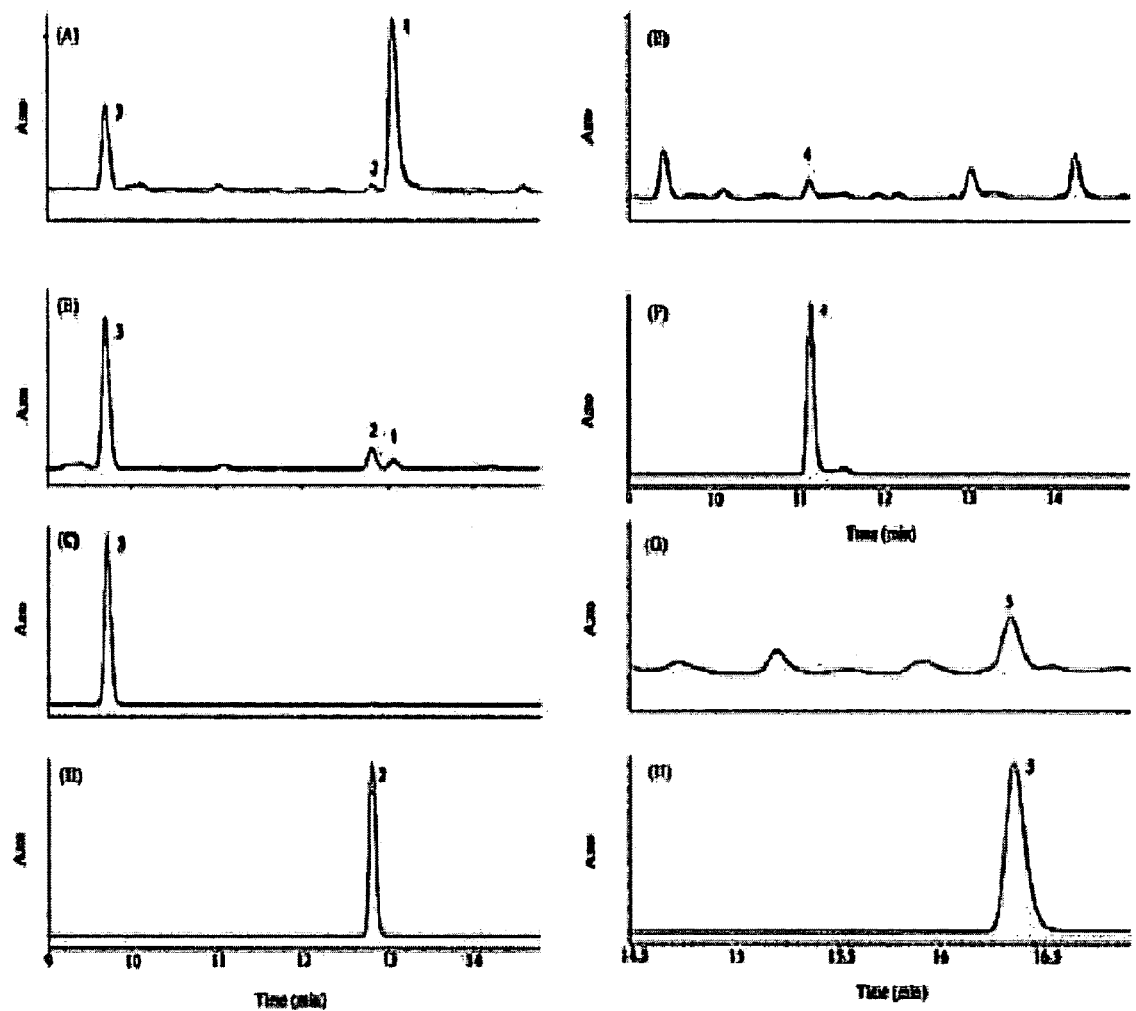
FIG. 9: HPLC analysis of shake flask supernatants of recombinant BL21* carrying plasmids pRSF-FLS1-F3H, pET-CHS-CHI and pCDF-PC4CL2 and performed. (A), kaempferol (1), produced from the recombinant strain when fed with p-coumaric acid; (B), naringenin (2), and dihydrokaempferol (3) produced from the recombinant strain when fed with p-coumaric acid; (C), standard dihydrokaempferol (3); (D), standard naringenin (2); (E), eriodictyol (4) produced from the recombinant strain when fed with caffeic acid; (F), standard eriodictyol (4); (G), pinocembrin (5), produced from the recombinant strain when fed with cinnamic acid; (H), standard pinocembrin (5).

Flavonol biosynthesis was first performed by culturing the recombinant BL21Star strain in M9 minimal medium with glucose as carbon source. Phenylpropanoid acids were added to the culture to a final concentration of 0.20 mM. Flavonoid compounds were extracted and identified as described above. When p-coumaric acid was used as a precursor metabolite, the compounds produced were naringenin (0.074 mg/lt), dihydrokaempferol (0.643 mg/lt) and kaempferol (0.286 mg/lt) (FIG. 9A, 9B, 9C, 9D). Surprisingly, when caffeic acid was used as a precursor metabolite the only flavonoid compound identified was the corresponding flavanone eriodictyol at a concentration of 22 μg/lt (FIG. 9E, 9F). No dihydroquercetin or quercetin was produced. However, quercetin biosynthesis has been achieved by functionally expressing a P450 monooxygenase, F3'5' H (flavonoid 3'5'-hydroxylase) from *Catharanthus roseus* in *E. coli*. Functional expression has been achieved by creating a fusion protein between the P450 monooxygenase and the P450 reductase CPR from *C. roseus*. The fusion protein was then cloned on a medium or low copy number vector. Finally, when cinnamic acid was used as a precursor metabolite, only the corresponding flavanone pinocembrin was detected in the medium at a concentration of 199 μg/lt (FIG. 9G, 9H). No pinobanksin or galangin accumulated, in accordance with our previous results that demonstrated that pinocembrin could not be accepted as a substrate by FHT and FLS1.

Because of the intriguing result obtained when caffeic acid was used as the precursor metabolite, we tested flavonol biosynthesis starting from low concentrations of flavanones and using the BL21Star strain carrying plasmid pRSF-FLS1-F3H. Neither dihydroflavonols nor flavonols could be detected when the precursor flavanones (naringenin or eriodictyol) were present at low concentrations, ranging from 25 μg/lt to 100 μg/lt.

We also performed the shake flask experiments in LB medium, under the same conditions as described for the M9 medium. When p-coumaric acid was used as a precursor, naringenin (0.39 mg/lt) and dihydrokaempferol (1.29 mg/lt) accumulated in the fermentation broth but no kaempferol was produced. When caffeic acid was used as a precursor, eriodictyol accumulated at a lower concentration compared to the M9 medium (7.5 μg/lt), while no dihydroquercetin or quercetin was detected. Finally, when cinnamic acid was used, pinocembrin accumulated at a concentration of 0.245 mg/lt and no dihydroflavonol or flavonol was detected.

The results of our shake flask experiments are presented in Table 5.

TABLE 5

| | Production in M9 (μg/liter) | | | Production in LB (μg/liter) | | |
|---|---|---|---|---|---|---|
| | Flavanone | Dihydro-flavonol | flavonol | Flavanone | Dihydro-flavonol | Flavonol |
| Caffeic acid | 22.1 | 0 | 0 | 7.5 | 0 | 0 |

TABLE 5-continued

| | Production in M9 (µg/liter) | | | Production in LB (µg/liter) | | |
|---|---|---|---|---|---|---|
| | Flavanone | Dihydro-flavonol | flavonol | Flavanone | Dihydro-flavonol | Flavonol |
| Cinnamic acid | 199 | 0 | 0 | 245 | 0 | 0 |
| p-coumaric acid | 74 | 643 | 286 | 390 | 1290 | 0 |

EXAMPLE 3

This example describes the biosynthesis of milligram quantities of flavanone substances from *S. cerevisiae* recombinant strain for the first time. This has been achieved using a plant-derived gene cluster that proved to be stable in yeast despite the presence of repeated DNA sequences (GAL1 promoter).

Materials and Methods

Plant material, bacterial strain, yeast strains, plasmids and chemicals. Parsley seeds were purchased from Stokes Seeds (Buffalo, N.Y.) while *petunia* plants were purchased from local nurseries. *S. cerevisiae* strain INVSC1 (MATa his3D1 leu2 trp1-289 ura3-52) (Invitrogen, Carlsbad, Calif.) was employed for yeast transformation and shake flask experiments. *E. coli* TOP10F' (Invitrogen) was used for plasmid construction and maintenance. *S. cerevisiae* plasmids pYES2.1/V5-His-TOPO (Invitrogen) and YEplac181 (American Type Culture Collection, Manassas, Va.) were used for cloning purposes. p-Coumaric acid, cinnamic acid, caffeic acid and ferulic acid were purchased from MP Biomedicals Inc. Naringenin was purchased from Sigma-Aldrich (St. Louis, Mo.) and eriodictyot; homoeriodictyol and pinocembrin were purchased from Indofine (Hillsborough, N.J.).

DNA Manipulations. All DNA manipulations were performed according to standard prodedures. Restriction enzymes, Calf Intestine Alkaline Phosphatase and T4 DNA ligase were purchased from New England Biolabs and Promega. All ReveFse Transcription Polymerase Chain Reactions (RT-PCR) were performed using Superscript One-step w/platinum Taq kit (Invitrogen). All Polymerase Chain Reactions (PCR) were performed using Roche's Expand High Fidelity PCR system. C4H cDNA from *Arabidopsis thaliana* was isolated by high-fidelity PCR from EST clone RAFL06-11-J16, identified through homology search performed at The Institute for Genomic Research *A. thaliana* database (www.tigr.org/tdb/e2k1/ath1) and purchased from RIKEN BioResource Center (Tsukuba, Japan). CHI-A and chs cDNA from *Petuniaxhybrida* and Pc4cL-2 from parsley (*Petroselinum crispum*) were amplified based on DNA sequences available in GenBank (accession numbers AF233638 for chs, X14589 for CHI-A and X13225 for Pc4cL-2). More specifically, the Qiagen RNeasy MiniKit was used for total RNA isolation from *P.×hybrida* corolla or *P. crispum* young leaves. In all cases, the absence of undesired mutations introduced during PCR was verified by direct nucleotide sequencing. Transformation of yeast was carried out using the lithium acetate method.

Figure 10:
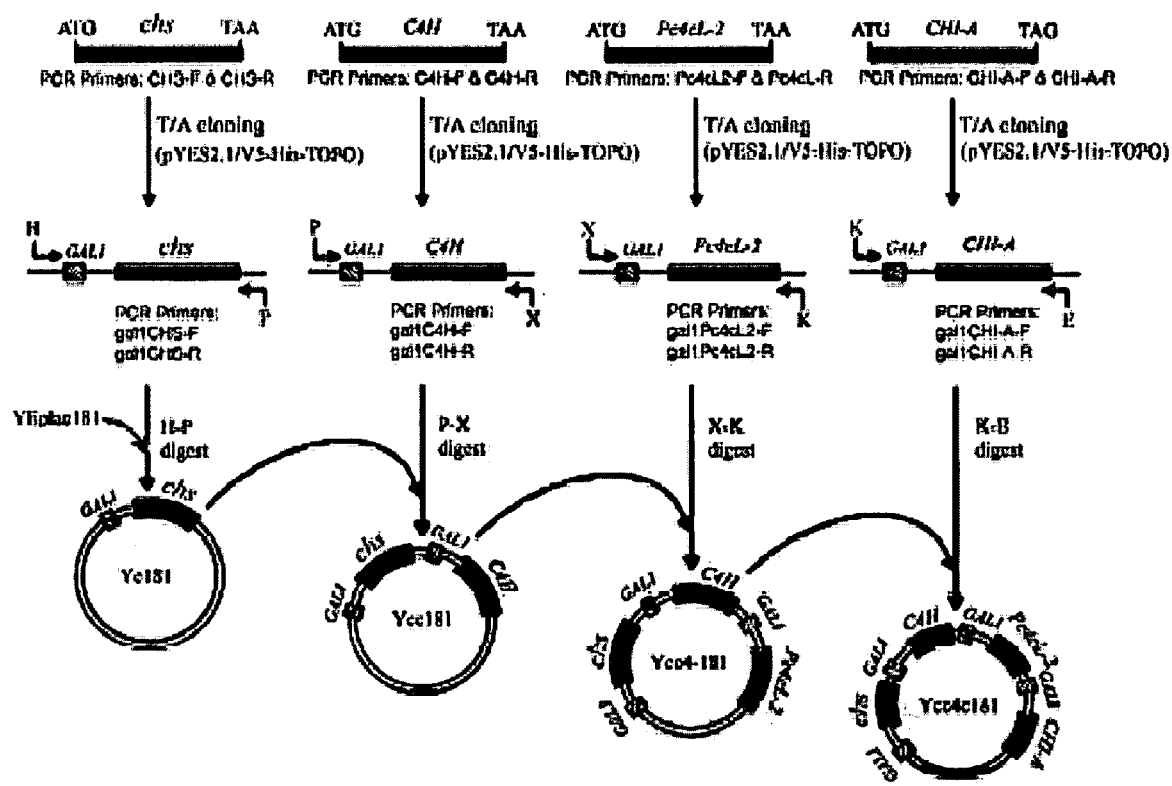
FIG. 10: Schematic representation of the cloning strategy used for assembling plasmid Ycc4c181. The following abbreviations are used for restriction enzymes: H, Hind III; P, Pst I; X, Xba I; K, Kpn I; E, EcoR I. By performing a first round of PCR or RT-PCR, each of the four genes C4H, Pc4CL-2 chs, and CHI-A was placed under the yeast GAL1 promoter derived from cloning vector pYES2.1V5-His-TOPO. In a second round of PCR, each gene was amplified together with the GAL1 promoter and placed sequentially into yeast cloning vector YEplac181. PCR and RT-PCR primer sequences used are presented in Table 6.

Construction of Plasmid Ycc4c181. Plasmid Ycc4c181 was constructed through two rounds of PCR for each of the four genes cloned, as depicted in FIG. 10. In the first round of PCR, each of the four structural genes (from the start codon ATG to the stop codon) was amplified either from a plasmid provided or from total RNA. After adding an A-overhang to the PCR products using Taq polymerase (Fisher Scientific, USA), each structural gene was individually cloned under the strong GAL1 promoter by T/A cloning using pYES2.1V5-His-TOPO vector. The GAL1 promoter is a strong yeast promoter induced by galactose.

In the second round of cloning, the chs cDNA together with the GAL1 promoter was amplified by high fidelity PCR, using a forward primer hybridizing to a vector DNA region that lies upstream of the GAL1 promoter and a reverse primer that hybridizes at the end of the cloned cDNA. A Hind III restriction site was introduced in the forward primer and a Pst I restriction site was introduced in the reverse primer. The resulting PCR fragment was digested with Hind III and Pst I and inserted into yeast vector YEpLac181 digested with the same enzymes, yielding plasmid Yc181. Similarly, the C4H cDNA was amplified together with the GAL1 promoter using a forward primer hybridizing upstream of the GAL1 promoter and carrying the Pst I restriction site while the reverse primer contained the restriction site Xba I. The PCR fragment was digested with Pst I and Xba I and inserted into plasmid Yc181 digested with the same enzymes, yielding plasmid Ycc181. Next the Pc4cL-2 cDNA together with the GAL1 promoter was amplified by PCR using a forward primer carrying the restiction site Xba I and a reverse primer carrying restriction site Kpn I. The amplified PCR fragment was digested with Xba I and Kpn I and inserted into plasmid Ycc181, resulting in plasmid Ycc4-181. Finally, CHI-A cDNA was isolated together with the GAL1 promoter by using a forward primer carrying restriction site KpnI and a reverse primer carrying restriction site EcoR I, the resulting PCR product was digested with Kpn I and EcoR I and inserted into plasmid Ycc4-181 digested with the same enzymes, which resulted in the final construct Ycc4c181. All the primer sequences used for the first and second round of PCR are listed in the Table 6.

TABLE 6

| Primer | Sequence (5'-3')[a] | |
|---|---|---|
| C4H-F | ATGGACCTCCTCTTGCTGGAGAAGT- | (SEQ ID NO:27) |
| C4H-R | TTAACAGTTCCTTGGTTTCATAACGATTATGGAGTGG | (SEQ ID NO:28) |
| Pc4cL2-F | ATGGGAGACTGTGTAGCACCCAAAG- | (SEQ ID NO:29) |
| Pc4cL2-R | TTATTTGGGAAGATCACCGGATGC- | (SEQ ID NO:30) |
| CHS-F | ATGGTGACAGTCGAGGAGTATCGTA- | (SEQ ID NO:31) |

TABLE 6-continued

| Primer | Sequence (5'-3')[a] |
|---|---|
| CHS-R | TTAAGTAGCAACACTGTGGAGG ACA - (SEQ ID NO:32) |
| CHI-A-F | ATGTCCTCCAGTGTCCGTT ACTA - (SEQ ID NO:33) |
| CHI-A-R | CTAGACTCCAATCACTGGAATA GTAGATTTCTCGG (SEQ ID NO:34) |
| gal1C4H-F | GGGGCTGCAGACGGATTAGAAG CCGCCGAG - (SEQ ID NO:35) |
| gal1C4H-R | CCCCTCTAGATTAACAGTTCCT TGGTTTCATAACGATTATGGAG TGG - (SEQ ID NO:36) |
| gal1Pc4cL2-F | GGGGTCTAGAACGGATTAGAAG CCGCCGAG - (SEQ ID NO:37) |
| gal1Pc4cL2-R | CCCCGGTACCTTATTTGGGAAG ATCACCGGATGC (SEQ ID NO:38) |
| gal1CHS-F | GGGGAAGCTTACGGATTAGAAG CCGCCGAG - (SEQ ID NO:39) |
| gal1CHS-R | CCCCCTGCAGTTAAGTAGCAAC ACTGTGGAGGACA (SEQ ID NO:40) |
| gal1CHI-A-F | GGGGGGTACCACGGATTAGAAG CCGCCGAG - (SEQ ID NO:41) |
| gal1CHI-A-R | CCCCGAATTCCTAGACTCCAAT CACTGGAATAGTAGATTTCTC GG - (SEQ ID NO:42) |

[a]Underlining indicates restriction enzyme cleavage sites, corresponding to the primer description. Boldface indicates start codon and italics indicate stop codon.

Yeast Shake Flask Experiment. A single colony of strain INVSC1 carrying plasmid Ycc4c181 was inoculated into 15 ml of SC-Leu minimal medium containing 2% glucose and was left to grow overnight at 30° C. with shaking (preinoculum). The following day, 50 ml induction medium (SC-Leu medium containing 2% galactose) was seeded with medium-free preinoculum to a final absorbance at 600 nm ($A_{600}$) of 0.4. Cells were then left to grow at 30° C. with vigorous shaking for 4 hours. At that time, 50 µl of a 0.25 M stock solution of substrate (cinnamic acid, p-coumaric acid, caffeic acid or ferulic acid) were added to the culture to a final concentration of 0.25 mM. The culture was left to grow at 30° C. for a total of 65 hours with horizontal shaking. During that time, the culture was supplemented with another 50 µl of substrate stock every 12 hours for a total of 4 times.

Flavonoid extraction. After completion of the shake flask experiments, flavonoid substances were extracted from the culture with an equal volume (approximately 50 ml) of ethyl acetate for around 30 seconds at room temperature with vigorous shaking. After another centrigugation at 4000×g for 20 min, the organic layer was collected and evaporated to dryness by rotary evaporation and the resulting powder was dissolved in 0.2 ml DMSO and water to a final volume of 1 ml.

HPLC analysis. The products were analyzed by High Performance Liquid Chromatography (HPLC), using an Agilent 1100 series instrument and a reverse phase ZORBAX SB-C18 column (4.6×150 mm) maintained at 25° C. The compounds produced were separated by elution with an acetonitrile/water gradient, at a flow rate of 1.0 ml/min. The HPLC conditions were as follows: 10 to 40% for 10 min, 40 to 60% for 5 min and 60 to 10% for 2 min. The retention times under these HPLC conditions for the standard authentic samples are as follows: Pinocembrin-16.3; Naringenin—12.8; Eriodictyol—11.1; and Homoeriodictyol—12.9. Flavanones were detected and quantified by monitoring absorbance at 290 nm. The quantitative calibration curves were obtained with standard solutions of authentic flavanone compounds. Retention times were estimated according to the reverse-phase HPLC conditions describe herein.

Results

We designed a gene cluster in vector YEplac181 that would allow the conversion of phenylpropanoid acids to flavanones in *S. cerevisiae*. For this purpose, four structural genes of plant origin, namely C4H cDNA from *Arabidopsis thaliana*, Pc4cL-2 from *Petroselinum crispum*, CHI-A and chs cDNA from *Petunia×hybrida* were chosen to be heterologously expressed in yeast. All enzymes used in the present study have previously been expressed successfully in *E. coli* except for C4H.

For cloning the four-gene cluster in yeast, we followed a cloning strategy similar to that in *E. coli*. In the first step each gene is first cloned separately under a species-specific promoter (in the present case, the strong *S. cerevisiae* GAL1 promoter). In the second step, each gene is amplified together with the promoter and cloned using restriction digests to the plasmid of choice (in the present case *S. cerevisiae* plasmid YEplac181) (FIG. 10).

We tested the stability of plasmid Ycc4c181 carrying the four-gene cluster by growing the recombinant yeast strain for a maximum of 65 h at 30° C. in minimal medium. Culture samples were taken every 24 h, and after plasmid isolation the presence of each one of the four genes, together with the GAL1 promoter was tested by restriction digests and PCR reactions. No recombination events that would lead to loss of gene(s) or promoters were observed during the 65 h time frame.

Exploring flavanone biosynthesis in *S. cerevisiae*. We first tested the ability of the recombinant yeast strain to synthesize flavanone compounds by feeding it with cinnamic acid, which is the natural substrate of C4H, the first-step in the 4-gene metabolic pathway we constructed.

Cinnamic acid was provided in a total of 5 increments to the culture. We followed this feeding strategy because preliminary data demonstrated that high concentrations of cinnamic acid (above 0.5 mM) in the medium resulted in significant cell growth arrest. In all cases, after 65 hours of fermentation, only trace amounts of cinnamic acid were detected in the culture.

Figure 11:
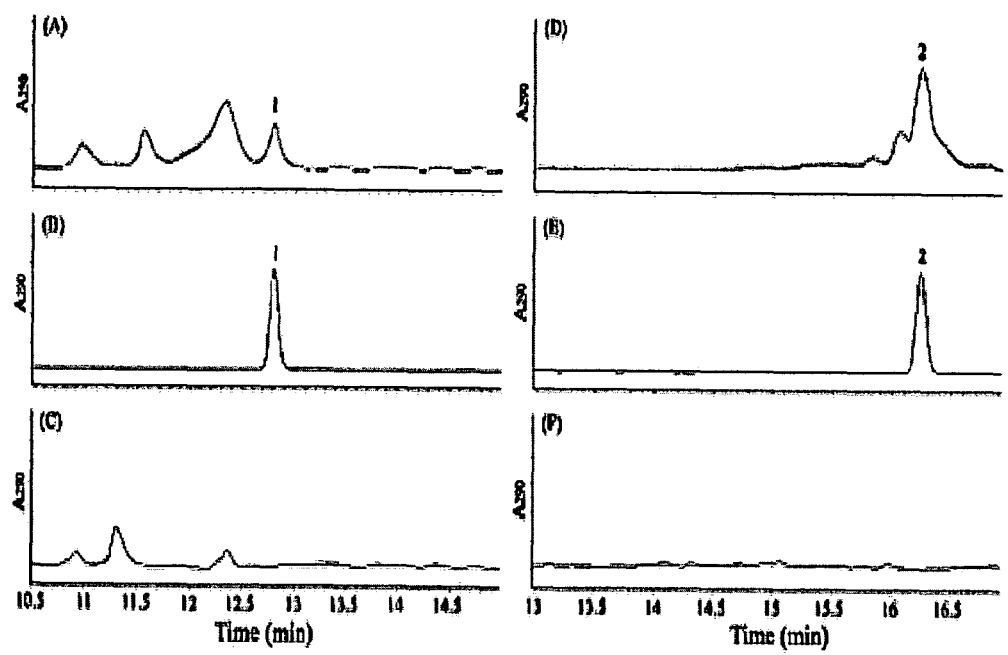
FIG. 11: Reverse phase HPLC analysis of shake flask culture carried out as described under "Materials and Methods". A and D; shake flask culture of recombinant Sacchromyces cerevisiae carrying plasmid Ycc4c181 fed with cinnamic acid; B, standard naringenin; E, standard pinocembrin; C and F, shake flask supernatant of INVSC1 carrying empty vector YEpLac181 fed with cinnamic acid (control); 1, naringenin; 2, pinocembrin.

With cinnamic acid as the precursor metabolite and galactose as the sole carbon source and inducer, large amount of the corresponding unhydroxylated flavanone pinocembrin accumulated in the medium (FIG. 11D, 11E, 11F). However, only a relatively small amount of naringenin was detected (FIG. 11A, 11B, 11C). Shake flask results are summarized in Table 7 and demonstrate that, although C4H was functionally expressed in yeast, it is still a rate limiting-step enzyme in the four-enzyme hybrid pathway. It is also indicative of the parsley 4CL versatile substrate activity. Overall, these results demonstrate the feasibility of flavanone biosynthesis in yeast.

TABLE 7

| | Production (mg/liter) | | | |
|---|---|---|---|---|
| | Pinocembrin | Naringenin | Eriodictyol | Homoeriodictyol |
| Cinnamic acid | 16.3 | 0.192 | N/A | N/A |
| 4-Coumaric acid | N/A | 28.3 | N/A | N/A |
| Caffeic acid | N/A | N/A | 6.5 | N/A |
| Ferulic acid | N/A | N/A | N/A | 0 |

<sup>a</sup>Cultures were grown in SC-Leu minimal medium with galactose as carbon source.

Feeding of other phenylpropanoid precursors to the engineered yeast strain. In order to increase the production of naringenin as well as explore the biosynthesis of other natural flavanone compounds, three other phenylpropanoid acids, namely p-coumaric acid, caffeic acid, and ferulic acid were tested as precursor metabolites.

Feeding of the culture with either of the three precursor phenylpropanoid acids was performed as previously described for cinnamic acid, since they all demonstrated growth inhibition. Flavanone compounds were identified by comparison of the retention time and UV profile with those of authentic standards and literature data.

Figure 12:
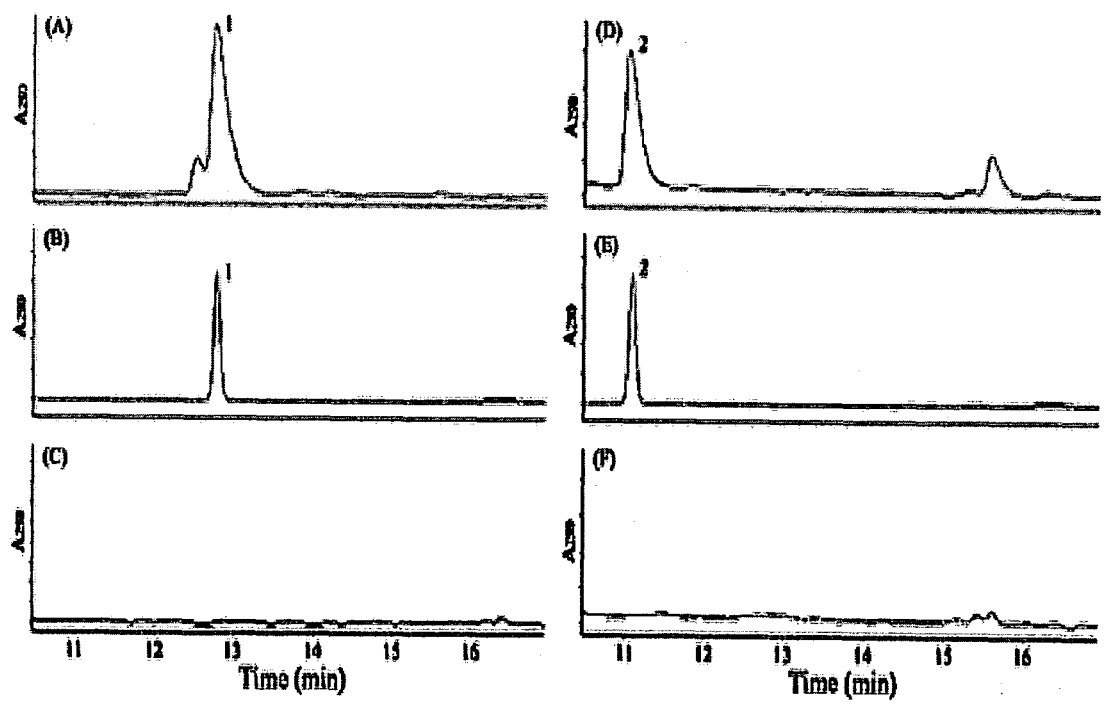
FIG. 12: Reverse phase HPLC analysis of shake flask culture carried out as described under "Materials and Methods". A; shake flask culture of recombinant Saccharomyces cerevisiae carrying plasmid Ycc4c181 fed with p-coumaric acid; B, standard naringenin; C, shake flask supernatant of INVSC1 carrying empty vector YEpLac181 fed with p-coumaric acid (control); D, shake flask culture of recombinant Saccharomyces cerevisiae carrying plasmid Ycc4c fed with caffeic acid; E, standard eriodictyol; F, shake flask supernatant of INVSC1 carrying empty vector YEpLac181 fed with ferulic acid (control); 1, naringenin; 2, eriodictyol.

As summarized in Table 7, in the case of p-coumaric acid, a large amount of naringenin accumulated in the culture (FIG. 12A, 12B, 12C). Similarly, when caffeic acid was used as a precursor, natural (2S)-eriodictyol was produced at significant amounts (FIG. 12D, 12E, 12F). This is the first time eriodictyol biosynthesis has been achieved through microbial fermentation. Finally, ferulic acid failed to be metabolized by the recombinant yeast strain and no homo-eriodictyol biosynthesis was observed.

EXAMPLE 4

This example demonstrates the synthesis of afzelechin from p-coumaric acid or (2S)-naringenin in E. coli. The set of genes encoding for plant enzymes 4CL, CHI, CHS, FHT, DFR and LAR were used were used for conversion of p-coumaric acid into afzelechin. A set of genes encoding for plant enzymes FHT, DFR and LAR were used for conversion of (2S)-naringenin into afzelechin.

Materials and Methods:

Bacterial strains, plasmids and culture conditions. E. coli TOP10F' (Invitrogen, Carlsbad, USA) was used for DNA manipulations while E. coli BL21Star or Rosetta were used for shake-flask experiments. Plasmids pTrcHis2-TOPO (Invitrogen), pETDuet-1, pCDFDuet-1 and pCOLADuet-1 (Novagen) were used for cloning purposes.

Genes

4-Coumaroyl CoA-ligase (Pc4cL-2 a.k.a. 4CL) was cloned from *Petroselinum crispum* (parsley). Chalcone synthase (CHS) was cloned from *Petunia hybrida* (petunia). Chalcone isomerase (CHI) was cloned from *Medicago sativa* (alfalfa). Flavanone 3 µl-hydroxylase (FHT a.k.a. F3H) was cloned from *Malus Domestica* (apple tree). Dihydroflavonol 4-reductase (DFR) was cloned from *Anthurium andraeanum* (flamingo flower). Leucoanthocyanidin reductase (LAR) was cloned from *Desmodium uncinatum* (spanish clover), a gift from Anthony R. Ashton (International patent WO 2002-AU179).

Chemicals p-Coumaic acid and LB media was obtained from MP Biomedicals. (2R/S)-Naringenin was purchased from Sigma-Aldrich (St. Louis, USA). Isopropyl-[beta]-D-Thiogalactoside (IPTG) was obtained from Fisher Scientific. M9 minimal media salts was obtained from Becton, Dickinson and Company. $FeSO_4 * 7H_2O$ was obtained from EM Science.

Construction of E. coli Plasmids.

Figure 13:
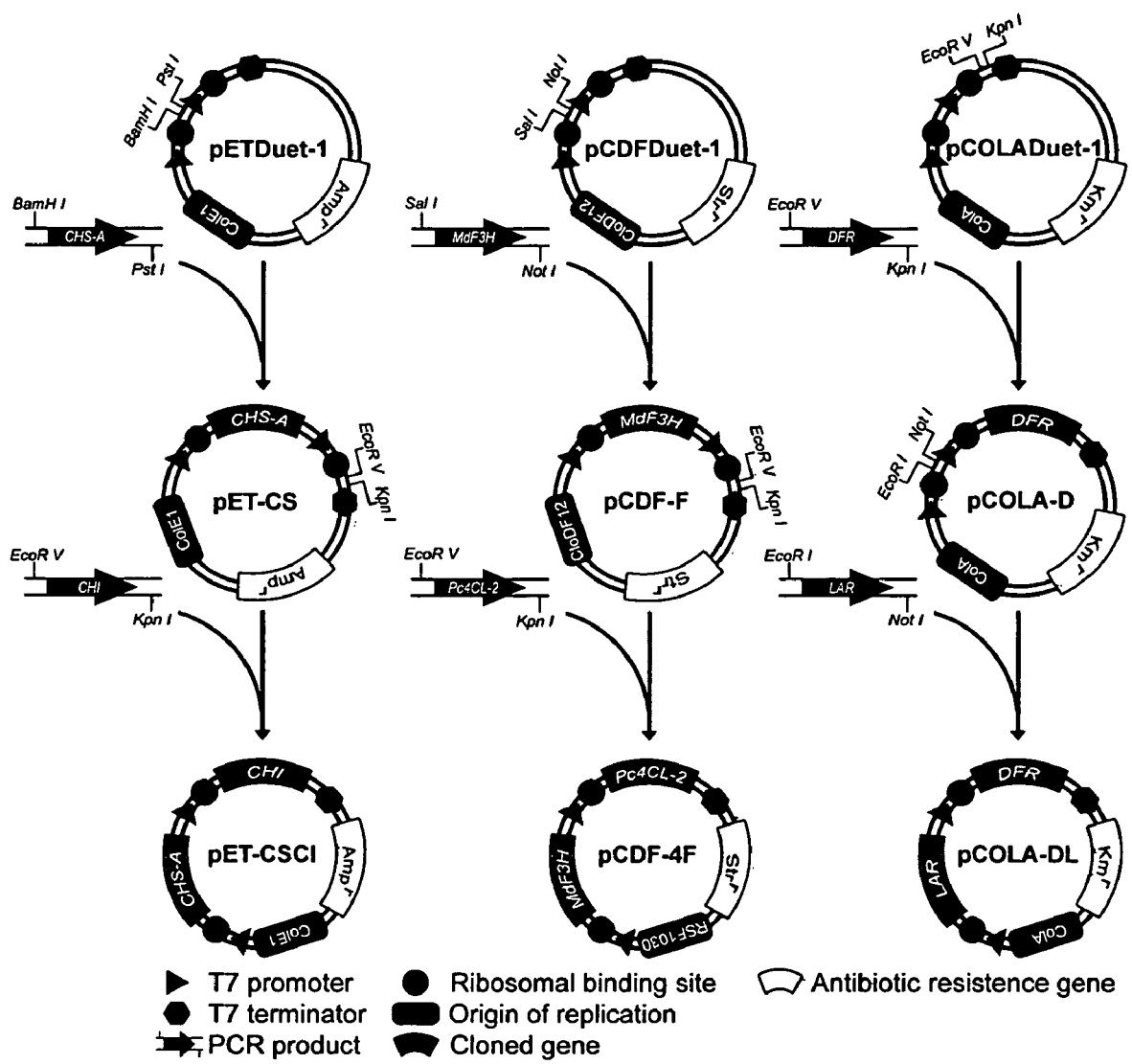
FIG. 13: Cloning strategy of plasmids constructed for the production of afzelechin in E. coli.
Figure 14A:
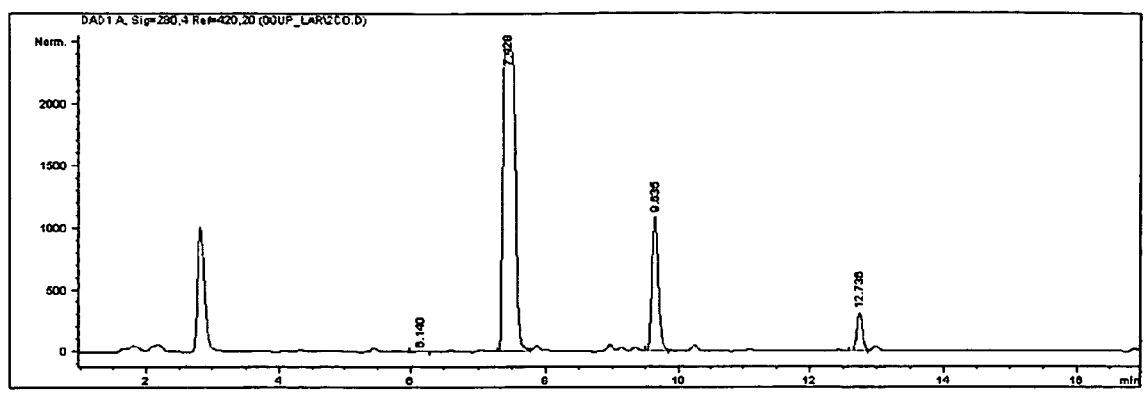
FIG. 14a: HPLC graph of fermentation extract for the production of afzelechin from p-coumaric acid using BL21Star e. coli with vectors pET-CSCI, pCD-F-4F and pCOLA-DL. Retention times: afzelechin 6.140 mins, p-coumaric acid at 7.428 mins, dihydrokaempferot at 9.635 mins, (2S)-naringenin at 12.736 mins.
Figure 14B:
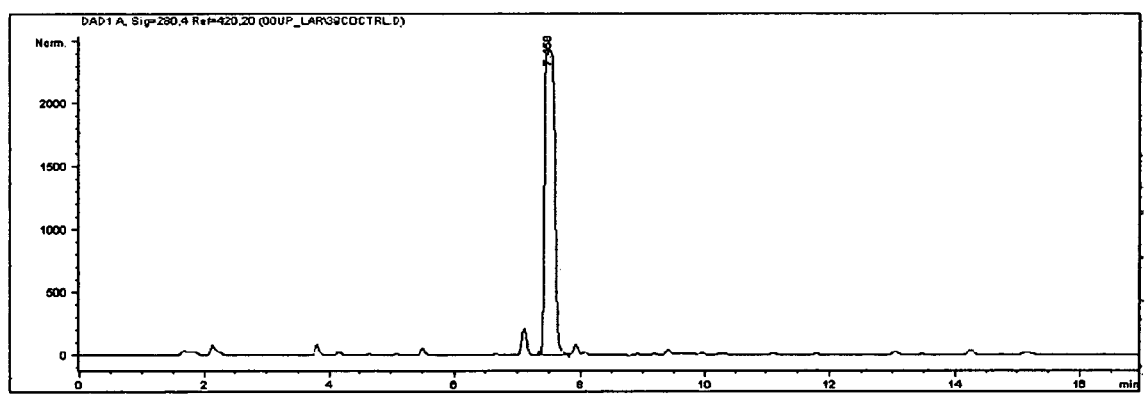
FIG. 14b: HPLC graph of fermentation extract for the control experiment with p-coumaric acid using BL21Star e. coli with empty vectors pETDuet-1, pCDFDuet-1 and pCOLADuet-1. Retention times: p-coumaric acid at 7.458 mins.
Figure 14C:
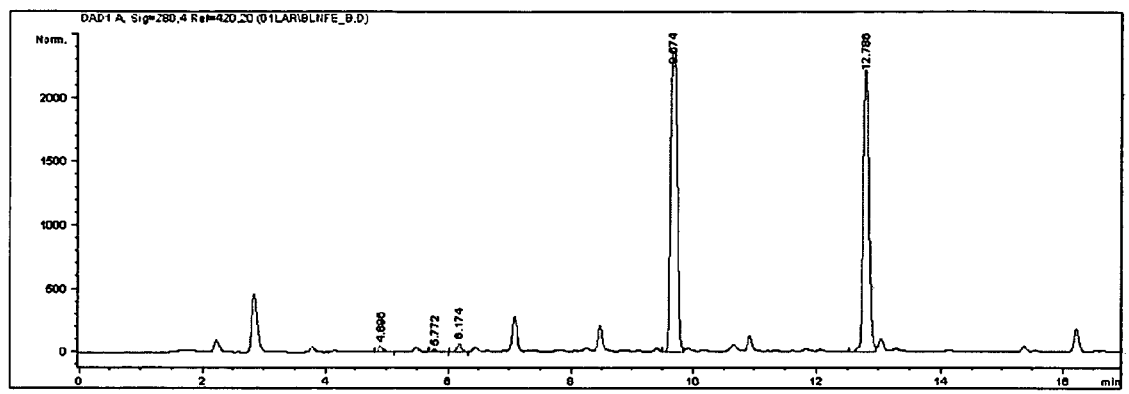
FIG. 14c: HPLC graph of fermentation extract for the production of afzelechin from (2S)-naringenin using BL21Star e. coli with vectors pCDF-F and pCOLA-DL. Retention times: cis-leucopelargonidin at 4.896 mins, trans-leucopelargonidin at 5.772 mins, afzelechin at 6.174 mins, dihydrokaempferol at 9.674 mins, (2R/S)-naringenin at 12.786 mins.
Figure 14D:
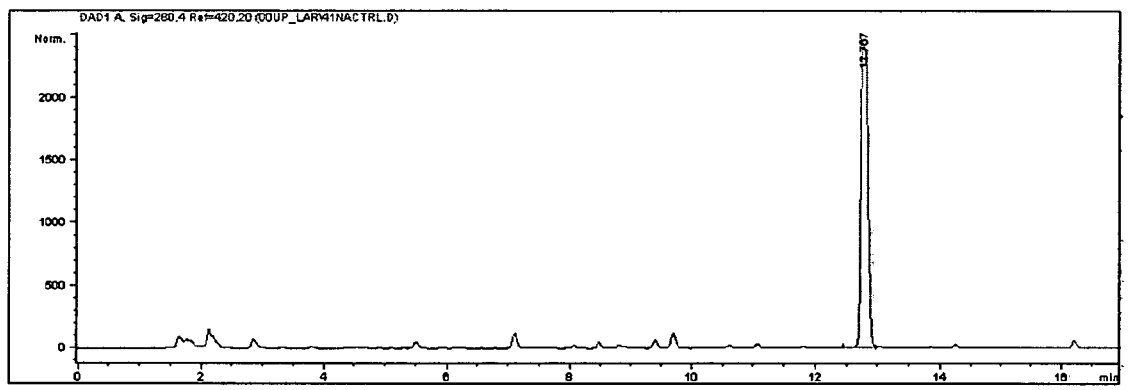
FIG. 14d: HPLC graph of fermentation extract for the control experiment with (2R/S)-naringenin using BL21Star e. coli with empty vectors pCDFDuet-1 and pCOLADuet-1. Retention times: (2R/S)-naringenin at 12.767 mins.

Plasmid pET-CSCI harboring chi and chs was constructed by subcloning chs between EcoR V and Kpn I and CHI-A between BamH I and Pst I sequentially in vector pETDuet-1. Plasmid pCDF-F containing mdf3h cDNA was constructed by subcloning Mdf3h between EcoR I and SalI sequentially into vector pCDFDuet-1. Plasmid pCDF-4F containing Pc4cL-2 and Mdf3h cDNA was constructed by subcloning Pc4cL2 between EcoR V and Kpn I into vector pCDF-F. Plasmid pCOLA-DL carrying dfr and lar was constructed by subcloning dfr between EcoR V and Kpn I and lar between EcoR I and Not I sequentially into vector pCOLADuet-1. Each gene was cloned under its own T7 promoters provided on each Duet vector. The gene constructs are presented in FIG. 13.

Batch Fermentation with Coumaric Acid as Substrate

Batch fermentations were prepared to determine the overall production of flavonoid compounds using commercially available p-coumaric acid. An overnight preinnoculums of recombinant E. coli BL21Star (Invitrogen) carrying vectors pET-CSCI, pCDF-4F and pCOLA-DL in LB or M9 minimal media. Antibiotics were added according to manufacturer's instructions (50 ug/mL ampicillin, 50 ug/mL streptomycin and 30 ug/mL kanamycin). The next day, 4 mL of the preinnoculum was used to seed 76 mL LB or M9 minimal media cultures in 250 mL flasks. Cultures were grown in an incubator at 37° C. until $OD_{600}$ reaches about 0.6. Gene expression was induced by 1 mM ITPG and the cultures were grown at 27° C. with horizontal shaking for 4 hours. p-Coumaric acid dissolved in DMSO was added to a final concentration of 0.5 mM. $FeSO_4$ was added to a final concentration of 0.1 mM. The cultures were incubated at 27° C. for 72 hours.

Batch Fermentation with Naringenin as Substrate

Batch fermentations were prepared to determine the overall production of flavonoid compounds using commercially available (2R/S)-naringenin. An overnight preinnoculums of recombinant E. coli BL21Star (Invitrogen) carrying vectors pCDF-F and pCOLA-DL in LB or M9 minimal media. Antibiotics were added according to manufacturer's instructions (50 ug/mL streptomycin and 30 ug/mL kanamycin). The next day, 4 mL of the preinnoculum was used to seed 76 mL LB or M9 minimal media cultures. The culture was grown in an incubator at 37° C. until $OD_{600}$ reaches about 0.6. Gene expression was induced by 1 mM ITPG and the cultures were grown at 27° C. with horizontal shaking for 4 hours. (2R/S)-Naringenin dissolved in DMSO was added to a final concentration of 0.2 mM. $FeSO_4$ was added to a final concentration of 0.1 mM. The cultures were incubated at 27° C. for 72 hours.

Extraction and Analysis of Flavonoids 15 mL of each culture was extracted with 25 mL ethyl acetate, dried using a rotary evaporator, and the residue was re-dissolved in 200 uL of acetonitrile. 25 uL samples were analyzed by HPLC using an Agilent HPLC 1100 series instrument with a diode array detector. HPLC was carried out using a reverse phase ZORBAX SB-C18 column (4.6×

150 mm) and an acetonitrile (solvent A) and water (solvent B) gradient (both solvents contain 0.1% formic acid), at a flow rate of 1 ml/min. The HPLC program conditions used were as follows: 10% to 40% A (0-10 mins) and 40% to 60% A (10-15 mins). Afzelechin eluted at 6.15 minutes. Using the same HPLC gradient, afzelechin where purified on a ZOR-BAX SC-C18 column (9.4×250 mm) but at a flow rate of 5 mL/min. Absorbance at 280 nm was monitored in all cases.

TABLE 8

| Substrate | Cofactor | Afzelechin Concentration (mg/L) |
| --- | --- | --- |
| 0.5 mM Coumaric acid | 0.1 mM FeSO4 | 0.042 ± 0.003 |
| 0.2 mM (2R/S)-Naringenin | 0.1 mM FeSO4 | 0.739 ± 0.056 |

Table 1: Concentration of afzelechin in fermentation broth produced from different substrates Product Characterization

*Escherichia coli* containing plasmids encoding plant enzymes (4CL, CHI, CHS, FHT, DFR and LAR) converted p-coumaric acid into afzelechin at a production concentration of about 0.042 mg/L. Production intermediates and by-products produced include (2S)-naringenin, dihydrokaempferol, cis-leucopelargonidin and trans-leucopelargonidin.

*Escherichia coli* containing plasmids encoding plant enzymes (FHT, DFR and LAR) converted (2S)-naringenin into afzelechin at a production concentration of about 0.739 mg/L (Table 8). Production intermediates and by-products produced include dihydrokaempferol, cis-leucopelargonidin and trans-leucopelargonidin As shown in FIGS. 14a-d, synthesized afzelechin eluted at about 6.15 mins. See FIGS. 14a-d. UV Maximum at 273 nm in methanol. Mass Spectroscopy (Low resolution negative ionization): 273.1 m/z (expected 273.3 m/z).

$^1$H NMR data were obtained in acetone-d6 (TMS as reference) using a 400 MHz Varian instrument.

(+)-Afzelechin $^1$H NMR (400 MHz, acetone-d$_6$): δ2.54 (dd, J=8.8, 16.4 Hz, H$_2$-4-Ha), δ2.95 (dd, J=5.6, 16.0 Hz, H$_2$-4-Hb), δ4.07 (ddd, J=5.6, 7.8, 8.5 Hz, H-3), δ4.60 (d, J=8.0 Hz, H-2), δ5.88 (s, H-8), δ6.03 (s, H-6), δ6.83 (d, J=8.4 Hz, H-3',5'), δ7.26 (d, J=8.4 Hz, H-2',6').

Primers Used for LAR:

```
Forward primer:  CCCAAGAATTCCGATGGCC (SEQ ID NO:43)
                 CTTATGACG -

Reverse primer:  GGGAAGTCGACCGCTAGCC (SEQ ID NO:44)
                 CATAGCTGAAATTGG -
```

EXAMPLE 5

This example demonstrates the synthesis of another flavan-3-ol, (+)-catechin, from caffeic acid or (2S)-eriodictyol in *E. coli*. The set of genes encoding for 4CL, CHI, CHS, FHT, DFR and LAR were used for synthesis of (+)-catechin from caffeic acid and a set of genes encoding FHT, DFR and LAR were used for synthesis of (+)-catechin from (2S)-eriodictyol.

Materials and Methods:

Bacterial strains, plasmids and culture conditions. *E. coli* TOP10F' (Invitrogen, Carlsbad, USA) was used for DNA manipulations while *E. coli* BL21Star or Rosetta were used for shake-flask experiments. Plasmids pTrcHis2-TOPO (Invitrogen), pETDuet-1, pCDFDuet-1 and pCOLADuet-1 (Novagen) were used for cloning purposes.

Genes. 4-Coumaroyl CoA-ligase (Pc4cL-2 a.k.a. 4CL) was cloned from *Petroselinum crispum* (parsley). Chalcone synthase (CHS) was cloned from *Petunia hybrida* (petunia). Chalcone isomerase (CHI) was cloned from *Medicago sativa* (alfalfa). Flavanone 3β-hydroxylase (FHT a.k.a. F3H) was cloned from *Malus Domestica* (apple tree). Dihydroflavonol 4-reductase (DFR) was cloned from *Anthurium andraeanum* (flamingo flower). Leucoanthocyanidin reductase (LAR) was cloned from *Desmodium uncinatum* (spanish clover), a gift from Anthony R. Ashton (International patent WO 2002-AU179).

Chemicals. Caffeic acid and LB media were obtained from MP Biomedicals. (2S)-Eriodictyol was purchased from Indofine. Authentic (+)-catechin was obtained from TCI America. Isopropyl-[beta]-D-Thiogalactoside (IPTG) was obtained from Fisher Scientific. M9 minimal media salts was obtained from Becton, Dickinson and Company.

Figure 15:
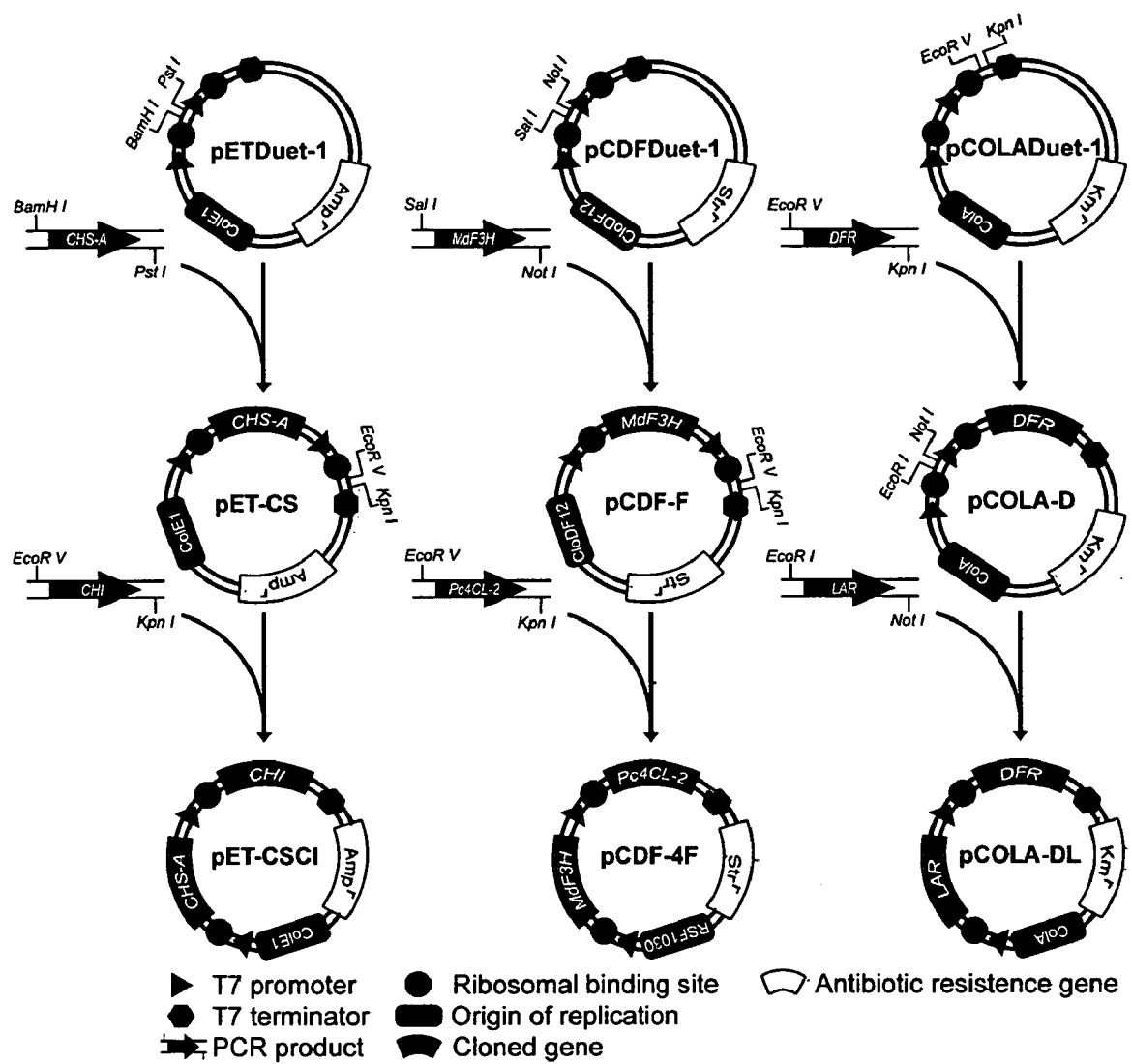
FIG. 15: Cloning strategy of plasmids constructed for the production of (+)-catechin in E. coli.
Figure 16A:
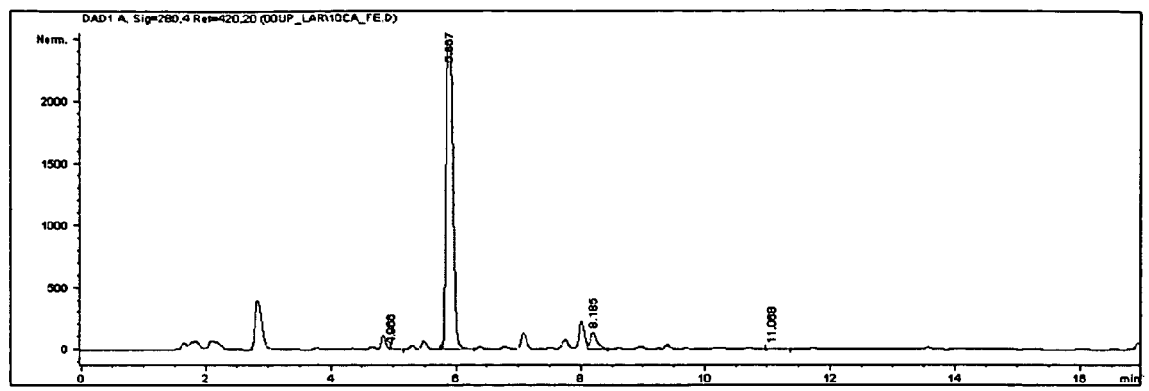
FIG. 16a: HPLC graph of fermentation extract for the production of (+)-catechin from caffeic acid using BL21Star e. coli with vectors pET-CSCI, pCDF-4F and pCOLA-DL. Retention times: (+)-catechin at 4.966 mins, caffeic acid at 5.867 mins, dihydroquercetin at 8.185 mins, (2S)-eriodictyol at 11.068 mins.
Figure 16B:
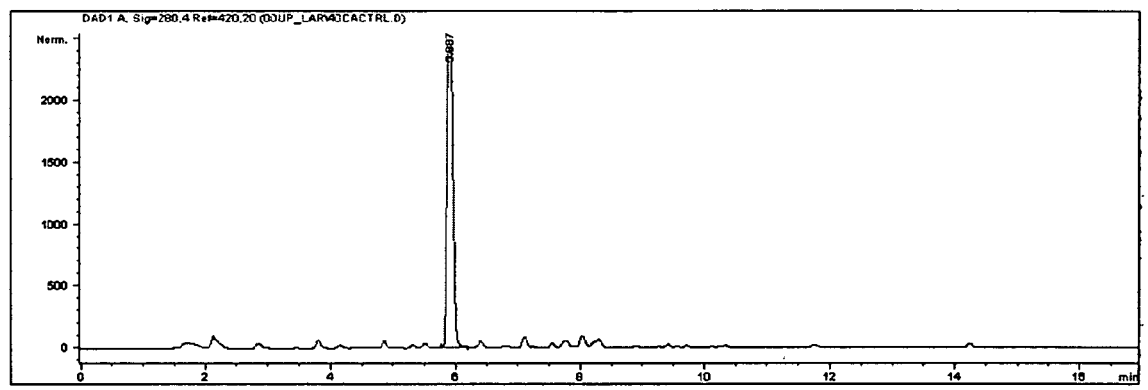
FIG. 16b: HPLC graph of fermentation extract for the control experiment with caffeic acid using BL21Star e. coli with empty vectors pETDuet-1, pCDFDuet-1 and pCOLADuet-1. Retention times: Caffeic acid at 5.887 mins.
Figure 16C:
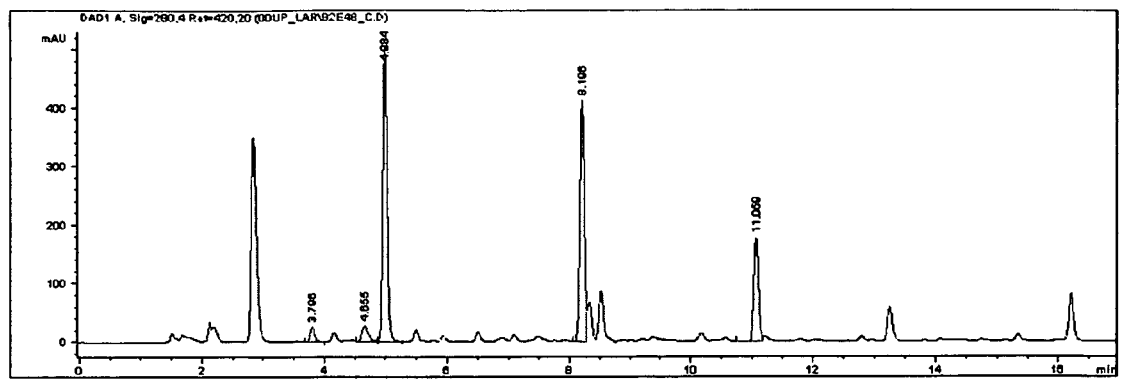
FIG. 16c: HPLC graph of fermentation extract for the production of (+)-catechin from (2S)-Eriodictyol using BL21Star e. coli with vectors pCDF-F and pCOLA-DL. Retention times: cis-leucocyanidin at 3.786 mins, trans-leucocyanidin at 4.655 mins, (+)-catechin at 4.984 mins, dihydroquercetin at 8.196 mins, (2S)-eriodictyol at 11.059 mins.
Figure 16D:
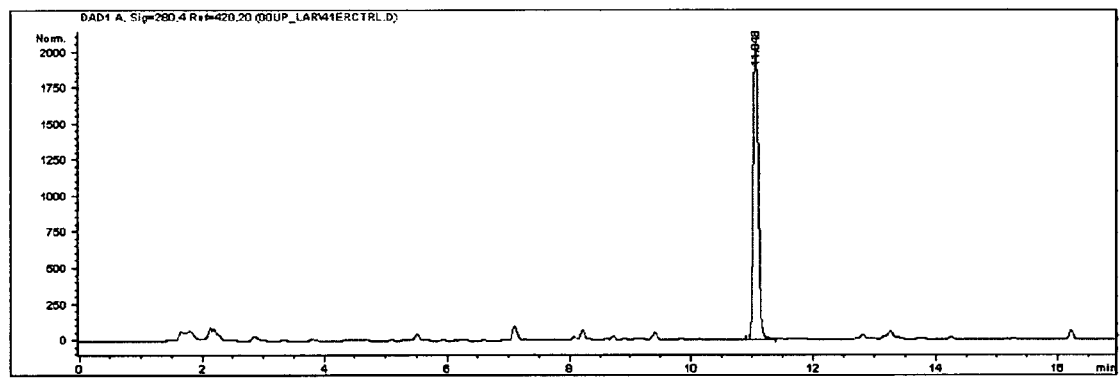
FIG. 16d: HPLC graph of fermentation extract for the control experiment with (2S)-eriodictyol using BL21Star e. coli with empty vectors pCDFDuet-1 and pCOLADuet-1. Retention times: (2S)-eriodctyol at 11.048 mins.
Figure 16E:
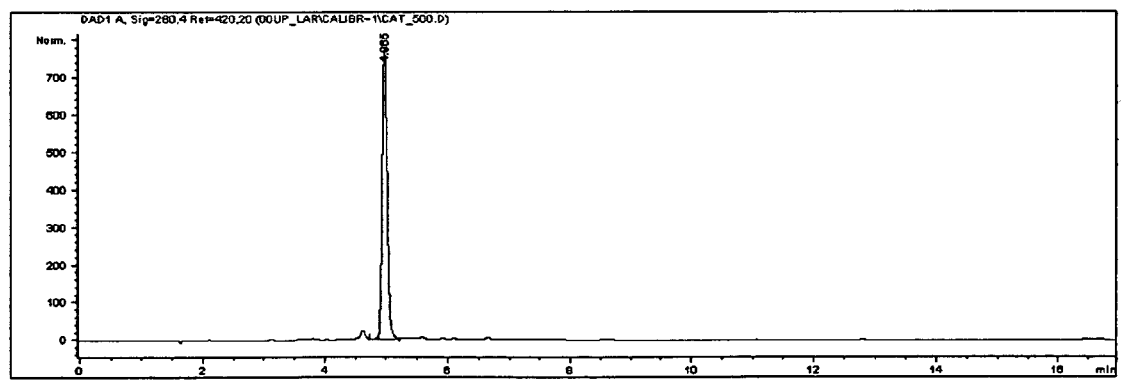
FIG. 16e: HPLC graph of authentic standard of (+)-catechin. Retention times: (+)-catechin at 4.965 mins.

Construction of *E. coli* plasmids. Plasmid pET-CSCI harboring chi and chs was constructed by subcloning chs between EcoR V and Kpn I and CHI-A between BamH I and Pst I sequentially in vector pETDuet-1. Plasmid pCDF-F containing mdf3h cDNA was constructed, by subcloning Mdf3h between EcoR I and SalI sequentially into vector pCDFDuet-1. Plasmid pCDF-4F containing Pc4cL-2 and mdf3h cDNA was constructed by subcloning Pc4cL2 between EcoR V and Kpn I into vector pCDF-F. Plasmid pCOLA-DL carrying dfr and lar was constructed by subcloning dfr between EcoR V and Kpn I and lar between EcoR I and Not I sequentially into vector pCOLADuet-1. Each gene was cloned under its own T7 promoters provided on each Duet vector. The gene constructs are presented in FIG. 15.

Batch Fermentation with Caffeic Acid as Substrate

Batch fermentations were prepared to determine the overall production of flavonoid compounds using commercially available caffeic acid. An overnight preinnoculums of recombinant *E. coli* BL21Star was prepared carrying vectors pET-CSCI, pCDF-4F and pCOLA-DL in LB or M9 minimal media. Antibiotics were added according to manufacturer's instructions (50 ug/mL ampicillin, 50 ug/mL streptomycin and 30 ug/mL kanamycin). The next day, 4 mL of the preinnoculum was used to seed 76 mL LB or M9 minimal media cultures in 250 mL flasks. Cultures were grown in an incubator at 37° C. until OD$_{600}$ reaches about 0.6. Gene expression was induced by 1 mM ITPG and the cultures were grown at 27° C. with horizontal shaking for 4 hours. Caffeic acid dissolved in DMSO was added to a final concentration of 0.5 mM. The cultures were incubated at 27° C. for 72 hours.

Batch Fermentation with Eriodictyol as Substrate

Batch fermentations were prepared to determine the overall production of flavonoid compounds using commercially available (2S)-eriodictyol. An overnight preinnoculums of recombinant *E. coli* BL21Star (Invitrogen) was prepared carrying vectors pCDF-F and pCOLA-DL in LB or M9 minimal media. Antibiotics were added according to manufacturer's instructions (50 ug/mL streptomycin and 30 ug/mL kanamycin). The next day, 4 mL of the preinnoculum was used to seed 76 mL LB or M9 minimal media cultures. The culture was grown in an incubator at 37° C. until OD$_{600}$ reaches about 0.6. Gene expression was induced by 1 mM ITPG and the cultures were grown at 27° C. with horizontal shaking for 4 hours. (2S)-Eriodictyol dissolved in DMSO was added to a final concentration of 0.2 mM. The cultures were incubated at 27° C. for 72 hours.

Extraction and Analysis of Flavonoids 15 mL of each culture was extracted with 25 mL ethyl acetate, dried using a rotary evaporator, and the residue was re-dissolved in 200 uL of acetonitrile. 25 uL samples were analyzed by HPLC using an Agilent HPLC 1100 series instrument with a diode array detector. HPLC was carried out using a reverse phase ZORBAX SB-C18 column (4.6× 150 mm) and an acetonitrile (solvent A) and water (solvent B) gradient (both solvents contain 0.1% formic acid), at a flow rate of 1 ml/min. The HPLC program conditions used were as follows: 10% to 40% A (0-10 mins) and 40% to 60% A (10-15 mins). (+)-Catechin eluted at 5.01 minutes. Using the same HPLC gradient, (+)-catechin where purified on a ZORBAX SC-C18 column (9.4×250 mm) but at a flow rate of 5 mL/min. Absorbance at 280 nm was monitored in all cases.

TABLE 9

| Substrate | Catechin Concentration (mg/L) |
|---|---|
| 0.5 mM Caffeic acid | 0.088 ± 0.004 |
| 0.2 mM (2S)-Eriodictyol | 8.802 ± 0.179 |

Table 1: Concentration of (+)-catechin in fermentation broth produced from different substrates Product Characterization

*Escherichia coli* containing plasmids encoding plant enzymes (4CL, CHI, CHS, FHT, DFR and LAR) converted caffeic acid into (+)-catechin at a production concentration of about 0.088 mg/L (Table 9). Production intermediates and by-products produced included (2S)-eriodictyol, dihydroquercetin, cis-leucocyanidin and trans-leucocyanidin.

*Escherichia coli* containing plasmids encoding plant enzymes (FHT, DFR and LAR) converted (2S)-eriodictyol into (+)-catechin at a production concentration of about 8.802 mg/L. Production intermediates and by-products produced include dihydroquercetin, cis-leucocyanidin and trans-leucocyanidin.

As shown in FIGS. 16*a-e*, synthesized (+)-catechin eluted at the same time as authentic (+)-catechin. The UV Maximum was at 279 nm in methanol. Mass Spectroscopy (Low resolution negative ionization): 289.5 m/z (expected 289.3 m/z)

Primers used to clone LAR were the same as in Example 4.

EXAMPLE 6

This example describes the biosynthesis of flavones in *E. coli*.

Materials and Methods

Chemicals and media. Luria Broth (LB), Terrific Broth (TB), YPD (10 g/L yeast extract, 20 g/L peptone, 20 g (L dextrose) or M9 minimal media (1× M9 salts, 0.4% glucose, 6 nM thiamine, 0.1 μM biotin, 1 μM $MgSO_4$, 0.1 μM $CaCl_2$) was used throughout. Ampicillin (100 μg/mL), kanamycin (50 μg/mL), and streptomycin (50 μg/mL) or combinations of these antibiotics were used when necessary. Cinnamic acid, p-coumaric acid and caffeic acid were purchased from MP Biomedicals Inc. (Irvine, Calif.). Naringenin was purchased from Sigma-Aldrich (St. Louis, Mo.). Ferulic acid, eriodictyol, apigenin, luteolin and genkwanin were purchased from Indofine (Hillsborough, N.J.).

Plant materials. Plants were purchased from local nurseries, and sun exposed for a few hours before various plant materials were collected. For mRNA extraction, young leaves of flat leaved parsley and peppermint, and flower petals of *Petunia×hybrida* were used. Plant material was quickly frozen with liquid nitrogen and stored at −80° C. until use.

Bacterial plasmids, and strains. *E. coli* TOP 10F' (Invitrogen) was used for transformation of cloning reactions and plasmid maintenance, while *E. coli* strain BL21Star was used for fermentations (Invitrogen). Three co-replicable vectors were used for the construction of the flavone biosynthetic pathway: the high copy number vector pRSF-Duet-1 (copy number: ~100), the medium copy number vector pETDuet-1 (~40), and the low copy number vector pCDFDuet-1 (~20) (Novagen). Additionally, vector pCRT7/CT was used for T/A cloning of PCR amplified DNA (Invitrogen). All strains and plasmids used in this example are shwon in Table 10.

TABLE 10

| Strain or plasmid | Genotype or properties |
|---|---|
| *E. coli* TOP 10F'(Invitrogen) | F' {lacI$^q$, Tn10(Tet$^R$)} mcrA (mrr-hsdRMS-mcrBC) 80lacZM15 lacX74 recA1 araD139 (ara-leu)7697 galU galK rpsL (Str$^R$) endA1 nupG |
| *E. coli* BL21 Star (Invitrogen) | F-ompT hsdS$_B$ (rB-mB-) gal dcm rnel31 (DE3) |
| pCRT7/CT (Invitrogen) | T/A cloning vector, AmpR |
| pRSFDuet-1 | Cloning vector, KmR |
| pETDuet-1 | Cloning vector, AmpR |
| pCDFDuet-1 | Cloning Vecotr, SmR |
| pCRT7-FSI | T7 RNAP$_{[a]}$ inducible FSI from *P. crispum* |
| pRSF-4CL | T7 RNAP$_{[a]}$ inducible 4CL from *P. crispum* |
| pRSF-4CL-FSI | T7 RNAP$_{[a]}$ inducible 4CL and FSI from *P. crispum* |
| pET-CHI | T7 RNAP$_{[a]}$ inducible CHI from *P. hybrida* |
| pET-CHI-CHS | T7 RNAP$_{[a]}$ inducible CHI and CHS from *P. hybrida* |
| pCDF-OMT | T7 RNAP$_{[a]}$ inducible OMT1A from *M. piperita* |

Molecular cloning. DNA manipulations were performed according to standard procedures 10 (Sambrook et al., 1989). Restriction enzymes and T4 DNA ligase were purchased from New. England Biolabs and Promega. Total RNA from plant materials was isolated using RNeasy Plant Mini Kit (Qiagen) according to manufacturer's instructions. cDNA was obtained and amplified by Reverse Transcription-PCR (RT-PCR) using SuperScript™ One-Step RT-PCR with Platinum® Taq (Invitrogen) and based on DNA sequence information available in GenBank. All primer sequences used for cDNA amplification are listed in Table 11.

TABLE 11

| Primer | Sequence (5'-3')[a] |
|---|---|
| Pc4cL-2-F - EcoRI | CCGGAATTCGGGATGGGAGACT GTGTAGCACCCAAG (SEQ ID NO:45) |
| Pc4cL-2-R - SalI | CCCGTCGACCCCTTATTTGGGA AGATCACCGGATGC (SEQ ID NO:46) |
| PcFSI-F - NdeI | GTTCCATATGCCCATGGCTCCT ACAACAATAACCGC (SEQ ID NO:47) |

TABLE 11-continued

| Primer | Sequence (5'-3')a |
|---|---|
| PcFSI-R - KpnI | CCTTGGTACCCGGCTAAGCTAA ATTTTCATCTGCACTC (SEQ ID NO:48) |
| chsA-F - BamHI | GGGGGGATCCGGATGGTGACAG TCGAGGAGTATCGTA (SEQ ID NO:49) |
| chsA-R -PstI | CCC*CTGCAG*CCTTAAGTAGCAA CACTGTGGAGGACA (SEQ ID NO:50) |
| chiA-F - EcoRV | GGGGGATATCGGATGTCTCCTCC AGTGTCCGTTACTA (SEQ ID NO:51) |
| chiA-R -KpnI | CCCCGGTACCCCCTAGACTCCA ATCACTGGAATAGTAG (SEQ ID NO:52) |
| OMT -F - EcoRI | CCTGAATTCGGATGGCACCGGA AGAAGATTCACTAG (SEQ ID NO:53) |
| OMT-R -PstI | CAAA*CTGCAG*CCTCAGGGATAG GCCTCAATGACCG (SEQ ID NO:54) |

Underlining indicates restriction enzyme cleavage sites, corresponding to the primer description. Boldface indicates start codon and italics indicate stop codon In order to assess the functional expression of FSI in *E. coli*, PcFSI cDNA was cloned into vector pCRT7/CT, yielding plasmid pCRT7-FSI.

Figure 17:
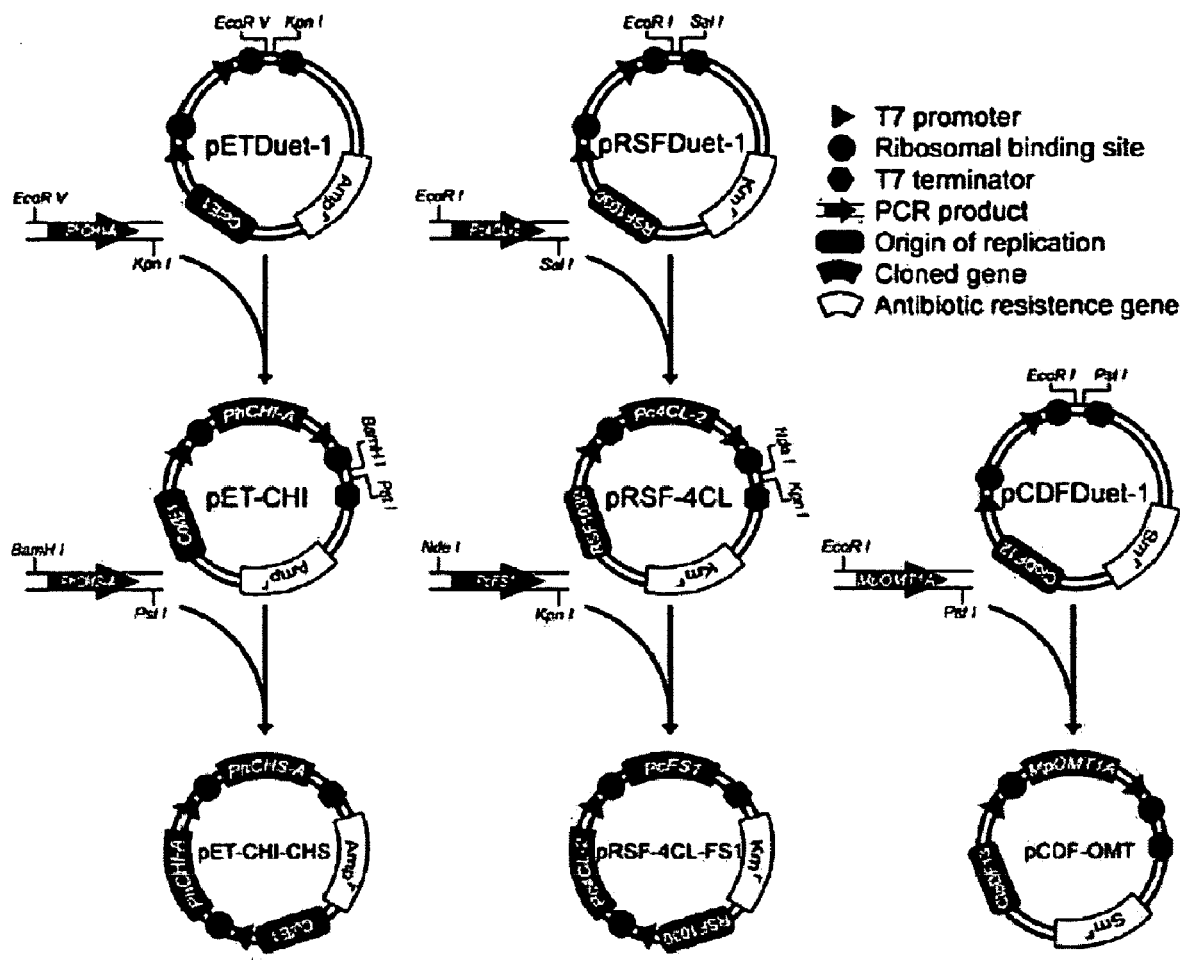
FIG. 17: Schematic representation of the strategy used for constructing plasmids expressing the flavone biosynthetic enzymes. PCR and RT-PCR primer sequences used are presented in Table 11

For construction of the flavone biosynthetic pathway (FIG. 17), the PCR product of Pc4CL-2 was cloned into pRSFDuet-1 between EcoRI and SalI sites, yielding plasmid pRSF-4CL. Subsequently, PcFSI was cloned into pRSF-4CL between Nde1 and Kpn1, resulting in plasmid pRSF-4CL-FSI. Similarly, plasmid pET-CHI-CHS was constructed by first subcloning chiA between EcoR V and KpnI, and then chsA between BamHI and PstI in vector pETDuet-1, yielding plasmid pET-CHI-CHS. OMT1A was cloned into pCDFDuet-1 between EcoRI and PstI sites, yielding plasmid pCDF-OMT. In all cases, successful gene cloning was verified by restriction mapping and the absence of undesired mutations introduced during PCR was verified by direct nucleotide sequencing.

Protein expression and fermentation. The expression of parsley FSI in *E. coli* was investigated in vivo. For that purpose, recombinant BL21Star carrying plasmid pCRT7-FSI plasmid was cultured in 3 ml liquid LB with ampicillin (pre-inoculum) overnight at 37° C. with shaking. The following day, the pre-inoculum culture was used to seed a fresh 50 ml LB culture to an initial absorbance at 600 nm (Ab$_{(600)}$) of 0.05, that was then left to grow at 37° C. until Ab$_{(600)}$ reached 0.6. At that point, the inducer IPTG was added to the culture to a final concentration of 1 mM, and incubation continued at 30° C. in order to minimize probable inclusion body formation of the recombinant protein. After 4 hours, 0.05 mM of naringenin or eriodictyol was added to the culture and incubation proceeded for another 24 hours.

In order to obtain different flavone products from phenylpropanoid acids, *E. coli* strain BL21Star was transformed with different combinations of plasmids. Co-transformation of pRSF-4CL-FSI along with pET-CHI-CHS was performed for production of unmodified flavones. For methylated flavones, BL21Star was co-tranformed with pRSF-4CL-FSI, pET-CHI-CHS, and pCDF-OMT.

For fermentation purposes, a 3-mL LB overnight pre-innoculum was prepared using the recombinant strains. The next day, a 1 mL portion of the pre-innoculum was used to start a 50 mL fresh LB culture, supplemented with appropriate antibiotics. The culture was grown at 37° C. with shaking, until Ab$_{(600)}$ reached 0.6. At that point, the expression of the recombinant genes was induced with 2 mM IPTG, and incubation continued at 30° C. for 4 more hours. At the end of the incubation period, 1 mL of the induced culture was added to a fresh 49 mL M9 minimal medium or LB or TB or YPD, that also contained the appropriate antibiotics, 1 mM IPTG, 0.5 mM of 2-oxoglutaric acid, 0.5 mM FeSO$_4$, 0.5 mM sodium ascorbate and 0.05 mM precursor phenylpropanoid acids. The culture was then incubated at 30° C. with shaking (300 rpm) for 24 hours.

Analytical methods. The culture broth and the bacterial pellets were analyzed separately for flavonoid production. Cells were collected by centrifugation, washed twice in 0.9% NaCl solution and extracted for 1 hour in MeOH—HCl (v/v, 10:1) in an ultrasonic bath. An equal amount of ethyl acetate was then added to the culture broth or cell lysate, followed by vigorous mixing. The organic phase was separated by centrifugation, decanted, and evaporated under vacuum to dryness. Acetonitrile/water mixture (v/v, 1:3) was then added to dissolve the organic compounds.

Flavonoids and phenylpropanoid acids were analyzed by High Performance Liquid Chromatography (HPLC), using an Agilent 1100 series instrument and a reverse phase ZORBAX SB-C18 column (4.6×150 mm), maintained at 25° C. The compounds were separated by elution with an acetonitrile/water gradient, at a flow rate of 1.0 ml/min. The HPLC conditions were as follows: 20 to 27% (volume percentage of acetonitrile) for 45 min, and 27 to 95% (volume percentage of acetonitrile) for 30 sec. The retention times under these conditions for the standard authentic samples are: caffeic acid, 2.7 min; p-coumaric acid, 4.7 min; eriodictyol, 18.4 min; luteolin, 20.8 min; naringenin, 30.9 min; apigenin, 33.2 min; genkwanin, 46.7 min. Flavanones were detected and quantified by monitoring absorbance at 290 nm. Flavones were detected and quantified at 340 nm. Calibration curves were obtained with authentic flavanone and flavone solutions of various concentrations.

Results

Figure 18:
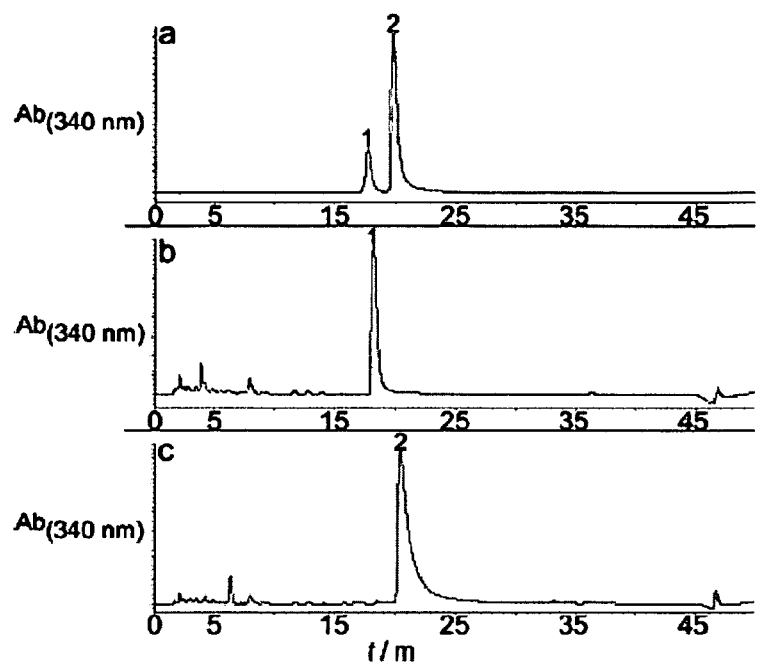
FIG. 18: HPLC analysis of extracts from shake flask supernatants of recombinant BL21Star carrying plasmid pCRT7-FSI and performed—(a), luteolin (2), produced from the recombinant strain when fed with eriodictyol (1); (b), control experiment with BL21Star carrying empty vector pCRT7/CT and fed with eriodictyol (1); (c), standard luteolin (2).

Expression of FSI in *E. coli*. In order to express FSI in *E. coli*, FSI cDNA was PCR amplified and cloned under the strong T7 promoter (plasmid pCRT7-FSI). Recombinant *E. coli* BL21Star carrying pCRT7-FSI was grown in the presence of 0.05 mM of the dihydroxylated flavanone (2S)-eriodictyol to test for the biosynthesis of the corresponding flavone (luteolin) upon induction with 0.1 mM IPTG. As shown in FIG. 18a, the fermentation of the recombinant *E. coli* generated the flavone luteolin which was identified by matching the retention time and the UV absorbance spectra of the authentic compound (FIG. 18c; control experiment in presented in FIG. 18b). Similar results were obtained when the recombinant strain was grown in the presence of the monohydroxylated flavanone naringenin, producing the corresponding flavone apigenin (results not shown). Overall, these results demonstrated the functional expression of parsley FSI in *E. coli*.

Recombinant *E. coli* generates flavone derivatives from phenylpropanoid acids. With the purpose of producing flavones from their precursor phenylpropanoid compounds, we constructed the flavone biosynthetic pathway in *E. coli* using five heterologous genes of plant origin. These genes included Pc4CL-2 (Lozoya et al., 1988. *Eur J Biochem* 176 (3), 661-667) and PcFSI (Martens et al., 2001, *Phytochemistry*, 58:43-46) from parsley, chsA and chiA from *petunia* (Vantunen et al., 1989, *Plant Mol Biol* 12 (5), 539-551;

Vantunen et al., 1988, *EMBO J.*, 7 (5), 1257-1263) and OMT1A from peppermint (Willits et al., 2004, *Phytochemistry*, 65:31-41.

All genes were cloned under the strong T7 inducible phage promoter. Two different combinations of the five genes were used in order to produce unmodified or methylated flavone molecules: in order to produce unmodified flavones, pRSF-4CL-FSI, and pET-CHI-CHS plasmids were employed; for methylated flavone biosynthesis, in addition to the two plasmids, pCDF-OMT plasmid was also transformed.

Figure 19:
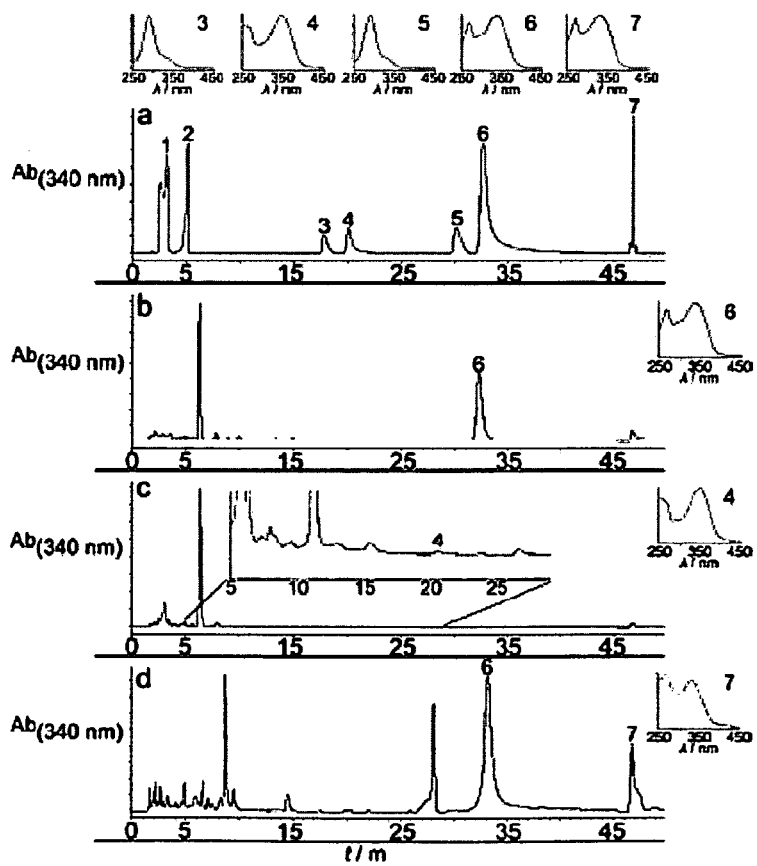
FIG. 19: HPLC analysis of extracts from shake flask supernatants of recombinant BL21Star carrying various plasmid combinations. Cultures were grown in M9 minimal medium. (a) authentic compounds caffeic acid (1), p-coumaric acid (2), eriodictyol (3), luteolin (4), naringenin (5), apigenin (6) and genkwanin (7); (b) apigenin (6) produced when recombinant BL21Star carrying plasmids pRSF-4CL-FSI and pET-CHI-CHS was fed with p-coumaric acid; (c) luteolin (4) produced when recombinant BL21Star carrying plasmids pRSF-4CL-FSI and pET-CHI-CHS was fed with caffeic acid; (d) genkwanin (7) and apigenin (6) produced when recombinant BL21Star carrying plasmids pRSF-4CL- FSI, pET-CHI-CHS and pCDF-OMT was fed with p-coumaric acid. Inlets present the UV/Vis spectra of the compounds corresponding to the indicated HPLC peaks. Absorbance maxima of apigenin, naringenin, genkwanin, luteolin and eriodictyol are 266 nm and 36 nm, 288 nm, 268 nm and 330 nm, 266 nm and 348 nm, 286 nm respectively.

Biotransformation experiments with the recombinant strains were carried out in M9 minimal medium with various phenylpropanoid acids (cinnamic acid, p-coumaric acid, caffeic acid, ferulic acid) used as precursor metabolites. After 24 hours, the fermentation products were analyzed using HPLC and were compared with authentic compounds (FIG. 19*a*). As shown in FIGS. 19*b* and 19*c* when p-coumaric acid or caffeic acid was fed to the recombinant culture, apigenin or luteolin was produced after 24 hours. The flavanone precursor of apigenin, (2S)-naringenin, accumulated only in trace amounts, while the flavanone precursor of luteolin, (2S)-eriodictyol, was not detected in the medium. Feeding ferulic acid and cinnamic acid to the recombinant culture did not result in flavone production (results not shown).

When recombinant *E. coli* carrying all three plasmids was fed with coumaric acid, methylated apigenin (genkwanin) was synthesized after 24 hours (FIG. 19*d*). However, when the same recombinant culture was fed with caffeic acid, methylated luteolin could not be detected. Overall, after 24 hour fermentation, the recombinant *E. coli* generated 415 µg/L apigenin, 10 µg/L luteolin, and 208 µg/L genkwanin in minimal media. This corresponds to a 2.9% conversion of p-coumaric acid to apigenin, 1.4% conversion of p-coumaric acid to genkwanin and a 0.066% conversion of caffeic acid to luteolin.

Figure 20:
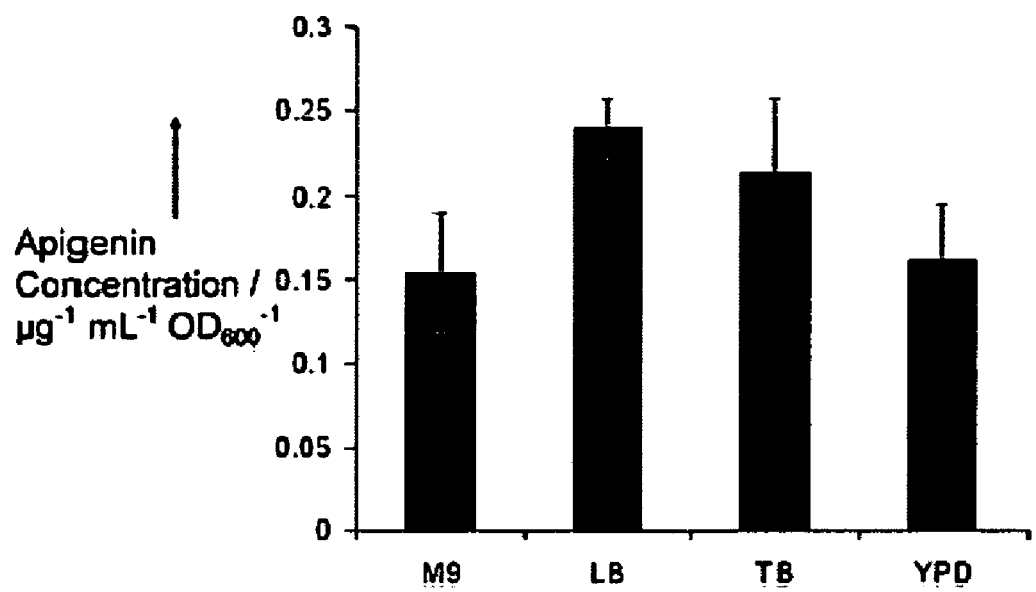
FIG. 20: Apigenin concentration/cell count in extracts from culture supernatant of recombinant BL21Star carrying plasmids pRSF-4CL-FSI and pET-CHI-CHS and grown in various rich and minimal media

In addition to M9 minimal medium, we also tested other media commonly used for microbial cultures, such as minimal salt media, LB, TB, and YPD. As shown in FIG. 20, apigenin is produced in the highest quantity/cell count in rich LB medium within 20 hours and it is 1.6 times higher compared to M9 minimal medium.

Figure 21:
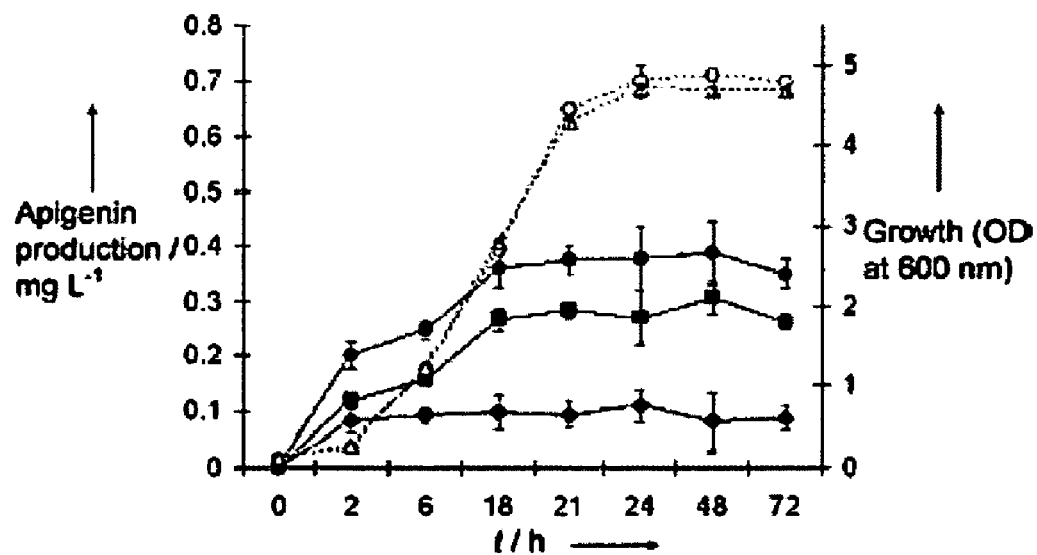
FIG. 21: Growth profile and apigenin production of *E. coli* BL21Star carrying empty vectors pRSFDuet-1 and pETDuet-1 (control) or recombinant BL21Star carrying plasmids pRSF-4CL-FSI and pET-CHI-CHS and grown in M9 minimal medium in the presence of pcoumaric acid. Empty circles and triangles correspond to growth of control and recombinant BL21Star respectively. Black diamonds, black squares and black circles correspond to intracellular, extracellular and total amount of apigenin respectively. Data points are mean values calculated from measurements taken from three independent cultures.

Intracellular accumulation of flavones. We monitored the accumulation of flavones (in particular, apigenin) both intracellularly and extracellularly as a function of time and using M9 minimal medium. As shown in FIG. 21, the expression of the flavone biosynthetic network had no effect on *E. coli* growth and most of the produced apigenin had accumulated within 18 h after the beginning of the fermentation. Surprisingly, significant amount of apigenin was present in the cell extract that accounted for approximately 25% of the total apigenin production (FIG. 21).

EXAMPLE 7

This example demonstrates the synthesis of flavones in yeast.

Materials and Methods

Chemicals and media. Cinnamic acid, p-coumaric acid and caffeic acid were purchased from MP Biomedicals Inc. (Irvine, Calif.). Naringenin was purchased from Sigma-Aldrich (St. Louis, Mo.). Ferulic acid, eriodictyol, apigenin, and luteolin were purchased from Indofine (Hillsborough, N.J.). Flavonoids from plants were extracted according to standard procedures (Harbone, 1998, Phytochemical Methods, A Guide to Modern Technologies, of Plant Analysis, 3$^{rd}$ ed., Springer). Luria Broth (LB) rich medium was purchased from Sigma-Aldrich. YPD *S. cerevisiae* rich medium and SC minimal selection medium with glucose or raffinose and galactose, were prepared (Guthrie et al., 1991, *Method Enzymol*, Academic Press, San Diego, Calif.). Minimal medium with acetate (MA) was prepared according to Verduyn et al., (1992, *Yeast*, 8:501-517) without the antifoaming agent BDH Strains, plasmids and plant materials. All strains and plasmids used are presented in Table 12. Plants were purchased from local nurseries, and sun exposed for a few hours before materials were collected. For mRNA extraction, leaflets of flat leaved *Petroselinum crispum* (parsley) and flower petals, of *Antirrhinum majus* cv. Montego Yellow (snapdragon) and *Catharanthus roseus* (Madagascar periwinkle) were used. Plant materials were quickly frozen with liquid nitrogen and stored at −80° C. until use.

TABLE 12

| Strain or plasmid | Genotype or properties |
| --- | --- |
| *E. coli* TOP 10F'(Invitrogen) | F' {lacI$^q$, Tn10(Tet$^R$)} mcrA (mrr-hsdRMS-mcrBC) 80lacZM15 lacX74 recA1 araD139 (ara-leu)7697 galU galK rpsL (Str$^R$) endA1 nupG |
| *S. cerevisiae* INVSc1 (Invitrogen) | MATa his3D1 leu2 trp1-289 ura3-52 |
| pYES2.1/V5-His-TOPO (Invitrogen) | T/A cloning vector, URA3, ApR |
| YEplac181 (ATCC) | Cloning vector, LEU2, AmpR |
| YCplac22 (ATCC) | Cloning vector, TRP1, AmpR |
| Ycc4c181 | Gal inducible C4H, Pc4CL-2, chs, CHI-A |
| pYES-FSI | Gal inducible PcFSI from parsley |
| pYES-FSII | Gal inducible AFNS2 from snapdragon |
| pYES-CPR | Gal inducible cpr from *C. roseus* |
| pYES-CPR1 | Gal inducible CPR1 from *S. cerevisiae* |
| YC-FSI | Gal inducible PcFSI from parsley |
| YC-FSII | Gal inducible AFNS2 from snapdragon |
| YC-FSII + CPR1 | Gal inducible AFNS2 from snapdragon, CPR1 from *S. cerevisiae* |

DNA manipulations. All DNA manipulations were performed according to standard procedures. Restriction enzymes and T4 DNA ligase were purchased from New England Biolabs and Promega. Reverse Transcription Polymerase Chain Reactions (RT-PCR) were performed using Superscript One-step w/platinum Taq kit (Invitrogen, Carlsbad, Calif.). Polymerase Chain Reactions (PCR) were performed using Roche's Expand High Fidelity PCR system. Flavone synthase I PcFSI cDNA from parsley, flavone synthase II AFNS2 cDNA from snapdragon, *C. roseus* P450 reductase cpr cDNA and *S. cerevisiae* P450 reductase CPR1 cDNA were isolated in our lab based on DNA sequences available in GenBank (accession numbers AY230247, AB028151, X69791 and D13788 respectively). The Qiagen RNeasy MiniKit was used for total RNA isolation from plants or yeast. All amplified genes were initially cloned in *S. cerevisiae* vector pYES2.1/N5-His-TOPO using T/A cloning, according to manufacturer's instructions (Invitrogen), yielding plasmids pYES-FSI, pYES-FSII, pYES-CPR and pYES-CPR1. Transformation of yeast was carried out using the lithium acetate method. In all cases, the absence of undesired mutations introduced during PCR was verified by direct nucleotide sequencing. All primer sequences used are presented in Table 13.

TABLE 13

| Primer | Sequence (5'-3')[a] |  |
|---|---|---|
| PcFSI-F | ATGGCTCCTACAACAATAACCGC - | (SEQ ID NO:55) |
| PcFSI-R | CTAAGCTAAATTTTCATCTGCACTC - | (SEQ ID NO:56) |
| AFNS2-F | ATGTCTACACTTGTCTACAGCACAC - | (SEQ ID NO:57) |
| AFNS2-R | TCACGGTCCGGAGACAACGACCG - | (SEQ ID NO:58) |
| CPR1-F | ATGCCGTTTGGAATAGACAACAC - | (SEQ ID NO:59) |
| CPR1-R | TTACCAGACATCTTCTTGGTATC - | (SEQ ID NO:60) |
| CPR-F | ATGGATTCTAGCTCGGAGAAGTT - | (SEQ ID NO:61) |
| CPR-R | TCACCAGACATCTCGGAGATACCTTC - | (SEQ ID NO:62) |
| Gal1FSI-F (HindIII) | GGAAAAAGCTTGGGACGGATTAGAAGCCGCCGAGCGG | (SEQ ID NO:63) |
| Gal1FSI-R (KpnI) | GGAAAGGTACCGGGCTAAGCTAAATTTTCATCTGCACTC | (SEQ ID NO:64) |
| Gal1FSII-F (BamHI/XbaI) | GGAAAGGATCC/TCTAGAGGGACGGATTAGAAGCCGCCGAGCGG - | (SEQ ID NO:65) |
| Gal1FSII-R (KpnI/SacI) | GGAAAGGTACC/GAGCTCGGGTCACGGTCCGGAGACAACGACCG - | (SEQ ID NO:66) |
| Gal1CPR1 (PstI) | GGAAACTGCAGGGGACGGATTAGAAGCCGCCGAGCGG | (SEQ ID NO:67) |
| Gal1CPR1 (SalI) | GGAAAGTCGACGGGTTACCAGACATCTTCTTGGTATCTAC | (SEQ ID NO:68) |

Construction of plasmids. The flavone biosynthetic genes were introduced in yeast using two co-replicable shuttle vectors YEplac181 and YCplac22, that carry the LEU2 and TRP1 markers respectively, to allow selection of transformants by growth in minimal medium lacking leucine and tryptophan.

Plasmid Ycc4c181, derived from plasmid YEplac181 and carrying cDNA for C4H from *Arabidopsis thaliana*, Pc4cL-2 from parsley, CHI-A and chs from *Petunia×hybrida*.

Plasmid YC-FSI was constructed by amplifying the PcFSI cDNA together with the GAL1 promoter from plasmid pYES-FSI using a forward primer hybridizing to a vector DNA region that lies upstream of the GAL1 promoter and a reverse primer that hybridizes at the end of the cloned cDNA. The GAL1-PcFSI fusion was then inserted into vector YCplac22 between Hind III and Kpn I yielding plasmid YC-FSI. Plasmid YC-FSII was constructed with a similar approach by inserting GAL1-AFNS2 into vector YCplac22 between restriction sites BamH I and Kpn I. Insertion of GAL1-CPR1 between restriction sites Pst I and Sal I of vector YCplac22 and GAL1-AFNS2 between Sac I and Xba I yielded plasmid YC-FSII+CPR1.

In vitro FSII assay. Yeast recombinant strains harboring pYES-FSII, pYES-CPR1, pYES-CPR were cultivated in liquid SC minimal medium lacking uracil (SC-Ura-) with glucose as carbon source overnight at 30° C. For protein expression, the overnight culture was used to inoculate 250 mL SC-Ura-minimal medium with raffinose to an initial absorbance at 600 nm ($Ab_{600}$) of 0.2. When the culture reached an $Ab_{600}$ of 0.8, sterile galactose was added into the culture to a final concentration of 2% to induce protein expression. After 24 hour incubation at 30° C., recombinant yeast cells were harvested and used for microsomal protein preparation. The BCA protein assay kit (Pierce Chemicals, Rockford, Ill.) was used for protein quantification. In vitro apigenin synthesis was performed in 100 μl reaction mixtures containing 0.1 ∝mol of naringenin substrate, NADPH at a final concentration of 1.5 mM, 20 ∝g microsomal preparation of AFNS2, and 50 ∝g microsomal preparation of the P450 reductase (either *C. roseus* CPR or yeast CPR1). The reaction was initiated with the addition of freshly prepared NADPH solution, and proceeded at 25° C. for 2 hours. The reaction products were extracted with an equal volume of ethyl acetate twice and evaporated to dryness under vacuum. Acetonitrile/water (v/v, 1:3) was then added to dissolve the organic compounds for High Performance Liquid Chromatography (HPLC) analysis.

Heterologous expression and fermentation. In order to assemble the two different flavone biosynthetic pathways, recombinant INVSc1 carrying plasmid Ycc4c181G was transformed with YC-FSI, YC-FSII or YC-FSII+CPR1 separately, yielding recombinant strains INV-4G+FSI, INV-4G+FSII, and INV-4G+FSII+CPR1. Yeast colonies harboring both plasmids were selected upon growth on SC agar plates lacking leucine and tryptophan (SC-Leu-Trp-). For flavone fermentation purposes, an individual recombinant yeast colony was grown overnight in 10-mL liquid SC-Leu-Trp-containing glucose at 30° C. with shaking. The following day, a portion of this culture was used to seed the main culture of SC-Leu-Trp-containing galactose and raffinose or MA-Leu-Trp-containing galactose and acetate to an $Ab_{600}$ of 0.4. 0.5 mM of phenylpropanoid acid (cinnamic acid, p-coumaric acid, caffeic acid, ferulic acid) was then added to the main culture, and incubation was carried out at 30° C. with horizontal shaking for a maximum of 92 hours.

For fermentation of INV-4G+FSI, $FeSO_4$, 2-oxoglutaric acid, and sodium ascorbate were added to a final concentration of 0.5 mM. Plasmid stability was checked by isolation from the recombinant strains using Zymoprep I (Zymo Research, Orange, Calif.) every 24 hours, and subsequently used for restriction mapping and PCR analysis Analytical methods. Flavonoids and phenylpropanoid acids were analyzed by HPLC, using an Agilent 1100 series instrument and a reverse phase ZORBAX SB-C18 column (4.6×150 mm), maintained at 25° C. The compounds were separated by elution with an acetonitrile/water gradient, at a flow rate of 1.0 ml/min. The HPLC conditions were as follows (profile 1): 20 to 27% for 45 min, and 27 to 95% for 30 sec (volumetric percentage of acetonitrile). The retention times under these conditions for the standard authentic compounds are: caffeic acid, 2.7 min; p-coumaric acid, 4.7 min; eriodictyol, 18.4 min; luteolin, 20.8 min; naringenin, 30.9 min; apigenin, 33.2 min. Cinnamic acid, pinocembrin and chrysin were separated by elution with an acetonitrile/water gradient, at a flow rate of 1.0 ml/min and under the following conditions (profile 2): 10 to 40% for 10 min, 40 to 60% for 5 min, and 60 to 10% for 2 min. The retention times for cinnamic acid, chrysin and pinocembrin are 12.1 min, 16.0 min and 16.3 min, respectively. Flavanones were detected and quantified by monitoring absorbance at 290 nm. Flavones were detected and quantified at 340 nm.

Calibration curves were obtained with authentic flavanone and flavone solutions of various concentrations.

Results

In order to explore this possibility in the case of AFNS2 and in order to select the most effective P450 reductase, we investigated the role of C. roseus P450 reductase CPR and S. cerevisiae P450 reductase CPR1 in optimizing AFNS2 activity in vitro. For this purpose, microsomal proteins of recombinant yeast individually expressing AFNS2, CPR1, and CPR were prepared. The activity of AFNS2 was investigated by quantifying the conversion of naringenin to apigenin in the presence of NADPH, and either CPR1 or CPR preparation. An approximately two-fold increase in the amount of naringenin produced was observed when either reductase enzyme preparation was provided compared to the control (no reductase) (Table 14).

However, the conversion of naringenin into apigenin by AFNS2 was 30% higher in the presence of CPR1 than when CPR was used. Based on these results, we concluded that overexpression of yeast CPR1 enhances the performance of AFNS2 more efficiently and CPR1 was chosen for further investigation.

TABLE 14

| Incubation time (hour) | Amount of apigenin produced (nmoles) | | | Ratio | |
|---|---|---|---|---|---|
| | AFNS2 | AFNS2 + CrRed | AFNS2 + ScRed | (a) | (b) |
| 0.5 | 0.05 | 0.12 | 0.13 | 2.40 | 2.60 |
| 1 | 0.19 | 0.23 | 0.35 | 1.21 | 1.84 |
| 2 | 0.28 | 0.40 | 0.53 | 1.43 | 1.89 |

Figure 22:
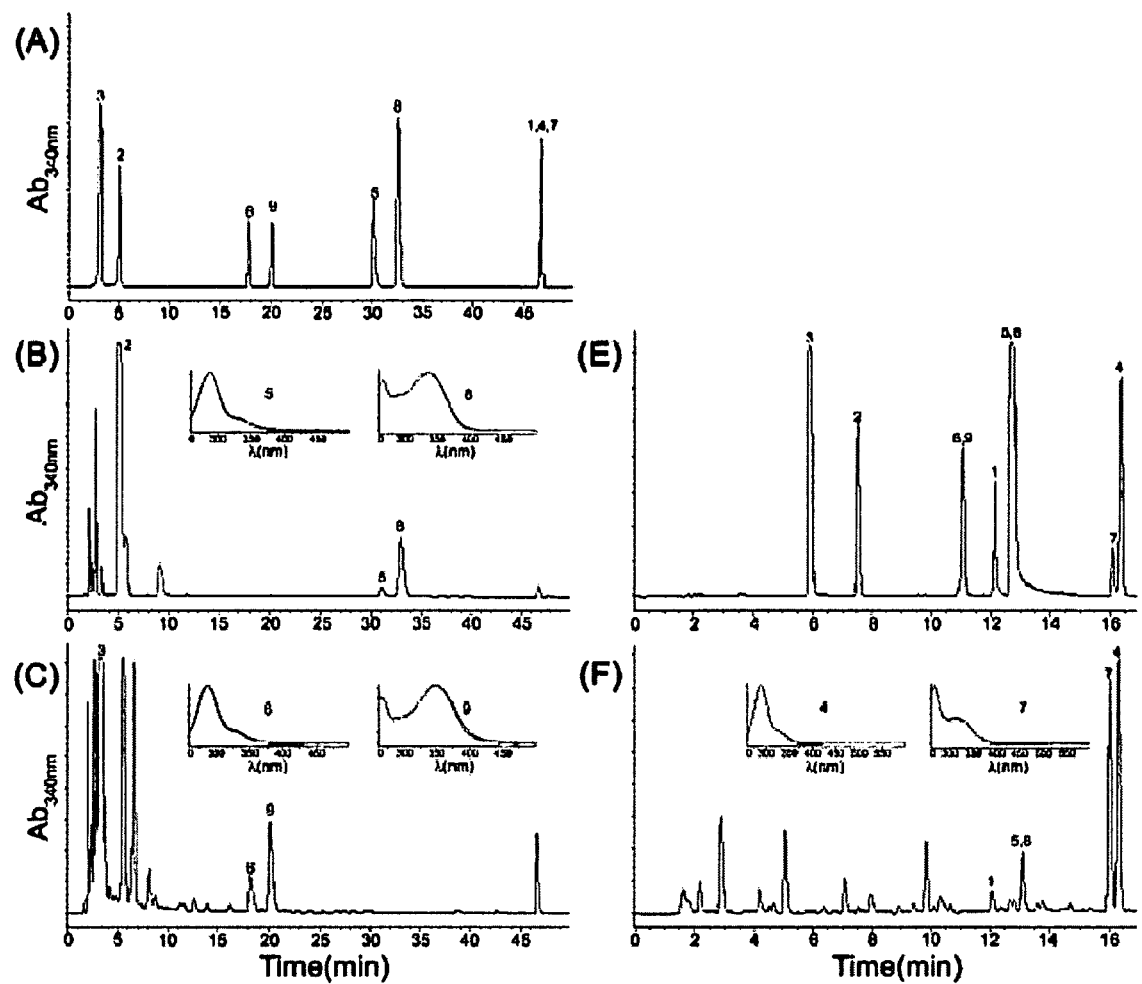
FIG. 22: HPLC analysis of recombinant strains INV-4G+FSI or INV-4G+FS2+CPR1 fermentation. A. Standard compounds separated according to HPLC profile 1: cinnamic acid (1), p-coumaric acid (2), caffeic acid (3), pinocembrin (4), naringenin (5), eriodictyol (6), chrysin (7), apigenin (8), luteolin (9); B. Apigenin and naringenin produced from the recombinant strains when fed with p-coumaric acid; C. Luteolin and eriodictyol produced from the recombinant strains when fed with caffeic acid; D. UV-absorbance spectra of authentic compounds; E. Standard compounds separated according to HPLC profile 2; F. Chrysin, apigenin, pinocembrin and naringenin produced from recombinant strain INV-4G+FSI fed with cinnamic acid. The insets show the UV-Vis spectra of flavonoid substances produced from the recombinant strains superimposed with that of the authentic compounds.
Figure 22:
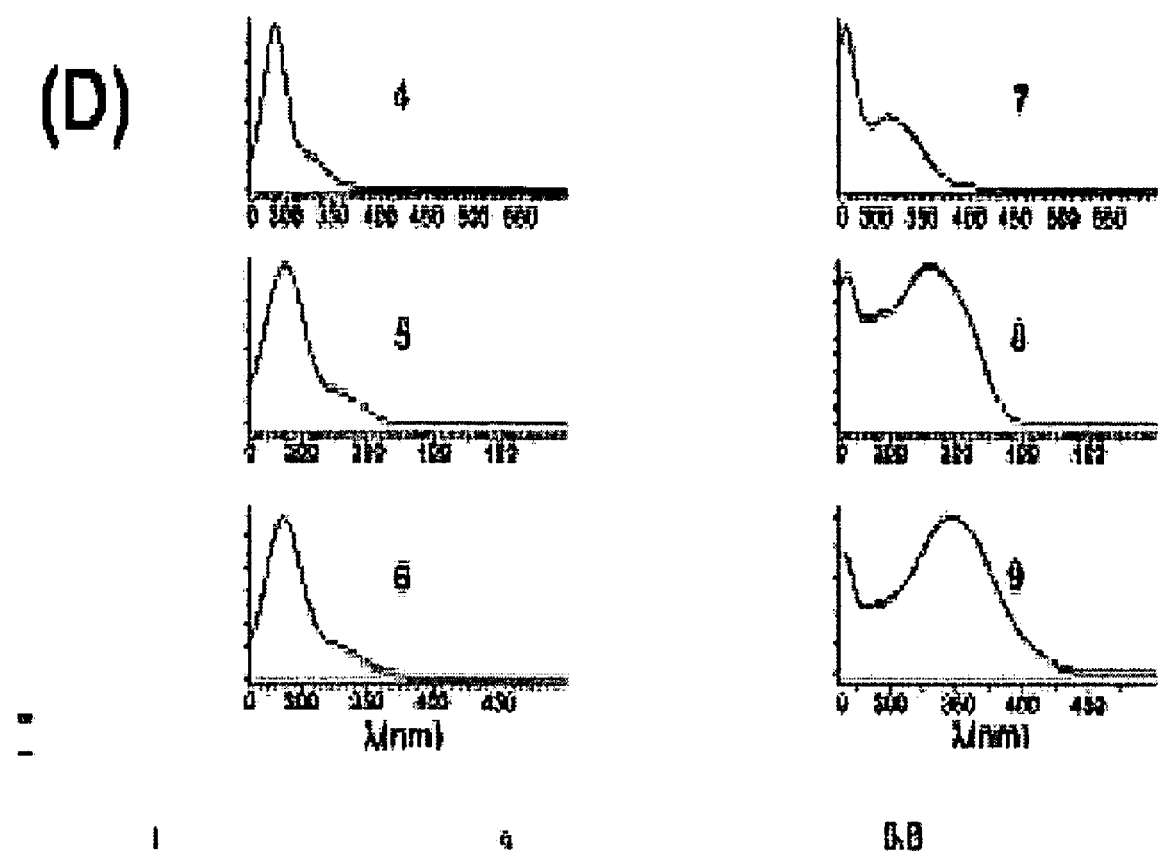

S. cerevisiae strain INVSc1 carrying Ycc4c181 was transformed with YC-FSI, YC-FSII, or YC-FSII+CPR1, generating recombinant strains INV-4G+FSI, INV-4G+FSII and INV-4G+FSII+CPR1 respectively. We investigated the ability of these three recombinant strains to produce flavones when phenylpropanoid acid precursors were supplemented in the SC-Leu-Trp-culture media. The expression of the recombinant proteins was induced with galactose, and glucose was replaced with raffinose as carbon source because raffinose, unlike glucose, does not repress the GAL1 promoter (9). After 46 hours, the fermentation products were extracted from the culture media, and analyzed using HPLC. The identity of the flavonoid products was determined by co-chromatography, matching UV-absorbance spectra (FIG. 22D) and retention time with authentic standard compounds (FIGS. 22A, 22E). In general, flavonoid accumulation occurred mostly in culture media with intracellular flavonoid accumulation accounting for less than 10% of the overall flavonoid production. All recombinant strains produced the flavone apigenin (FIG. 22B), when the non-hydroxylated cinnamic acid was utilized as the precursor phenylpropanoid acid. Additionally all recombinant strains were able to metabolize caffeic acid to its corresponding flavone luteolin and corresponding flavanone eriodictyol (FIG. 22C). Chrysin however was only detected in INV-4G+FSI cultures (FIG. 22F). The flavanones pinocembrin (non-hydroxylated) and naringenin (monohydroxylated) were produced by all strains. Incorporation of CPR1 into the flavone biosynthetic pathway with AFNS2 (strain INV-4G+FSII+CPR1) resulted in apigenin and luteolin production increase of 62% and 11% respectively, when compared to that of INV-4G-FSII (Table 15). Supplemental feeding of ferulic acid did not result in flavanone or flavone production (results not shown).

TABLE 15

| | Production($\mu gL^{-1}Ab_{600}^{-1}$) | | |
|---|---|---|---|
| | INV-4G + FSI | INV-4G + FSII | INV-4G + FSII + CPR1 |
| Chrysin | 24.2 ± 2.2 | 0 | 0 |
| Apigenin | 22.6 ± 4.5 | 28.6 ± 6.9 | 46.4 ± 7.3 |
| Luteolin | 92.8 ± 44.5 | 148.4 ± 41.7 | 164.9 ± 19.4 |
| Pinocembrin | 6.6 ± 0.5 | 70.3 ± 19.1 | 87.3 ± 19.1 |
| Naringenin | 3.7 ± 2.0 | 4.4 ± 2.2 | 8.4 ± 2.2 |
| Eriodictyol | 535.7 ± 108.1 | 500.4 ± 132.1 | 357.5 ± 11.3 |

Effect of carbon source on flavonoid production. In an effort to further optimize flavonoid biosynthesis, we investigated the role of carbon source, and more specifically acetate, in flavone production.

Figure 23:
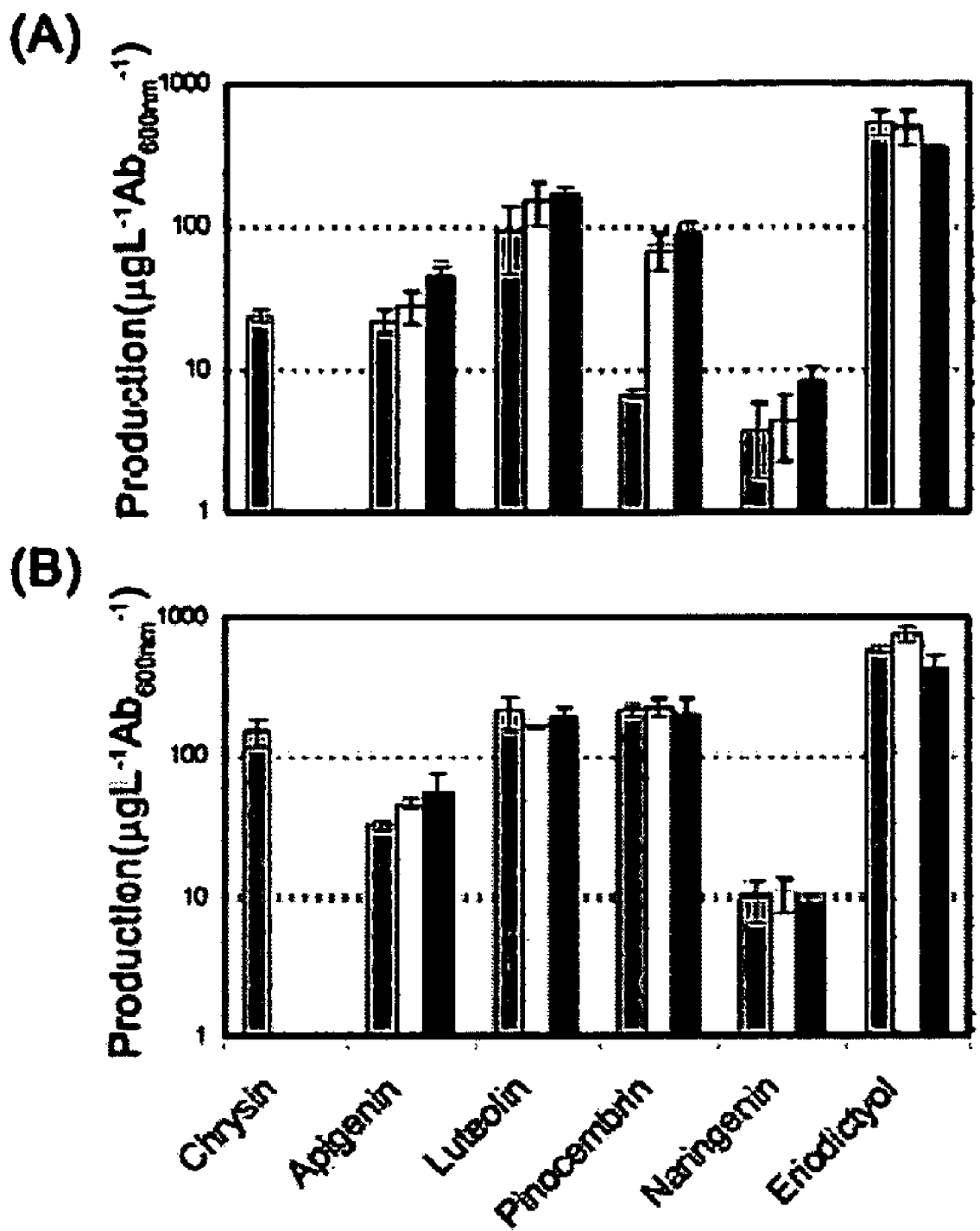
FIG. 23: Flavonoid production by recombinant yeast strains. A. Recombinant yeast strains grown in SC-Leu⁻Trp⁻ minimal medium with raffinose as carbon source; B. Recombinant yeast strains grown in MA-Leu⁻Trp⁻ minimal medium with acetate as carbon source. Grey bars: INV-4G+FSI; white bars: INV-4G+FSII; black bars: INV-4G+FSII+CPR1. Products were extracted from culture media after 46-hour fermentation at 30° C. Chrysin, apigenin, pinocembrin, and naringenin were simultaneously derived from cinnamic acid. Caffeic acid supplementation resulted in eriodictyol and luteolin.

The recombinant yeast strains were grown in MA-Leu-Trp-minimal medium with acetate as sole carbon source. The fermentation resulted in a general increase in flavonoid production (FIGS. 23A, 23B). More specifically, in the case of INV-4G+FSI, flavone and flavanone concentration per cell count increased 3-fold and 1.5-fold respectively when MA-Leu-Trp-minimal medium with acetate as carbon source rather than SC minimal medium with raffinose as carbon source was utilized. In the case of INV-4G+FSII+CPR1, fermentation in MA media increased flavone and flavanone concentration per cell count 1.2-folds and 1.4-folds respectively compared to SC minimal medium with raffinose. The flavone and flavanone concentrations per cell count obtained with acetate as carbon source are presented in Table 16.

TABLE 16

| | Production($\mu gL^{-1}Ab_{600}^{-1}$) | | |
|---|---|---|---|
| | INV-4G + FSI | INV-4G + FSII | INV-4G + FSII + CPR1 |
| Chrysin | 148.8 ± 34.0 | 0 | 0 |
| Apigenin | 33.2 ± 2.5 | 47.6 ± 4.4 | 56.6 ± 17.0 |
| Luteolin | 210.5 ± 60.1 | 160.7 ± 4.1 | 191.0 ± 29.6 |
| Pinocembrin | 213.3 ± 20.5 | 221.3 ± 33.6 | 193.9 ± 59.6 |
| Naringenin | 9.8 ± 3.3 | 10.6 ± 2.9 | 9.0 ± 1.2 |
| Eriodictyol | 576.2 ± 27.8 | 752.2 ± 82.6 | 423.3 ± 111.2 |

Overall, these results demonstrate that acetate is a better carbon source for flavonoid biosynthesis purposes and that flavone production from recombinant yeast can be a competitive alternative to the current method of plant extraction. To further confirm this, we extracted apigenin and luteolin from parsley leaves (where flavones are produced via the FSI route) and snapdragon petals (where flavones are produced via the FSII route). Approximately 3 mg of apigenin and 0.01 mg of luteolin per mg of leaves were extracted from parsley and 0.2 μg of apigenin and 0.05 μg of luteolin per mg of petals were extracted from snapdragon. In both cases, no chrysin was identified.

Figure 24:
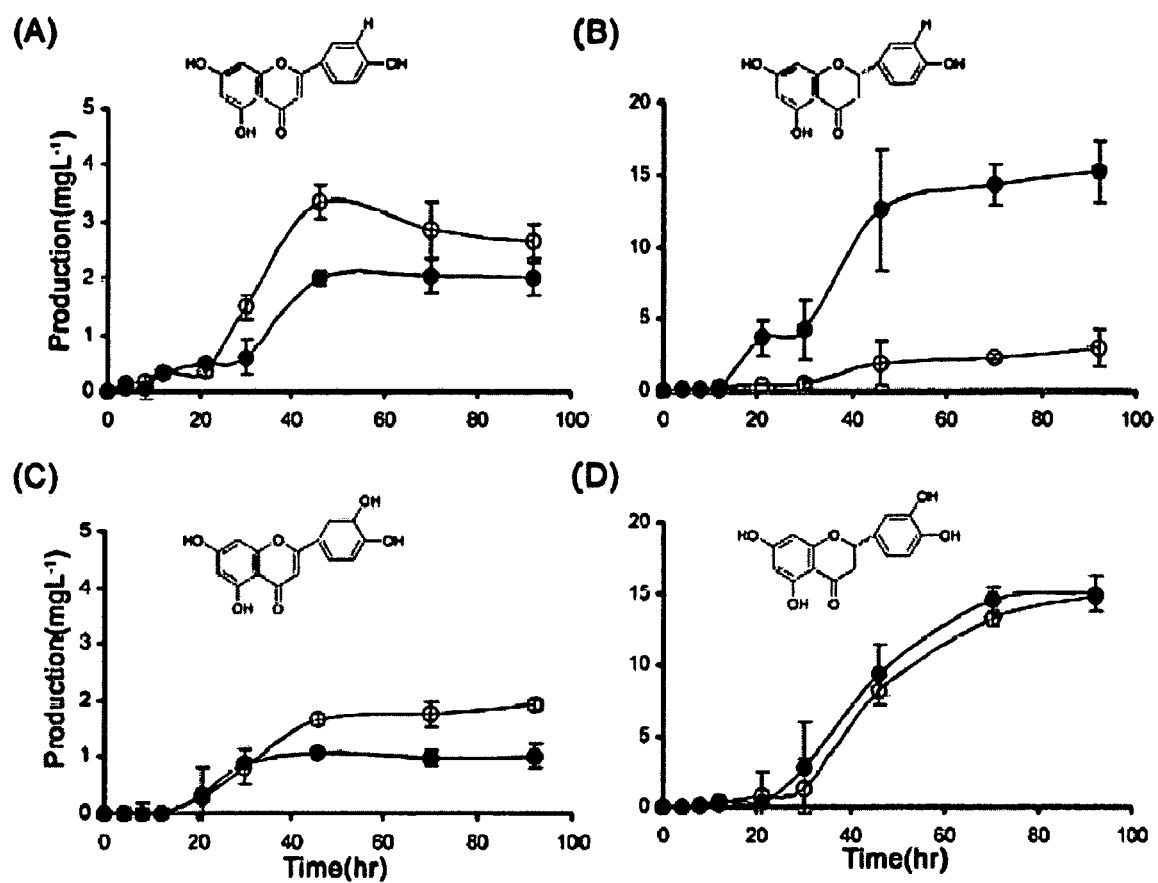
FIG. 24: Flavone and flavanone biosynthesis from two yeast recombinant strains. A. apigenin from p-coumaric acid; B. naringenin from p-coumaric acid; C. luteolin from caffeic acid; D. eriodictyol from caffeic acid. Open circle: INV-4G+FSI. Closed circle: INV-4G+FSII+CPR1. All fermentations were carried out in SC-Leu⁻Trp⁻ minimal medium with raffinose as carbon source.

Regulation of flavanone biosynthesis by flavones. The yeast recombinant strains provided an opportunity to further investigate the two alternative routes for flavone biosynthesis. In order to bypass C4H (another membrane bound protein in the pathway) p-coumaric acid, instead of cinnamic acid was fed to yeast strains INV-4G-FSI and INV-4G-FSII+ CPR1 in SC-Leu-Trp-minimal medium. One interesting observation was that naringenin accumulated about six times lower in the yeast strain expressing FSI (2.4 mg/L) that produced more apigenin (3 mg/L) than in the strain expressing FSII (14 mg/L) that produced 2 mg/L of apigenin (FIGS. 4A, 4B). Feeding experiments with caffeic acid as the phenylpropanoid precursor resulted in similar amounts of luteolin and eriodictyol biosynthesis in both INV-4G+FSI (1.8 mg/L luteolin; 12 mg/L eriodictyol) and INV-4G+FSII+ CPR1 (1 mg/L luteolin; 13 mg/L eriodictyol) (FIGS. 24C, 24D).

Figure 25:
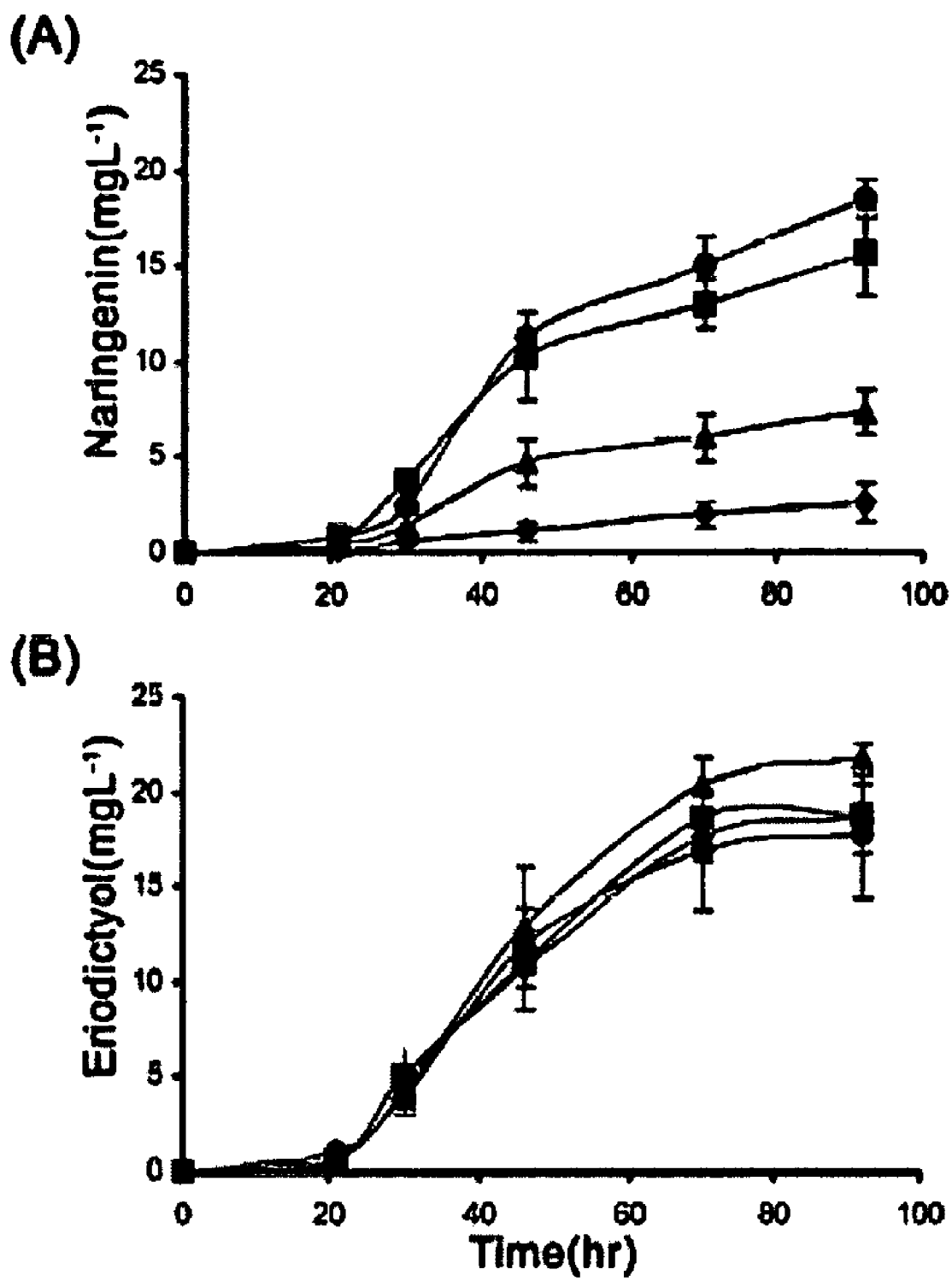
FIG. 25: Flavanone production by yeast recombinant strain INV-4G. (A); naringenin produced from p-coumaric acid in the presence of varying concentrations of apigenin. (B); eriodictyol produced from caffeic acid in the presence of varying concentrations of luteolin. Square: 1 mg/L of flavone; triangle: 3 mg/L of flavone; diamond: 10 mg/L of flavone; circle: control (no flavone).

Considering that INV-4G+FSI produced more apigenin than INV-4G+FSII+CPR1, we tested the possibility that flavanone biosynthesis is feedback-inhibited by apigenin. For this purpose, recombinant yeast strain carrying only the four flavanone biosynthetic genes (INV-4G) was created by simultaneously inserting YP-4G and empty YCplac22 plasmid. INV-4G was then tested for the ability to generate naringenin from coumaric acid, in the presence of apigenin. As shown in FIG. 25A, INV-4G produced naringenin with varying efficiency when apigenin was added into the culture medium. In the presence of 1 mg/L apigenin, the production of naringenin at stationary phase was reduced by 14%. A more prominent effect was observed in the presence of 3 mg/L and 10 mg/L apigenin, which accounted for approximately 60% and 85% production decline. It is important to note that in all cases, naringenin production decrease did not result from lower biomass production, as all cultures displayed similar growth profiles (results not shown).

The efficiency of eriodictyol production from caffeic acid by INV-4G in the presence of varying luteolin concentrations was also tested. Unlike apigenin, luteolin did not regulate (feedback inhibited) flavanone biosynthesis in yeast (FIG. 25B). Overall, these data indicated that apigenin acts as a feed-back inhibitor of its own biosynthesis in a dose dependent manner.

EXAMPLE 8

This example describes the production of flavan-4-ols

Materials And Methods

Plant Materials and cDNA Clones

Plant tissues used for RNA extraction included red spathe and red spadix from *Anthurium andraeanum*, flower petals from *Rosa hybrida* cv. "minirose", petals from *Lilium hybrid* cv. "Star Gazer", flowers and fruits (at various growth stages) from strawberry (*Fragaria ananassa*) and tomato young leaves. Plant material was quickly frozen in liquid nitrogen after harvesting and stored in −70° C. until further use. DFR cDNA of common morning glory (*Ipomoea purpurea*) line KK/FP-39 and *Ipomoea nil* were kind gifts from Dr. Shigeru Iiida, National Institute for Basic Biology, Japan.

Chemicals

[$^{14}$C]-labeled flavonoids used in the present study were synthesized as described in (Fischer et al. 1988) using different recombinant proteins obtained by heterologous expression of the cDNA clones in yeast. Products were analyzed using thin layer chromatography (TLC).

DNA Manipulations

Total RNA from plant material was isolated using RNeasy Plant Mini Kit (Qiagen, USA) according to manufacturer's instructions. Reverse transcription and end-to-end PCR of DFR structural genes were performed using SuperScript™ One-Step RT-PCR with Platinum® Taq (Invitrogen, USA). DFR genes from *A. thaliana, I. nil* and *I. purpurea* were amplified from cDNA clones using Expand High Fidelity$^{Plus}$ PCR System (Roche, Germany). The primer set for each plant DFR is listed in Table 17. The accession numbers used for PCR primer design were: AY232494 for *A. andraeanum*, D85102 for *R. hybrida*, AB058641 for *L. hybrid*, AF029685 for *F. ananassa*, AB033294 for *A. thaliana*, AB018438 for *I. purpurea* and AB006792 for *I. nil*. In all cases, the PCR product was cloned into TOPO T/A cloning vector pTrcHis2-TOPO (Invitrogen), under the strong, IPTG-induced trc promoter. All cloned dfr cDNAs were directly sequenced.

TABLE 17

| Primer | Forward Sequence (5'-3')[a] | Reverse Sequence (5'-3')[b] |
|---|---|---|
| A. andraeanum | ATGATGCACAAGGGCACCGTGTG (SEQ ID NO:69) | TCAATGGCCGTTGTCTTGCCCGGTG (SEQ ID NO:70) |
| A. thaliana | ATGGTTAGTCAGAAAGAGACCGTG (SEQ ID NO:71) | CTAGGCACACATCTGTTGTGCTAGC (SEQ ID NO:72) |
| B. japonicum | ATGAGCATTGTTCTGGTCACGG (SEQ ID NO:73) | TCACGCCCTGACCAGGCCAAG (SEQ ID NO:74) |
| F. ananassa | ATGGGGTTGGGAGCAGAATCC (SEQ ID NO:75) | CTAACCAGCCCTGCGCTTTTCAG (SEQ ID NO:76) |
| I. nil | ATGGTGGACGGTAATCATCCTC (SEQ ID NO:77) | TCAAGGTTTTAAGGGCACTACC (SEQ ID NO:78) |
| I. purpurea | ATGGTGGACGGTAATCATCCTC (SEQ ID NO:79) | TCAAGCTTTTAAGGGCACTACC (SEQ ID NO:80) |
| L. hybrid | ATGGAGAATGCGAAAGGACCCG (SEQ ID NO:81) | TTACTGAAGAGCAACGGAGACTTG (SEQ ID NO:82) |

TABLE 17-continued

| Primer | Forward Sequence (5'-3')[a] | Reverse Sequence (5'-3')[b] |
|---|---|---|
| R. hybrida | ATGGCATCGGAATCCGAGTCCGTT (SEQ ID NO:83) | TTAGCCTGTGACTTTGACACGGACG (SEQ ID NO:84) |
| Synechocystis sp. PCC 6803 | ATGGAGGTCAATCACTGGATAGCC (SEQ ID NO:85) | TTATTGGGTCTTAACGTAGCCATGG (SEQ ID NO:86) |

Recombinant Protein Expression

Vector pTrcHis2-TOPO, either empty (control) or harboring the various cDNA sequences, was transformed into *E. coli* strain TOP10F' (Invitrogen). Individual colonies were grown overnight in 3-mL Luria-Broth (LB) cultures with 100 µg/mL Ampicillin. The seed culture was used the following day to start a 50-mL main culture with an initial absorbance at 600 nm ($A_{600}$) of 0.05. The main culture was left to grow at 37° C. until $A_{600}$ reached 0.5-0.8. At that point, the inducer IPTG (isopropyl β-thiogalactoside) at a final concentration of 2 mM was added and the culture was left to grow for 4 hours at 30° C. Cells were harvested by centrifugation, resuspended in 5 mL of buffer (0.1 M $K_2HPO_4$/$KH_2PO_4$, pH 6.5), and lysed by either sonication or glass beads.

Thin Layer Chromatography (TLC) Analysis of DFR In Vitro Assays

In vitro DFR and FNR enzymatic reactions were performed using 186 Bq of radiolabeled substrate and incubation was performed at 30° C. for 30 min-1 hour for DFR tests, and 30 min-2.5 hours for FNR tests. Ethyl acetate extraction was performed (twice) at the end of the incubation period, with 100 µL ethyl acetate. The organic phase was analyzed on a precoated TLC cellulose plate (Merck, Germany). The products, leucoanthocyanins and flavan-4-ols were separated from the respective substrates, dihydroflavonols and flavanones by chromatography in chloroform:acetic acid:water (10:9:1) system. The detection and quantification of radioactivity was performed using Fuji BAS 1000 Bio-Imaging Analyzer. Protein content was determined using Lowry procedure with crystalline BSA as a standard. In vitro reaction products were identified by a previously published $R_f$ values from in vitro reactions using heterologously expressed DFR proteins from *Malus domestica* (Punyasiri, et al., 2004, Arch. Biochem. Biophys., 431:22-30). Using TLC chromatography with chloroform: acetic acid:water (10:9:1), the $R_f$(×100) values for various flavonoids are DHK: 68; DHQ: 35; DHM: 11; NAR: 93; ERI: 61; LPg: 18; LCy: 8; LDp: 14; Apf: 45; Ltf: 18.

High Performance Liquid Chromatography (HPLC) Analysis of Fermentation Products of Recombinant *E. coli*

Shake-flask experiments were performed to test for the flavanone reductase activity of *A. andraeanum* DFR towards various commercially available flavanones, such as flavanone, 7-hydroxyflavanone, hesperetin, 5,7-dimethoxyflavanone, NAR and ERI. Seed cultures of recombinant *E. coli* harboring *Anthurium* DFR were grown in LB with 100 µg/mL ampicillin. After 24 hours, the preinoculum was used to seed a 50-mL main culture which was incubated at 37° C. until $A_{600}$ reached 0.5. IPTG and flavanone substrates were added at a final concentration of 2 mM and 0.4 mg/mL respectively, and incubation procceeded at 30° C. for 24 hours before harvesting. Flavonoid products in the culture supernatant were extracted twice with an equal volume of ethyl acetate. The organic solvent was collected and evaporated using a rotary evaporator, and the residue was dissolved in water.

The products were analyzed by HPLC using an Agilent HPLC 1100 series instrument with a diode array detector. HPLC was carried out using a reverse phase ZORBAX SB-C18 column (diameter 4.6 mm×150 mm) using an acetonitrile (solvent A) and water (solvent B) gradient at a flow rate of 1 ml/min. The HPLC program conditions used were as follows: 10% to 40% A (0-10 min), 40% to 60% A (10-15 min), 60% A (15-20 min). Absorbance at 280 nm was monitored in all cases. Retention times of the flavan-4-ols were compared to authentic 2,4-cis-flavan-4-ol and 2,4-cis-7-hydroxyflavan-4-ol standards prepared as previously described (Pouget et al., 2000, Tetrahedron, 56:6047-6052). The UV maximum for the various flavan-4-ols synthesized were: 276 nm for 2,4-cis-flavan-4-ol; 275 nm for 2,4-trans-flavan-4-ol; 281 nm for 2,4-cis-7-hydroxyflavan-4-ol; and 279 nm for 2,4-trans-7-hydroxyflavan-4-ol.

Results

Molecular Cloning of Plant DFR into an *E. coli* Expression Vector and Protein Expression We amplified full-length cDNA of various plant DFR open reading frames by PCR and RT-PCR using sequence information available in Genbank. In the case of *A. andraeanum*, the RT-PCR produced a cDNA fragment corresponding to dfr using RNA extracted from either the red spathe or the red spadix as template. In the case of strawberry, dfr cDNA was amplified only from RNA isolated from fruit (at all different developmental stages examined) but not from flower.

The PCR products were cloned into the pTrcHis2-TOPO *E. coli* expression vector and sequenced in both directions. In the case of the amino acid sequence of DFR from *Lilium hybrid* cv. "Star Gazer", 6 and 31 amino acids were different compared to the sequences of cvs. "Acapulco" and cv. "Montreux" respectively. In the case of the amino acid sequence of DFR isolated from *I. purpurea* one amino acid difference at position 234 was identified compared to the sequence available in GenBank (for line KK/FP-39).

Biochemical Properties of the DFR Recombinant Enzymes

Figure 26:
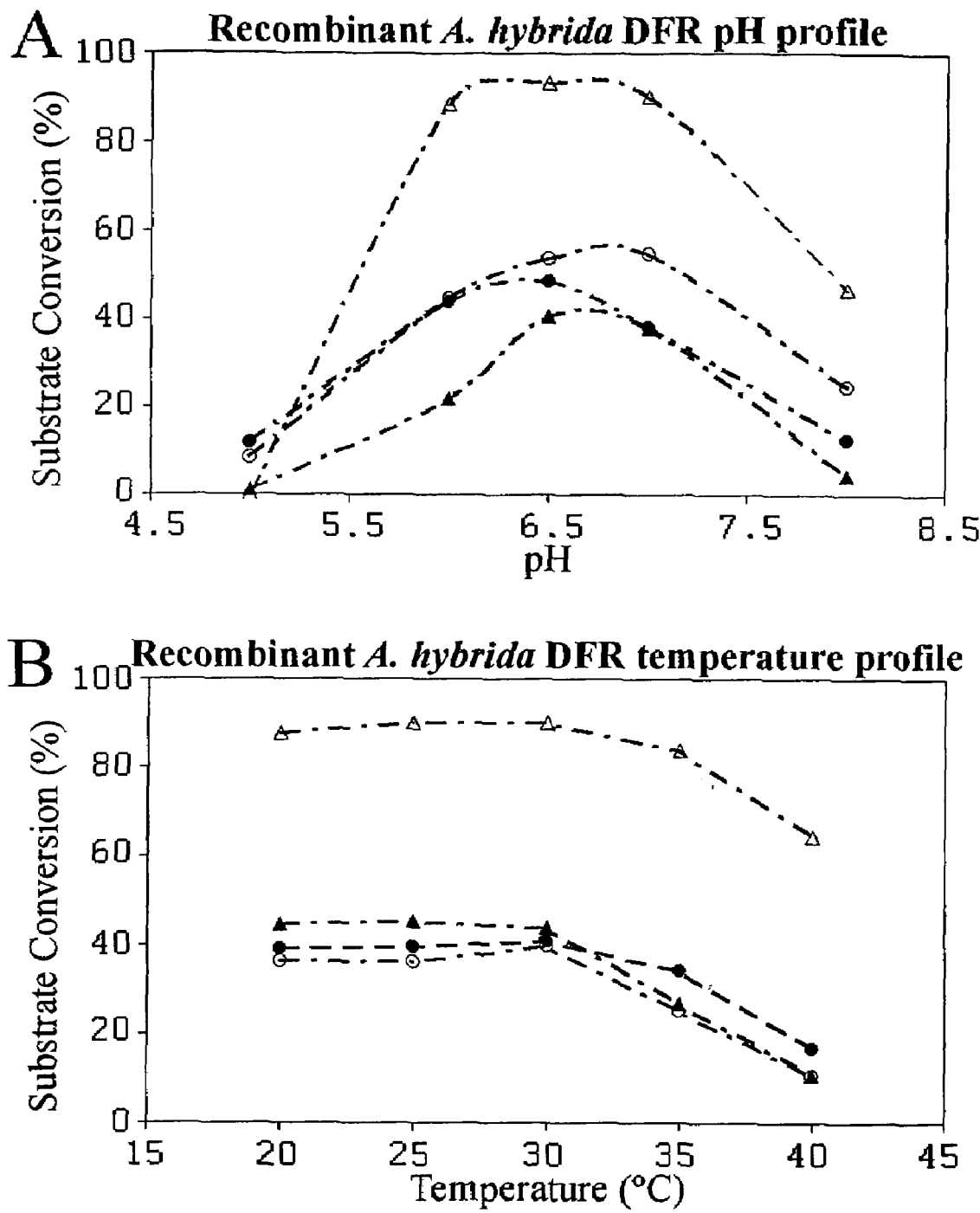
FIG. 26: The reaction dependency of *Anthurium* DFR on pH and temperature. A) Temperature profile, B) pH profile. Substrates: DHK (open triangle); NAR (closed triangle); DHQ (open circle); ERI (closed circle).

Recombinant *Anthurium* demonstrated maximum in vitro activities towards dihydroflavonols and flavanones at pH values close to normal (6-7) (FIG. 26A). This was the optimum pH region for the other DFR enzymes as well. The optimal temperature conditions for all substrates was within the region of 25-30° C. (FIG. 26B).

The in vitro reactions were performed using the optimal conditions (pH 6.5, 30° C.). For each substrate tested, all reactions with recombinant DFRs resulted in a single product, identified with known $R_f$ values as indicated in Section 2.5. No products were formed when using crude extract from E. coli harboring empty vector. DHQ and DHM were accepted as substrates by all seven recombinant enzymes, however, only the recombinant DFR enzymes derived from *A. andraeanum, A. thaliana, I. nil, R. hybrida*, and *F. ananassa* were able to catalyze the formation of LPg (Table 18). Recombinant DFRs from *A. andraeanum* and strawberry utilized DHK very efficiently while recombinant DFRs from *A. thaliana, I. nil*, and *R. hybrida* showed significantly lower activity for DHK. In addition, no LPg could be detected in assays using DFR from *I. purpurea* and *L. hybrid* even when the reaction period was extended and the amount of protein was increased up to 100 μg. In all cases, substrate specificity appeared to be independent of temperature or pH changes. Interestingly enough, the two DFR recombinant enzymes with the highest specific activities towards DHK, namely the *A. andraeanum* and *F. ananassa*, had the amino acid serine and alanine, respectively at position 133 (numbering of amino acid is based on *Anthurium* DFR sequence) (FIG. 4).

The specific activities of the recombinant enzymes towards DHK and DHQ are summarized in Table 18.

TABLE 18

| Recombinant | Specific activity (pkatal/mg) | | | | |
|---|---|---|---|---|---|
| DFR | DHX | DHQ | DHM | NAR | ERI |
| A. andraeanum | 21 | 1.4 | 1.4 | 0.7 | 0.8 |
| A. thaliana | 0.002 | 1.3 | 1.0 | 0 | 0.6 |
| I. nil | 0.3 | 1.3 | 1.5 | 0.3 | 0.6 |
| I. purpurea | 0 | 1.2 | 1.5 | 0 | 0.6 |
| L. hybrid | 0 | 1.3 | 1.2 | 0 | 0.6 |
| R. hybrida | 0.4 | 1.0 | 1.3 | 0.4 | 0.7 |
| F. ananassa | 14 | 1.2 | 1.4 | 0.5 | 0.6 |

FNR Activities of the Recombinant DFR Enzymes

Figure 27:
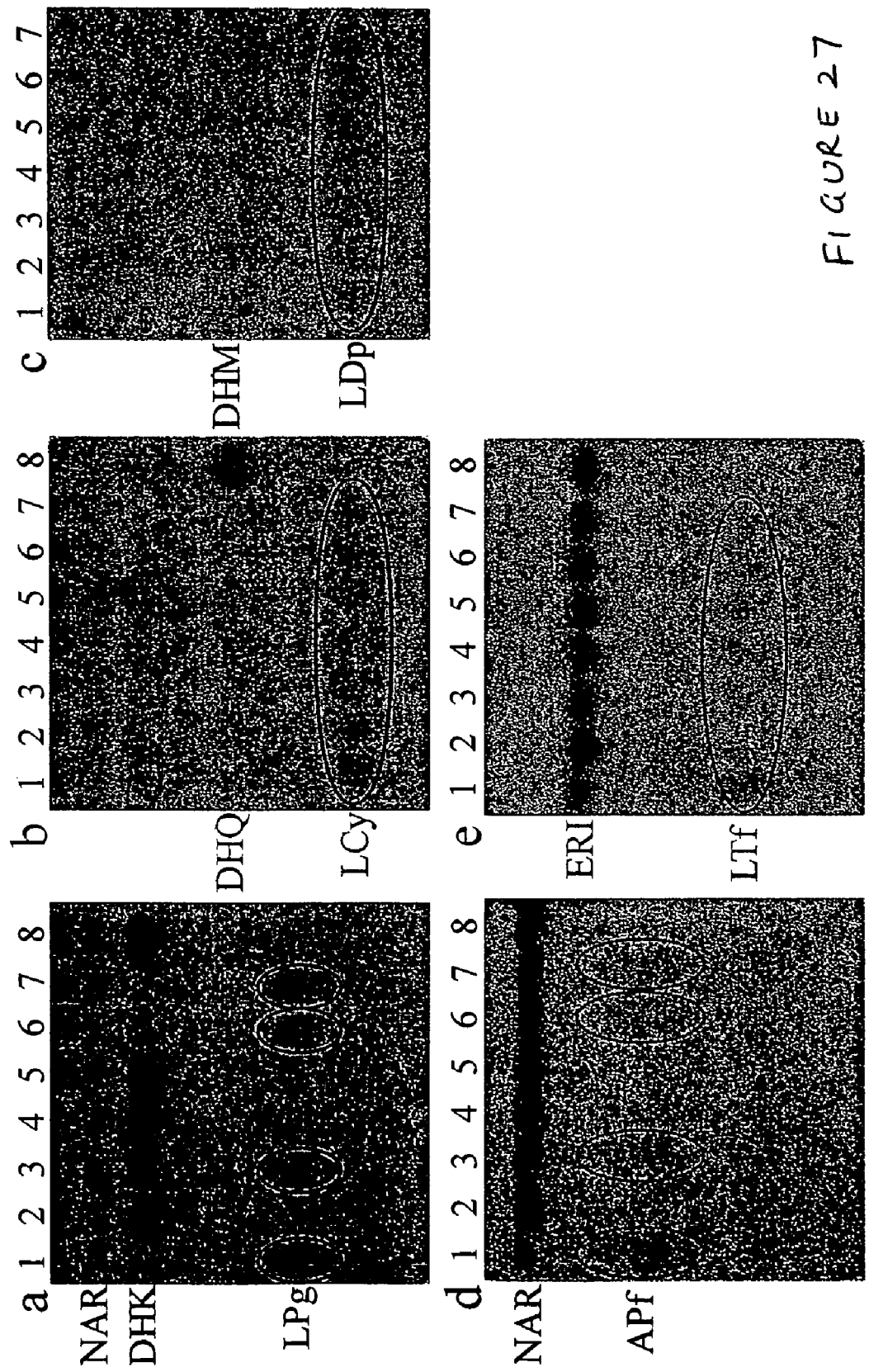
FIG. 27: TLC analysis of in vitro reactions of various recombinant DFRs: 1. *A. andraeanum*, 2. *A. thaliana*, 3. *I. nil*, 4. *I. purpurea*, 5. *L. hybrid*, 6. *R. hybrida*, 7. *F. ananassa*, 8. control: crude extract of *E. coli* harboring empty vector pTrcHis2.

All functionally expressed recombinant DFR enzymes also demonstrated FNR activities. ERI served as a universal substrate for all DFR enzymes, as LTf, the product of ERI reduction, was detected in all assays. However, when NAR was used as the substrate, APf was only detected in reactions with recombinant DFR enzymes that were also able to efficiently reduce DHK, namely from *A. andraeanum, I. nil, R. hybrid*, and *F. ananassa* (FIG. 27). Overall, these assays indicated that flavanones were not as efficiently accepted as dihydroflavonols by DFR enzymes (enzyme activities presented in Table 18). They also demonstrate that FNR activity is a global DFR property.

Figure 28:
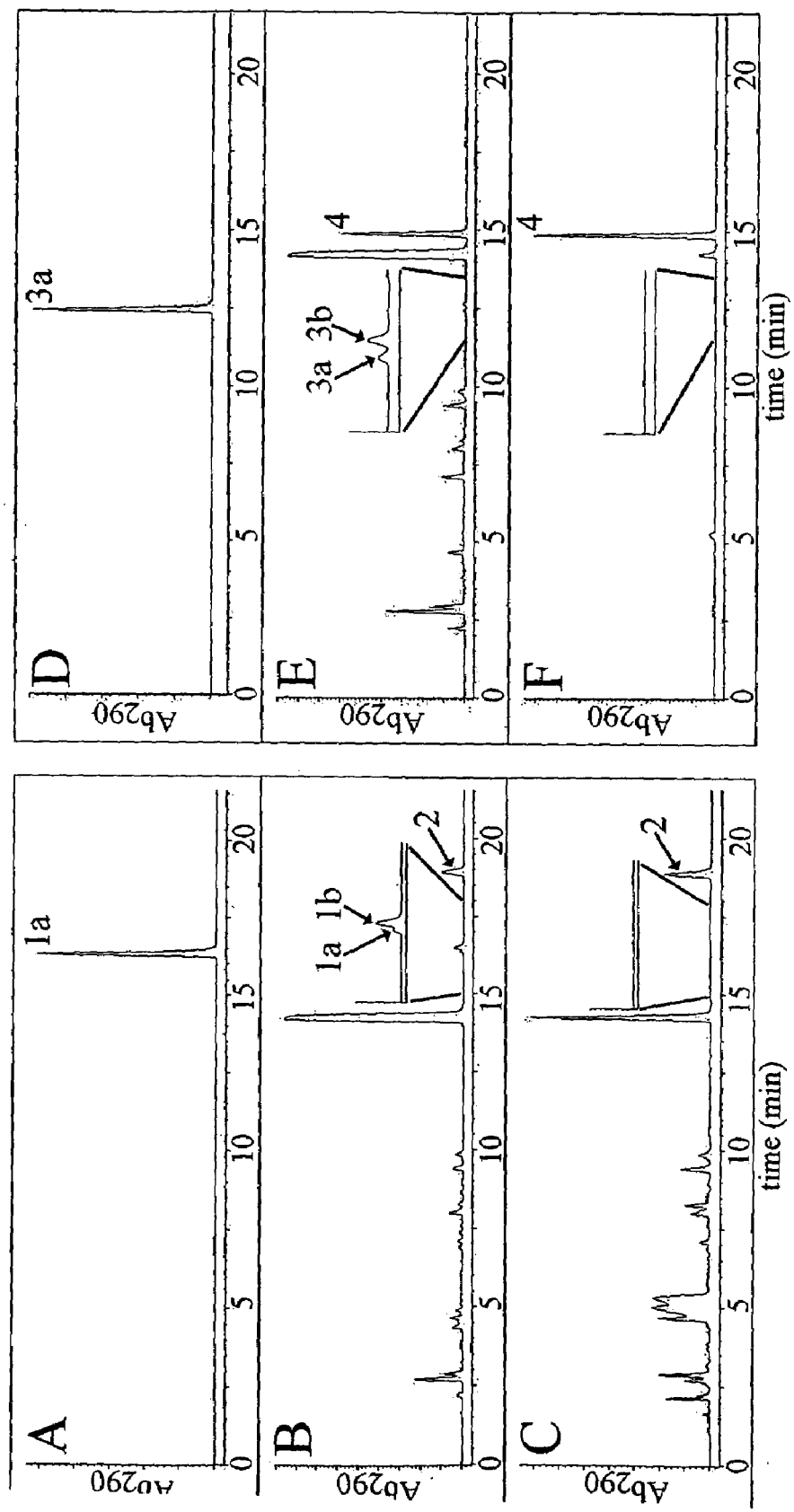
FIG. 28: HPLC analysis at 290 nm of fermentation extracts from recombinant *E. coli* culture expressing *Anthurium* DFR. Fermentation was performed using LB medium supplemented with various flavanones. A) Standard compound 2,4-cis-flavan-4-ol (1a). B) Recombinant *E. coli* produced 2,4-cis-flavan-4-ol (1a) and 2,4-trans-flavan-4-ol (1b) using flavanone (2) as the substrate. C) No fermentation product using *E. coli* harboring empty pTrcHis2 vector when flavanone (2) was provided. D) Standard compound 2,4-cis-7-hydroxyflavan-4-ol (3a). E) Recombinant *E. coli* produced 2,4-cis-7-hydroxyflavan-4-ol (3a) and, 4-trans-7-hydroxyflavan-4-ol (3b) using 7-hydroxyflavanone (4) as the substrate. F) No fermentation product using *E. coli* harboring empty pTrcHis2 vector when 7-hydroxyflavanone (4) was provided.

Besides NAR and ERI, four other commercially available flavanones were tested as substrates using the recombinant *A. andraeanum* DFR enzyme. The biotransformation assay was chosen for that purpose, since these flavanones cannot be synthesized as radio-isotopomers. The recombinant *E. coli* strains were able to reduce the unsubstituted flavanone as well as 7-hydroxyflavanone to the corresponding flavan-4-ols, but not hesperetin or 5,7-dimethoxyflavanone. HPLC analysis also showed two product peaks eluting closely together when the recombinant culture was fed with either flavanone or 7-hydroxyflavanone (FIG. 28). The first peaks to elute were compared to flavan-4-ol standards with 2,4-cis stereocenters, and were determined to be 2,4-cis-flavan-4-ol and 2,4-cis-7-hydroxyflavan-4-ol, respectively. The second peaks to elute, the major enzymatic products, shared nearly identical LV profiles to the 2,4-cis flavan-4-ols but they were presumed to be the 2,4-trans diastereomers.

While this invention has been illustrated by the examples presented herein, routine modifications will be apprent to those skilled in the art. Such modifications are intended to be within the scope of the invention.

---

The invention claimed is:

1. A method of producing a flavonoids in a host cell comprising the steps of:
   a) introducing into the host cell an exogenous nucleic acid comprising a set of genes encoding for enzymes sufficient to direct the synthesis of a desired flavonoid from a substrate, wherein the set of genes comprises *Malus domestica* Flavanone 3-hydroxylase (FHT), *Dianthus gratianovolitanus* or *Anthurium andraeanum* Dihydroflavonol 4-reductase (DFR), *Malus domestica* Anthocyanidin synthase (ANS) and *Petunia x hybrida* UDP-glucose:flavonoid 3-O-glucosyltransferase (3-GT);
   b) providing the substrate to the cells, wherein the substrate is a flavanone;
   c) culturing the cell under conditions permitting the synthesis of the flavonoid by the cells; and
   d) isolating said flavonoids from said cell, wherein the flavonoids is an anthocyanidin selected from the group of anthocyanidins consisting of pelargonidin 3-O-glucoside and cyanidin 3-O-glucoside.

2. The method of claim 1, wherein the substrate is selected from the group consisting of eriodictyol and penta hydroxyflavanone.

3. The method of claim 1, wherein the host cell is *E. Coli*.

* * * * *

UNITED STATES PATENT AND TRADEMARK OFFICE
CERTIFICATE OF CORRECTION

| | | |
|---|---|---|
| PATENT NO. | : 7,338,791 B2 | Page 1 of 1 |
| APPLICATION NO. | : 11/178912 | |
| DATED | : March 4, 2008 | |
| INVENTOR(S) | : Koffas et al. | |

It is certified that error appears in the above-identified patent and that said Letters Patent is hereby corrected as shown below:

In the claims:

Column 72, line 54, "anthocyanidin" should read --anthocyanin--; and

Column 72, line 55, "anthocyanidins" should read --anthocyanins--.

Signed and Sealed this
Nineteenth Day of June, 2012

David J. Kappos
*Director of the United States Patent and Trademark Office*

SEQUENCE LISTING

<160> NUMBER OF SEQ ID NOS: 86

<210> SEQ ID NO 1
<211> LENGTH: 25
<212> TYPE: DNA
<213> ORGANISM: artificial sequence
<220> FEATURE:
<223> OTHER INFORMATION: DFR-F primer

<400> SEQUENCE: 1
gatggtttct agtacaatta acgag                                        25

<210> SEQ ID NO 2
<211> LENGTH: 24
<212> TYPE: DNA
<213> ORGANISM: artificial sequence
<220> FEATURE:
<223> OTHER INFORMATION: DFR-R Primer

<400> SEQUENCE: 2
ctaagcagat ccattttcat gatg                                         24

<210> SEQ ID NO 3
<211> LENGTH: 27
<212> TYPE: DNA
<213> ORGANISM: artificial sequence
<220> FEATURE:

-continued

<223> OTHER INFORMATION: 3GT-F primer

<400> SEQUENCE: 3
catgactact tctcaacttc acattgc                                    27

<210> SEQ ID NO 4
<211> LENGTH: 30
<212> TYPE: DNA
<213> ORGANISM: artificial sequence
<220> FEATURE:
<223> OTHER INFORMATION: 3GT-R Primer

<400> SEQUENCE: 4
tcaagtaagc ttgtgacatt taactagctc                                 30

<210> SEQ ID NO 5
<211> LENGTH: 22
<212> TYPE: DNA
<213> ORGANISM: artificial sequence
<220> FEATURE:
<223> OTHER INFORMATION: F3H-F primer

<400> SEQUENCE: 5
atggctcctc ctgctactac gc                                         22

<210> SEQ ID NO 6
<211> LENGTH: 20
<212> TYPE: DNA
<213> ORGANISM: artificial sequence
<220> FEATURE:
<223> OTHER INFORMATION: F3H-R Primer

<400> SEQUENCE: 6
ctaagcaaat atgtcgtccg                                            20

<210> SEQ ID NO 7
<211> LENGTH: 22
<212> TYPE: DNA
<213> ORGANISM: artificial sequence
<220> FEATURE:
<223> OTHER INFORMATION: ANS-F primer

<400> SEQUENCE: 7
atggtgagct ctgattcagt ga                                         22

<210> SEQ ID NO 8
<211> LENGTH: 22
<212> TYPE: DNA
<213> ORGANISM: artificial sequence
<220> FEATURE:
<223> OTHER INFORMATION: ANS-R Primer

<400> SEQUENCE: 8
tcacttgggg agcaaagcct ct                                         22

<210> SEQ ID NO 9
<211> LENGTH: 39
<212> TYPE: DNA
<213> ORGANISM: artificial sequence
<220> FEATURE:
<223> OTHER INFORMATION: DFR-F-Pst I-Dra I primer

<400> SEQUENCE: 9
ggggctgcag gggtttaaac cgacatcata acggttctg                       39

```
<210> SEQ ID NO 10
<211> LENGTH: 45
<212> TYPE: DNA
<213> ORGANISM: artificial sequence
<220> FEATURE:
<223> OTHER INFORMATION: DFR-R-Hind III primer

<400> SEQUENCE: 10
ccccaagctt cccctaagca gatccatttt catgatgttc taggg            45

<210> SEQ ID NO 11
<211> LENGTH: 30
<212> TYPE: DNA
<213> ORGANISM: artificial sequence
<220> FEATURE:
<223> OTHER INFORMATION: 3GT-F-Pst I primer

<400> SEQUENCE: 11
ggggctgcag ccgacatcat aacggttctg                             30

<210> SEQ ID NO 12
<211> LENGTH: 43
<212> TYPE: DNA
<213> ORGANISM: artificial sequence
<220> FEATURE:
<223> OTHER INFORMATION: 3GT-R-Dra I primer

<400> SEQUENCE: 12
cccctttaaa ccctcaagta agcttgtgac atttaactag ctc              43

<210> SEQ ID NO 13
<211> LENGTH: 39
<212> TYPE: DNA
<213> ORGANISM: artificial sequence
<220> FEATURE:
<223> OTHER INFORMATION: F3H-F-Kpn I-EcoR I primer

<400> SEQUENCE: 13
ggggggtacc gggatatcc cgacatcata acggttctg                    39

<210> SEQ ID NO 14
<211> LENGTH: 38
<212> TYPE: DNA
<213> ORGANISM: artificial sequence
<220> FEATURE:
<223> OTHER INFORMATION: F3H-R-Sal I primer

<400> SEQUENCE: 14
ccccgtcgac cccctaagca aatatgtcgt ccgctggc                    38

<210> SEQ ID NO 15
<211> LENGTH: 30
<212> TYPE: DNA
<213> ORGANISM: artificial sequence
<220> FEATURE:
<223> OTHER INFORMATION: ANS-F-Kpn I primer

<400> SEQUENCE: 15
ggggggtacc ccgacatcat aacggttctg                             30

<210> SEQ ID NO 16
<211> LENGTH: 36
<212> TYPE: DNA
<213> ORGANISM: artificial sequence
<220> FEATURE:
<223> OTHER INFORMATION: ANS-R-EcoR I primer
```

```
<400> SEQUENCE: 16
ccccgatatc ccctcacttg gggagcaaag cctctt                              36

<210> SEQ ID NO 17
<211> LENGTH: 39
<212> TYPE: DNA
<213> ORGANISM: artificial sequence
<220> FEATURE:
<223> OTHER INFORMATION: primer Pc4cL2

<400> SEQUENCE: 17 ggggggata tcggatggga gactgtgtag cacccaaag                            39

<210> SEQ ID NO 18
<211> LENGTH: 39
<212> TYPE: DNA
<213> ORGANISM: artificial sequence
<220> FEATURE:
<223> OTHER INFORMATION: Pc4cL2-R primer

<400> SEQUENCE: 18 cccccccggta ccccttattt gggaagatca ccggatgct                          39

<210> SEQ ID NO 19
<211> LENGTH: 37
<212> TYPE: DNA
<213> ORGANISM: artificial sequence
<220> FEATURE:
<223> OTHER INFORMATION: primer CHS-F

<400> SEQUENCE: 19 gggggatcc ggatggtgac agtcgaggag tatcgta                              37

<210> SEQ ID NO 20
<211> LENGTH: 37
<212> TYPE: DNA
<213> ORGANISM: artificial sequence
<220> FEATURE:
<223> OTHER INFORMATION: Primer CHS-R

<400> SEQUENCE: 20 cccccctgcag ccttaagtag caacactgtg gaggaca                            37

<210> SEQ ID NO 21
<211> LENGTH: 37
<212> TYPE: DNA
<213> ORGANISM: artificial sequence
<220> FEATURE:
<223> OTHER INFORMATION: CHI-A-F primer

<400> SEQUENCE: 21
gggggatatc ggatgtctcc tccagtgtcc gttacta                             37

<210> SEQ ID NO 22
<211> LENGTH: 38
<212> TYPE: DNA
<213> ORGANISM: artificial sequence
<220> FEATURE:
<223> OTHER INFORMATION: Primer CHI-B-R

<400> SEQUENCE: 22
ccccggtacc ccctagactc caatcactgg aatagtag                            38

<210> SEQ ID NO 23
<211> LENGTH: 39
```

```
<212> TYPE: DNA
<213> ORGANISM: artificial sequence
<220> FEATURE:
<223> OTHER INFORMATION: primer F3H-F

<400> SEQUENCE: 23 gggggggggat ccggatggct cctcctgcta ctacgctga                          39

<210> SEQ ID NO 24
<211> LENGTH: 39
<212> TYPE: DNA
<213> ORGANISM: artificial sequence
<220> FEATURE:
<223> OTHER INFORMATION: Primer F3H-R

<400> SEQUENCE: 24 cccccgtcg acccctaagc aaatatgtcg tccgctggc                            39

<210> SEQ ID NO 25
<211> LENGTH: 36
<212> TYPE: DNA
<213> ORGANISM: artificial sequence
<220> FEATURE:
<223> OTHER INFORMATION: primer FLS-F

<400> SEQUENCE: 25
gggggggata tcatggaggt cgaaagagtc caagac                              36

<210> SEQ ID NO 26
<211> LENGTH: 43
<212> TYPE: DNA
<213> ORGANISM: artificial sequence
<220> FEATURE:
<223> OTHER INFORMATION: Primer FLS-R

<400> SEQUENCE: 26 cccccccggta cctcaatcca gaggaagttt attgagcttg cgg                     43

<210> SEQ ID NO 27
<211> LENGTH: 25
<212> TYPE: DNA
<213> ORGANISM: artificial sequence
<220> FEATURE:
<223> OTHER INFORMATION: primer C4H-F

<400> SEQUENCE: 27
atggacctcc tcttgctgga gaagt                                          25

<210> SEQ ID NO 28
<211> LENGTH: 37
<212> TYPE: DNA
<213> ORGANISM: artificial sequence
<220> FEATURE:
<223> OTHER INFORMATION: Primer C4H-R

<400> SEQUENCE: 28
ttaacagttc cttggtttca taacgattat ggagtgg                             37

<210> SEQ ID NO 29
<211> LENGTH: 25
<212> TYPE: DNA
<213> ORGANISM: artificial sequence
<220> FEATURE:
<223> OTHER INFORMATION: primer Pc4cL2-F

<400> SEQUENCE: 29
```

```
atgggagact gtgtagcacc caaag                                            25
```

<210> SEQ ID NO 30
<211> LENGTH: 24
<212> TYPE: DNA
<213> ORGANISM: artificial sequence
<220> FEATURE:
<223> OTHER INFORMATION: Primer Pc4cL2-R

<400> SEQUENCE: 30

```
ttatttggga agatcaccgg atgc                                             24
```

<210> SEQ ID NO 31
<211> LENGTH: 25
<212> TYPE: DNA
<213> ORGANISM: artificial sequence
<220> FEATURE:
<223> OTHER INFORMATION: primer CHS-F

<400> SEQUENCE: 31

```
atggtgacag tcgaggagta tcgta                                            25
```

<210> SEQ ID NO 32
<211> LENGTH: 25
<212> TYPE: DNA
<213> ORGANISM: artificial sequence
<220> FEATURE:
<223> OTHER INFORMATION: Primer CHS-R

<400> SEQUENCE: 32

```
ttaagtagca acactgtgga ggaca                                            25
```

<210> SEQ ID NO 33
<211> LENGTH: 25
<212> TYPE: DNA
<213> ORGANISM: artificial sequence
<220> FEATURE:
<223> OTHER INFORMATION: primer CHI-A-F

<400> SEQUENCE: 33

```
atgtctcctc cagtgtccgt tacta                                            25
```

<210> SEQ ID NO 34
<211> LENGTH: 35
<212> TYPE: DNA
<213> ORGANISM: artificial sequence
<220> FEATURE:
<223> OTHER INFORMATION: Primer CHI-A-R

<400> SEQUENCE: 34

```
ctagactcca atcactggaa tagtagattt ctcgg                                 35
```

<210> SEQ ID NO 35
<211> LENGTH: 30
<212> TYPE: DNA
<213> ORGANISM: artificial sequence
<220> FEATURE:
<223> OTHER INFORMATION: primer gal1C4H-F

<400> SEQUENCE: 35

```
ggggctgcag acggattaga agccgccgag                                       30
```

<210> SEQ ID NO 36
<211> LENGTH: 47
<212> TYPE: DNA
<213> ORGANISM: artificial sequence

```
<220> FEATURE:
<223> OTHER INFORMATION: Primer gal1C4H-R

<400> SEQUENCE: 36
cccctctaga ttaacagttc cttggtttca taacgattat ggagtgg                47

<210> SEQ ID NO 37
<211> LENGTH: 30
<212> TYPE: DNA
<213> ORGANISM: artificial sequence
<220> FEATURE:
<223> OTHER INFORMATION: primer gal1Pc4cL2-F

<400> SEQUENCE: 37
ggggtctaga acggattaga agccgccgag                                   30

<210> SEQ ID NO 38
<211> LENGTH: 34
<212> TYPE: DNA
<213> ORGANISM: artificial sequence
<220> FEATURE:
<223> OTHER INFORMATION: Primer gal1Pc4cL2-R

<400> SEQUENCE: 38
ccccggtacc ttatttggga agatcaccgg atgc                              34

<210> SEQ ID NO 39
<211> LENGTH: 30
<212> TYPE: DNA
<213> ORGANISM: artificial sequence
<220> FEATURE:
<223> OTHER INFORMATION: primer gal1CHS-F

<400> SEQUENCE: 39
ggggaagctt acggattaga agccgccgag                                   30

<210> SEQ ID NO 40
<211> LENGTH: 35
<212> TYPE: DNA
<213> ORGANISM: artificial sequence
<220> FEATURE:
<223> OTHER INFORMATION: Primer gal1CHS-R

<400> SEQUENCE: 40 cccctgcag ttaagtagca acactgtgga ggaca                              35

<210> SEQ ID NO 41
<211> LENGTH: 30
<212> TYPE: DNA
<213> ORGANISM: artificial sequence
<220> FEATURE:
<223> OTHER INFORMATION: primer gal1CHI-A-F

<400> SEQUENCE: 41 gggggggtacc acggattaga agccgccgag                                  30

<210> SEQ ID NO 42
<211> LENGTH: 45
<212> TYPE: DNA
<213> ORGANISM: artificial sequence
<220> FEATURE:
<223> OTHER INFORMATION: Primer gal1CHI-A-R

<400> SEQUENCE: 42
ccccgaattc ctagactcca atcactggaa tagtagattt ctcgg                  45
```

<210> SEQ ID NO 43
<211> LENGTH: 28
<212> TYPE: DNA
<213> ORGANISM: artificial sequence
<220> FEATURE:
<223> OTHER INFORMATION: forward primer

<400> SEQUENCE: 43
cccaagaatt ccgatggccc ttatgacg                                28

<210> SEQ ID NO 44
<211> LENGTH: 34
<212> TYPE: DNA
<213> ORGANISM: artificial sequence
<220> FEATURE:
<223> OTHER INFORMATION: reverse primer

<400> SEQUENCE: 44
gggaagtcga ccgctagccc atagctgaaa ttgg                         34

<210> SEQ ID NO 45
<211> LENGTH: 36
<212> TYPE: DNA
<213> ORGANISM: artificial sequence
<220> FEATURE:
<223> OTHER INFORMATION: primer Pc4cL-2-F - EcoR1

<400> SEQUENCE: 45
ccggaattcg ggatgggaga ctgtgtagca cccaag                       36

<210> SEQ ID NO 46
<211> LENGTH: 36
<212> TYPE: DNA
<213> ORGANISM: artificial sequence
<220> FEATURE:
<223> OTHER INFORMATION: Primer Pc4cL-2-R - SalI

<400> SEQUENCE: 46
cccgtcgacc ccttatttgg gaagatcacc ggatgc                       36

<210> SEQ ID NO 47
<211> LENGTH: 36
<212> TYPE: DNA
<213> ORGANISM: artificial sequence
<220> FEATURE:
<223> OTHER INFORMATION: primer PcFSI-F -NdeI

<400> SEQUENCE: 47
gttccatatg cccatggctc ctacaacaat aaccgc                       36

<210> SEQ ID NO 48
<211> LENGTH: 38
<212> TYPE: DNA
<213> ORGANISM: artificial sequence
<220> FEATURE:
<223> OTHER INFORMATION: Primer PcFSI-R -KpnI

<400> SEQUENCE: 48
ccttggtacc cggctaagct aaattttcat ctgcactc                     38

<210> SEQ ID NO 49
<211> LENGTH: 37
<212> TYPE: DNA
<213> ORGANISM: artificial sequence
<220> FEATURE:
<223> OTHER INFORMATION: primer chsA-F -BamHI

<400> SEQUENCE: 49 gggggggatcc ggatggtgac agtcgaggag tatcgta    37

<210> SEQ ID NO 50
<211> LENGTH: 36
<212> TYPE: DNA
<213> ORGANISM: artificial sequence
<220> FEATURE:
<223> OTHER INFORMATION: Primer chsA-R -PstI

<400> SEQUENCE: 50
cccctgcagc cttaagtagc aacactgtgg aggaca    36

<210> SEQ ID NO 51
<211> LENGTH: 36
<212> TYPE: DNA
<213> ORGANISM: artificial sequence
<220> FEATURE:
<223> OTHER INFORMATION: primer chiA-F -EcoRV

<400> SEQUENCE: 51
ggggatatcg gatgtctcct ccagtgtccg ttacta    36

<210> SEQ ID NO 52
<211> LENGTH: 38
<212> TYPE: DNA
<213> ORGANISM: artificial sequence
<220> FEATURE:
<223> OTHER INFORMATION: Primer chiA-R -KpnI

<400> SEQUENCE: 52
ccccggtacc ccctagactc caatcactgg aatagtag    38

<210> SEQ ID NO 53
<211> LENGTH: 36
<212> TYPE: DNA
<213> ORGANISM: artificial sequence
<220> FEATURE:
<223> OTHER INFORMATION: primer OMT -F -EcoRI

<400> SEQUENCE: 53
cctgaattcg gatggcaccg gaagaagatt cactag    36

<210> SEQ ID NO 54
<211> LENGTH: 35
<212> TYPE: DNA
<213> ORGANISM: artificial sequence
<220> FEATURE:
<223> OTHER INFORMATION: Primer OMT-R -PstI

<400> SEQUENCE: 54
caaactgcag cctcagggat aggcctcaat gaccg    35

<210> SEQ ID NO 55
<211> LENGTH: 23
<212> TYPE: DNA
<213> ORGANISM: artificial sequence
<220> FEATURE:
<223> OTHER INFORMATION: primer PcFSI-F

<400> SEQUENCE: 55
atggctccta caacaataac cgc    23

<210> SEQ ID NO 56

<210> SEQ ID NO 57
<211> LENGTH: 25
<212> TYPE: DNA
<213> ORGANISM: artificial sequence
<220> FEATURE:
<223> OTHER INFORMATION: Primer PcFSI-R

<400> SEQUENCE: 56
ctaagctaaa ttttcatctg cactc                                    25

<210> SEQ ID NO 57
<211> LENGTH: 25
<212> TYPE: DNA
<213> ORGANISM: artificial sequence
<220> FEATURE:
<223> OTHER INFORMATION: primer AFNS2-F

<400> SEQUENCE: 57
atgtctacac ttgtctacag cacac                                    25

<210> SEQ ID NO 58
<211> LENGTH: 23
<212> TYPE: DNA
<213> ORGANISM: artificial sequence
<220> FEATURE:
<223> OTHER INFORMATION: Primer AFNS2-R

<400> SEQUENCE: 58
tcacggtccg gagacaacga ccg                                      23

<210> SEQ ID NO 59
<211> LENGTH: 23
<212> TYPE: DNA
<213> ORGANISM: artificial sequence
<220> FEATURE:
<223> OTHER INFORMATION: primer CPR1-F

<400> SEQUENCE: 59
atgccgtttg gaatagacaa cac                                      23

<210> SEQ ID NO 60
<211> LENGTH: 23
<212> TYPE: DNA
<213> ORGANISM: artificial sequence
<220> FEATURE:
<223> OTHER INFORMATION: Primer CPR1-R

<400> SEQUENCE: 60
ttaccagaca tcttcttggt atc                                      23

<210> SEQ ID NO 61
<211> LENGTH: 23
<212> TYPE: DNA
<213> ORGANISM: artificial sequence
<220> FEATURE:
<223> OTHER INFORMATION: primer CPR-F

<400> SEQUENCE: 61
atggattcta gctcggagaa gtt                                      23

<210> SEQ ID NO 62
<211> LENGTH: 26
<212> TYPE: DNA
<213> ORGANISM: artificial sequence
<220> FEATURE:
<223> OTHER INFORMATION: Primer CPR-R

<400> SEQUENCE: 62
tcaccagaca tctcggagat accttc					26

<210> SEQ ID NO 63
<211> LENGTH: 37
<212> TYPE: DNA
<213> ORGANISM: artificial sequence
<220> FEATURE:
<223> OTHER INFORMATION: primer Gal1FSI-F(HindIII)

<400> SEQUENCE: 63
ggaaaaagct gggacggat tagaagccgc cgagcgg					37

<210> SEQ ID NO 64
<211> LENGTH: 39
<212> TYPE: DNA
<213> ORGANISM: artificial sequence
<220> FEATURE:
<223> OTHER INFORMATION: Primer Gal1FSI-R(KpnI)

<400> SEQUENCE: 64
ggaaaggtac cgggctaagc taaattttca tctgcactc					39

<210> SEQ ID NO 65
<211> LENGTH: 43
<212> TYPE: DNA
<213> ORGANISM: artificial sequence
<220> FEATURE:
<223> OTHER INFORMATION: primer Gal1FSII-F(BamHI/XbaI)

<400> SEQUENCE: 65
ggaaaggatc ctctagaggg acggattaga agccgccgag cgg					43

<210> SEQ ID NO 66
<211> LENGTH: 43
<212> TYPE: DNA
<213> ORGANISM: artificial sequence
<220> FEATURE:
<223> OTHER INFORMATION: Primer Gal1FSII-R(KpnI/SacI)

<400> SEQUENCE: 66
ggaaaggtac cgagctcggg tcacggtccg agacaacga ccg					43

<210> SEQ ID NO 67
<211> LENGTH: 37
<212> TYPE: DNA
<213> ORGANISM: artificial sequence
<220> FEATURE:
<223> OTHER INFORMATION: primer Gal1CPR1(PstI)

<400> SEQUENCE: 67
ggaaactgca ggggacggat tagaagccgc cgagcgg					37

<210> SEQ ID NO 68
<211> LENGTH: 40
<212> TYPE: DNA
<213> ORGANISM: artificial sequence
<220> FEATURE:
<223> OTHER INFORMATION: Primer Gal1CPR1(SalI)

<400> SEQUENCE: 68
ggaaagtcga cgggttacca gacatcttct tggtatctac					40

<210> SEQ ID NO 69
<211> LENGTH: 23
<212> TYPE: DNA

```
<213> ORGANISM: artificial sequence
<220> FEATURE:
<223> OTHER INFORMATION: A. andraeanum forward primer

<400> SEQUENCE: 69
atgatgcaca agggcaccgt gtg                                        23

<210> SEQ ID NO 70
<211> LENGTH: 25
<212> TYPE: DNA
<213> ORGANISM: artificial sequence
<220> FEATURE:
<223> OTHER INFORMATION: A. andraeanum reverse primer

<400> SEQUENCE: 70
tcaatggccg ttgtcttgcc cggtg                                      25

<210> SEQ ID NO 71
<211> LENGTH: 24
<212> TYPE: DNA
<213> ORGANISM: artificial sequence
<220> FEATURE:
<223> OTHER INFORMATION: A. thaliana forward primer

<400> SEQUENCE: 71
atggttagtc agaaagagac cgtg                                       24

<210> SEQ ID NO 72
<211> LENGTH: 25
<212> TYPE: DNA
<213> ORGANISM: artificial sequence
<220> FEATURE:
<223> OTHER INFORMATION: A. thaliana reverse primer

<400> SEQUENCE: 72
ctaggcacac atctgttgtg ctagc                                      25

<210> SEQ ID NO 73
<211> LENGTH: 22
<212> TYPE: DNA
<213> ORGANISM: artificial sequence
<220> FEATURE:
<223> OTHER INFORMATION: B. japonicum forward primer

<400> SEQUENCE: 73
atgagcattg ttctggtcac gg                                         22

<210> SEQ ID NO 74
<211> LENGTH: 21
<212> TYPE: DNA
<213> ORGANISM: artificial sequence
<220> FEATURE:
<223> OTHER INFORMATION: B. japonicum reverse primer

<400> SEQUENCE: 74
tcacgccctg accaggccaa g                                          21

<210> SEQ ID NO 75
<211> LENGTH: 21
<212> TYPE: DNA
<213> ORGANISM: artificial sequence
<220> FEATURE:
<223> OTHER INFORMATION: F. ananassa forward primer

<400> SEQUENCE: 75
atggggttgg gagcagaatc c                                          21
```

```
<210> SEQ ID NO 76
<211> LENGTH: 23
<212> TYPE: DNA
<213> ORGANISM: artificial sequence
<220> FEATURE:
<223> OTHER INFORMATION: F. ananassa reverse primer

<400> SEQUENCE: 76
ctaaccagcc ctgcgctttt cag                                            23

<210> SEQ ID NO 77
<211> LENGTH: 22
<212> TYPE: DNA
<213> ORGANISM: artificial sequence
<220> FEATURE:
<223> OTHER INFORMATION: I. nil forward primer

<400> SEQUENCE: 77
atggtggacg gtaatcatcc tc                                             22

<210> SEQ ID NO 78
<211> LENGTH: 22
<212> TYPE: DNA
<213> ORGANISM: artificial sequence
<220> FEATURE:
<223> OTHER INFORMATION: I. nil reverse primer

<400> SEQUENCE: 78
tcaagctttt aagggcacta cc                                             22

<210> SEQ ID NO 79
<211> LENGTH: 22
<212> TYPE: DNA
<213> ORGANISM: artificial sequence
<220> FEATURE:
<223> OTHER INFORMATION: I. purpurea forward primer

<400> SEQUENCE: 79
atggtggacg gtaatcatcc tc                                             22

<210> SEQ ID NO 80
<211> LENGTH: 22
<212> TYPE: DNA
<213> ORGANISM: artificial sequence
<220> FEATURE:
<223> OTHER INFORMATION: I. purpurea reverse primer

<400> SEQUENCE: 80
tcaagctttt aagggcacta cc                                             22

<210> SEQ ID NO 81
<211> LENGTH: 22
<212> TYPE: DNA
<213> ORGANISM: artificial sequence
<220> FEATURE:
<223> OTHER INFORMATION: L. hybrid forward primer

<400> SEQUENCE: 81
atggagaatg cgaaaggacc cg                                             22

<210> SEQ ID NO 82
<211> LENGTH: 24
<212> TYPE: DNA
<213> ORGANISM: artificial sequence
<220> FEATURE:
```

```
<223> OTHER INFORMATION: L. hybrid reverse primer

<400> SEQUENCE: 82
ttactgaaga gcaacggaga cttg                                        24

<210> SEQ ID NO 83
<211> LENGTH: 24
<212> TYPE: DNA
<213> ORGANISM: artificial sequence
<220> FEATURE:
<223> OTHER INFORMATION: R. hybrida forward primer

<400> SEQUENCE: 83
atggcatcgg aatccgagtc cgtt                                        24

<210> SEQ ID NO 84
<211> LENGTH: 25
<212> TYPE: DNA
<213> ORGANISM: artificial sequence
<220> FEATURE:
<223> OTHER INFORMATION: R. hybrida reverse primer

<400> SEQUENCE: 84
ttagcctgtg actttgacac ggacg                                       25

<210> SEQ ID NO 85
<211> LENGTH: 24
<212> TYPE: DNA
<213> ORGANISM: artificial sequence
<220> FEATURE:
<223> OTHER INFORMATION: Synechocysti forward primer

<400> SEQUENCE: 85
atggaggtca atcactggat agcc                                        24

<210> SEQ ID NO 86
<211> LENGTH: 25
<212> TYPE: DNA
<213> ORGANISM: artificial sequence
<220> FEATURE:
<223> OTHER INFORMATION: Synechocysti reverse primer

<400> SEQUENCE: 86
ttattgggtc ttaacgtagc catgg                                       25
```